United States Patent
Lauzon

(10) Patent No.: US 8,377,222 B2
(45) Date of Patent: Feb. 19, 2013

(54) CLEANING METHOD AND APPARATUS

(76) Inventor: Normand Lauzon, St-Joseph du Lac (CA)

( * ) Notice: Subject to any disclaimer, the term of this patent is extended or adjusted under 35 U.S.C. 154(b) by 666 days.

(21) Appl. No.: 11/547,655

(22) PCT Filed: Apr. 18, 2005

(86) PCT No.: PCT/CA2005/000586
§ 371 (c)(1),
(2), (4) Date: Oct. 5, 2006

(87) PCT Pub. No.: WO2005/099918
PCT Pub. Date: Oct. 27, 2005

(65) Prior Publication Data
US 2008/0210262 A1    Sep. 4, 2008

(30) Foreign Application Priority Data
Apr. 16, 2004 (GB) .................................. 0408651.8

(51) Int. Cl.
*B08B 9/027* (2006.01)
(52) U.S. Cl. ................ 134/22.11; 134/22.12; 134/22.13
(58) Field of Classification Search ................ 134/22.1, 134/22.22, 22.12, 22.15, 22.18
See application file for complete search history.

(56) References Cited

U.S. PATENT DOCUMENTS

| | | | |
|---|---|---|---|
| 2,878,819 A | 3/1959 | Thomas | |
| 3,010,853 A * | 11/1961 | Elliott | 134/13 |
| 4,420,342 A * | 12/1983 | Gettert et al. | 134/3 |
| 5,680,877 A * | 10/1997 | Edstrand et al. | 134/103.1 |
| 5,915,395 A | 6/1999 | Smith | |
| 5,941,257 A | 8/1999 | Gruszczynski, II | |
| 6,027,572 A * | 2/2000 | Labib et al. | 134/8 |
| 6,423,152 B1 * | 7/2002 | Landaas | 134/10 |
| 6,484,736 B1 * | 11/2002 | Kanda et al. | 134/109 |
| 6,627,089 B1 * | 9/2003 | Wilkinson | 210/754 |
| 6,645,310 B2 | 11/2003 | Rinne | |
| 2003/0024550 A1 * | 2/2003 | Rinne | 134/21 |
| 2003/0172963 A1 * | 9/2003 | Sugimoto | 134/168 R |

FOREIGN PATENT DOCUMENTS

GB        2383831 A        7/2003

OTHER PUBLICATIONS

Canadian Intellectual Property Office, Examination Report, Application No. 2,599,930, Jan. 20, 2011.
European Patent Office, Supplementary Partial European Search Report, Application No. 05735813.7, Dec. 27, 2010.

* cited by examiner

*Primary Examiner* — Saeed T Chaudhry

(57) ABSTRACT

A method for cleaning an interior surface of a processing equipment using a treatment liquid, the processing equipment including a pipe section defining pipe section first and second ends, the pipe section defining a pipe section volume delimited by the pipe section first and second ends, the pipe section being initially at an initial internal pressure. The method includes introducing a predetermined volume of the treatment liquid, the predetermined volume being substantially smaller than the pipe section volume circulating the predetermined volume of the treatment liquid through the pipe section by simultaneously reducing an internal pressure within the pipe section at a location substantially adjacent the pipe section second end and increasing an internal pressure within the pipe section at a location substantially adjacent the pipe section first end.

24 Claims, 9 Drawing Sheets

CLEANING METHOD AND APPARATUS

FIELD OF THE INVENTION

The present invention relates to the general field of cleaning method and systems and is particularly concerned with a cleaning method and apparatus for use with piping systems and associated equipments.

BACKGROUND OF THE INVENTION

Piping systems, vessels and associated apparatuses are used extensively in many industrial applications wherein fluids and other substances are used, produced or transformed. In certain industries, such as for example pharmaceutical industries and food processing industries, including non-limitatively the dairy industry, cleanliness is of utmost importance and is governed by strict regulatory requirements and standards.

Accordingly, the cleaning of corresponding piping systems, vessels and associated apparatuses must be performed regularly or daily to maintain sanitary standards and to meet strict regulatory requirements. Furthermore, piping systems, associated vessels and associated apparatuses may also require cleaning to permit maintenance thereon and, in some cases, subsequently to such maintenance.

Still furthermore, there exist a plurality of situations wherein fluids used during a given production cycle must be removed from industrial piping systems, vessels and associated apparatuses. For example, in the food processing industry, process fluids need to be removed from some sections or all of the hydraulic circuitry when the circuitry is used for processing a different type of products, or even the same type of products in a different flavour, so as to avoid contamination between products or flavors.

To meet cleanliness requirements and to allow for adequate product and/or flavor separation during processing thereof in the most effective and cost efficient manner, most processing facilities have installed so-called "clean-in-place" (CIP) systems. These CIP systems are often permanent, fixed hard piped systems which operate quickly and reduce temporary installation such as temporary hoses, pumps and the like.

Conventional CIP systems typically include a number of tanks, silos or vessels, associated pumps and valves and interconnecting piping. The conventional clean-in-place systems generally fall in three categories. The first category is the so-called single use category in which the chemical cleaning agent is used once and discarded after use. The second category is the so-called multiple use category in which the chemical cleaning agent is stored after use and subsequently reused for system cleaning. The third category is a combination of both categories.

Regardless of the type of system used, in the food processing industry such as in the dairy industry, the piping system, silos and associated apparatuses such as the filtration apparatuses, the dryers, the mixers, evaporators, pasteurizers, separators, filters, pumps and the like must be periodically cleaned, rinsed and sanitized, disinfected or sterilized so as to be maintained in a satisfactory sanitary condition. Generally speaking, a typical cleaning operation involves an initial rinse cycle using clean or recovered rinse water, a subsequent detergent wash cycle using a detergent solution, a post rinse cycle and a final germicidal step using a sanitizing, asepticising, disinfecting or sterilizing solution. If that solution has a "no rinse" approval at the recommended use concentration no further rinse is required. If there is no such approval, a final rinse must be done with sterile water. In some cases, a last step of drying, draining or performing an air blow with sanitary air is finally performed.

Whether the processed liquid needs to be washed out of the overall circuitry in order to make place for a different product or flavor or for cleaning purposes, five conventional methods are typically used. In accordance with a first prior art method, water is added to the circuitry upstream and is pushed at the back of the processed liquid with the use of the same pumping apparatuses used for processing until it reaches a downstream target location.

The volume of water being pumped is measured using a flow meter or by time. Once the measured volume of water has been pumped throughout the circuitry, the outflow is deviated towards a drain or towards a recuperation tank for further use in the process when possible. Rinsing is then continued towards the drain until clear water flows out of the circuitry.

There are several other ways to make a product recovery at end of process. For example, instead of using a flow meter, the product recovery after end of process is also done in the industry using either a conductivity meter or a turbidity meter or an optometer. That apparatus is normally installed at the end of the circuitry. The water is pumped or pushed at the beginning of the circuitry and the analyser (conductivity meter, turbidity meter or optometer) controls the destination of the fluid (to the further process or to a recovery tank or to drain) based on the set point that was preset. In both cases (this one and the one using a flow meter), the disadvantages are the same. There is still a considerable amount of water used.

A large amount of water is used to push the product being cleaned out of the circuitry. The greater the size of the circuitry or piping system, the greater the volume of water required as there will be an important dilution factor.

In situations wherein the push out of a given product is performed between two types of products, the inverse procedure must also be performed. Indeed, the second product will be used to push the water downstream. In such instances, water flows towards the drain until there is a noticeable phase change or cut. Because of the dilution factor, the phase change or cut does not happen sharply and, hence, the product-water mixture must be deviated towards the drain until there is the downstream flow of substantially pure product (without any significant dilution).

When the cleaning of the circuitry is being performed, the same type of steps must be used to bring the disinfecting or washing liquid into the circuitry and also to push the latter out of the circuitry. In other words, between each phase, water is used to eliminate food product or washing product residues, which also causes a relatively large amount of water to be used. In addition, in some cases the returning water and residues needs to be treated before being released, which results in relatively large costs due to the relatively large quantity of returning water and residues to process.

A third method for pushing a fluid out of a circuitry involves the use of pressurized air. Pressurized air is introduced upstream in the circuitry in order to push the liquid downstream. This method is mainly used in situations prohibiting the mixing of water and the product.

The use of pressurized air is responsible for numerous drawbacks. For example, incorporating air into the product may result in oxidizing the final product and, hence, altering its taste and its expected lifetime. Also, incorporation of air in the product may result in the production of foam, which may render the process inaccurate.

Furthermore, the use of air to push the product downstream may create preferential pathways in the piping system. Part of the product only is then pushed out of the circuitry. Accordingly, there is a loss of product since the air is often unable to push all of the product downstream, particularly in situations wherein there are changes in piping diameter and wherein there exists vertical piping in certain areas, which is often the case.

A fourth principle used in product recovery includes the use of a so-called "pig system". The recovery is done using some kind of recovery device, such as for example a cork, a plug or a ball that fits and can slide into the pipe from an insertion point A to an outlet point B. After the end of process, the recovery device is inserted at the beginning of the process circuitry via a Y type of pipe with pressurized air. That same air then pushes this recovery device from point A until it reaches point B, and then through a an outlet including a Y type of pipe again. That system is mainly seen in applications where the product to move out is viscous.

However, that principle is rarely seen because of the following drawbacks:
   i. the recovery device can become stuck in the pipe, which sometimes even require that the pipe be cut for recovery of the recovery device;
   ii. to identify where the recovery device may become stuck, the recovery device typically contains a magnet and, outside the pipe, magnet detectors are installed along the pipe, this results in a relatively expensive cleaning system;
   iii. the recovery device is practically only usable in pipes of substantially constant diameter with no protruding valve. As soon as the circuitry has valves, plates, pumps, filters or any other process equipment, this principle can't be used; and
   iv. curved pipes need to have relatively large radius of curvature, which is relatively expensive and can present a problem of space in the plant.

A fifth principle used in the cleaning of pipes includes solid granules mixed with fluids. The fluid and granules mixture are either pushed with a pressurized gas or pulled through a partial or total vacuum. However, in this method the granules complicate an eventual recovery of food residues that are washed using this fifth principle. Furthermore, this principle cannot typically be used to clean processing equipment in which vessels are equipped with spray devices because the granules may plug the vessel spray device, or they can settle at the bottom of the vessel and be relatively hard to dislodge.

Also, systems using this principle are relatively complex and therefore relatively expensive and relatively more prone to malfunction than systems wherein only a fluid is used. Furthermore, before being reused, if such a reuse is desired, the granules typically need to be washed and disinfected.

Accordingly, there exists a need in the industry for an improved cleaning method and apparatus for use with piping systems, vessels and associated equipment.

OBJECTS OF THE INVENTION

An object of the present invention is therefore to provide an improved cleaning method and an improved cleaning apparatus.

SUMMARY OF THE INVENTION

In a first broad aspect, the invention provides a method for cleaning an interior surface of a processing equipment using a treatment liquid, the processing equipment including a pipe section defining pipe section first and second ends, the pipe section defining a pipe section volume delimited by the pipe section first and second ends, the pipe section being initially at an initial internal pressure. The method includes:
   introducing a predetermined volume of the treatment liquid into the pipe section at a location substantially adjacent the pipe section first end, the predetermined volume being substantially smaller than the pipe section volume; and
   circulating the predetermined volume of the treatment liquid through the pipe section by simultaneously
      reducing an internal pressure within the pipe section at a location substantially adjacent the pipe section second end to a level substantially below the initial internal pressure; and
      increasing an internal pressure within the pipe section at a location substantially adjacent the pipe section first end to a level substantially above the initial internal pressure.

In some embodiments of the invention, the treatment liquid is atomized into the first pipe. In other embodiments of the invention, the treatment liquid is introduced into the first pipe as a substantially coherent volume of liquid. Atomizing the treatment liquid has many advantages, including non-limitatively improving wetting of the surfaces to treat wet, lengthening a time during which an active component of the treatment liquid contacts the surface to clean and helping in sterilizing air circulated within the processing equipment if an atomized sanitizer contains oxidizing components.

The treatment liquid is any suitable liquid, including non-limitatively water, an acid solution, a caustic solution, a germicidal solution, an alkaline solution, a buffer solution, a water-based solution containing an organic solvent, an enzyme-containing solution, a biologically active mixture, or any other suitable liquid usable to clean a pipe section, processing equipment in fluid communication with the pipe section, or both. Biologically active mixtures include non-limitatively mixtures of water or a suitable solution with bacterias, phages, viruses, or yeasts, among others.

Advantages of the present invention include that only part of the overall piping system and/or associated receptacles and/or apparatuses need to be filled in order to be able to perform various treatments such as a change in product or in product flavor, the cleaning of the processing equipment or any other suitable treatments or processes.

The required volumes of liquids are reduced or minimized with respect to many existing cleaning methods, hence leading to smaller required volumes of rinsing waters and products or solutions, such as for example cleaning and/or aseptcising products and solutions and the like. The reduced required volumes of liquid also lead to a reduced required amount of energy, for example a reduced amount of energy required for heating the various liquids.

Furthermore, at the end of a given production cycle, but prior to the introduction of a cleaning agent in the equipment to clean, any liquid remaining in the circuitry may be pushed downstream with a relatively small volume of water. Consequently, the recovered liquid is less diluted and may be reconcentrated more easily and more economically reinserted into a process. Still furthermore, the required storage volumes for performing the same recuperation steps are decreased. Hence, not only are there reduced losses of product, but also the used recovered water contains a more concentrated amount of residues and is produced in smaller quantities.

Still furthermore, the phase separations between the various liquids such as between the processed liquid and water, the treatment solutions and water and so forth are relatively sharp. As a result, recuperation of the various treatment liquids is enhanced. The purity of such treatment liquids is also enhanced, hence allowing for a greater number of reuse of such treatment liquids.

Accordingly, the proposed method and device is not only more environmentally friendly, but also are more economical than many prior art method and devices.

Still furthermore, the proposed device or system is manufacturable using conventional circuitry items so as to provide an improved system that will be economically feasible, long-lasting and relatively trouble-free in operation.

Still furthermore, some embodiments of the invention allow using some processing equipments that are typically present in a production line to perform the cleaning process. This leads to cleaning apparatuses that are less expensive to manufacture and maintain.

Still furthermore, the present invention is usable to clean equipment other than pipes, such as silos, still using relatively small quantities of fluids as leading and returning pipes need not to be filled completely with fluids.

In addition, the use of treatment liquids that do not entirely fill the section of pipe to clean allow to circulate the treatment liquids relatively faster than in many prior art devices, and in some embodiments of the invention, to circulate the treatment liquids through pipes of non-uniform diameters.

In another broad aspect, the invention provides an apparatus for cleaning an interior surface of a processing equipment using a treatment liquid, the processing equipment including a pipe section defining pipe section first and second ends, the pipe section defining a pipe section volume delimited by the pipe section first and second ends, the pipe section being initially at an initial internal pressure. The apparatus includes:
   a controller;
   a treatment liquid source;
   a treatment liquid feeder in fluid communication with the treatment liquid source and with the pipe section first end, the treatment liquid feeder being connected to the controller, the treatment liquid feeder being controllable by the controller to allow an introduction of a predetermined volume of the treatment liquid into the pipe section at a location substantially adjacent the pipe section first end, the predetermined volume being substantially smaller than the pipe section volume;
   a low pressure source in fluid communication with the pipe section, the low pressure source being selectively operatable to produce a reduction in an internal pressure within the pipe section at the location substantially adjacent the pipe section second end to a level substantially below the initial internal pressure; and
   a high pressure source in fluid communication with the pipe section, the high pressure source being selectively operatable to produce an increase in an internal pressure within the pipe section at the location substantially adjacent the pipe section first end to a level substantially above the initial internal pressure;
   wherein the increase in the internal pressure within the pipe section at the location substantially adjacent the pipe section first end and the reduction in the internal pressure within the pipe section at the location substantially adjacent the pipe section second end are produced simultaneously to circulate the predetermined volume of the treatment liquid through the pipe section.

In yet another broad aspect, the invention provides an apparatus for cleaning an interior surface of a processing equipment using a treatment liquid, the processing equipment including a pipe section defining pipe section first and second ends, the pipe section defining a pipe section volume delimited by the pipe section first and second ends, the pipe section being initially at an initial internal pressure. The apparatus includes:
   controlling means for controlling at least in part the apparatus;
   a treatment liquid source;
   treatment liquid feeding means for introducing a predetermined volume of the treatment liquid into the pipe section at a location substantially adjacent the pipe section first end, the predetermined volume being substantially smaller than the pipe section volume;
   low pressure production means for producing a reduction in an internal pressure within the pipe section at a location substantially adjacent the pipe section second end to a level substantially below the initial internal pressure; and
   high pressure production means for producing an increase in an internal pressure within the pipe section at a location substantially adjacent the pipe section first end to a level substantially above the initial internal pressure;
   wherein the increase in the internal pressure within the pipe section at the location substantially adjacent the pipe section first end and the reduction in the internal pressure within the pipe section at the location substantially adjacent the pipe section second end are produced simultaneously to circulate the predetermined volume of the treatment liquid through the pipe section.

Other objects, advantages and features of the present invention will become more apparent upon reading of the following non-restrictive description of preferred embodiments thereof, given by way of example only with reference to the accompanying drawings.

DETAILED DESCRIPTION

The following description often refers to specific types of vessels, such as reservoirs, tanks and silos, among others. The reader skilled in the art will readily appreciate that the use of a specific type of vessel is made for illustration purposes and that in any case wherein a specific type of vessel is mentioned, it is within the scope of the invention to use also any other suitable type of vessel.

Figure 1:
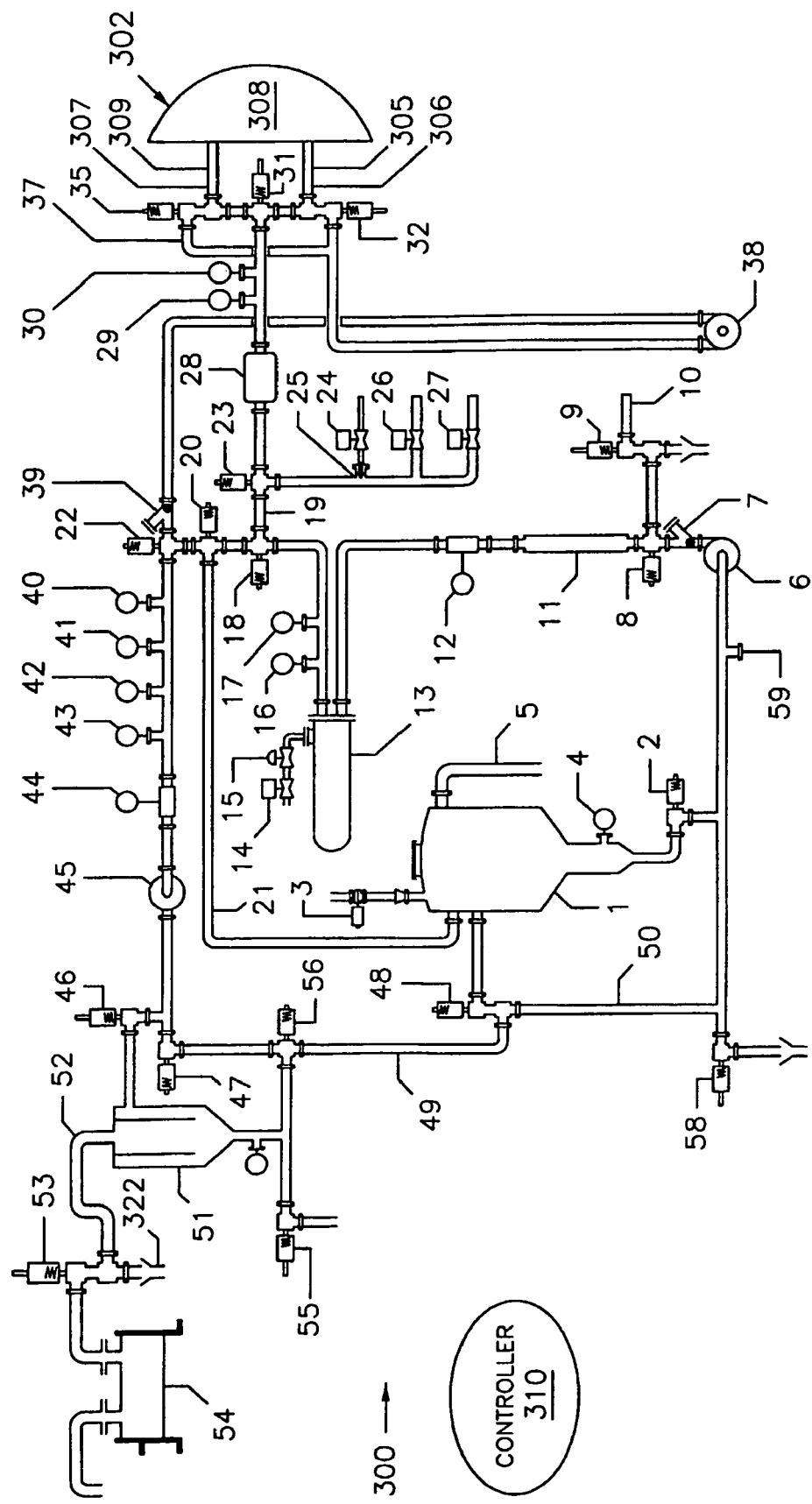
FIG. 1, in a schematic view, illustrates a cleaning apparatus in accordance with an embodiment of the present invention, the cleaning apparatus being shown connected to a processing equipment to clean.

FIG. 1 illustrates in a schematic view an apparatus 300 for cleaning an interior surface of a processing equipment, referred to generally by the reference numeral 302. The apparatus 300 is a so-called clean-in-place apparatus that is permanently, or semi-permanently connected to the processing equipment 302. However, the reader skilled in the art will readily appreciate that the claimed invention is also applicable to apparatuses that are non-permanently connected to a processing equipment to clean.

The processing equipment 302 includes a first pipe section 305 defining a first pipe section first end 306 and a first pipe section second end 307. The first pipe section 305 defines a first pipe section volume extending between the first pipe section first and second ends 306 and 307.

The processing equipment 302 also includes other processing devices, such as for example silos, other pipe sections, or any other type of suitable equipment that is known in the art. The other processing devices are referred to by the reference numeral 308. The first pipe section 305 is in fluid communication with the processing devices 308.

The reader skilled in the art will readily appreciate that FIG. 1 is only schematic and that the first pipe section 305 is generally, but not necessarily, relatively long. Also, although not specifically illustrated in FIG. 1, the first pipe section 305 is generally part of a process line wherein a substance is processed. A non-limitative example of such a substance is a liquid destined to human consumption.

Although not present in all the embodiments of the invention, the processing equipment 302 also includes a second pipe section 309 in fluid communication with the processing devices 308.

Generally speaking, the apparatus 300 implements a method for cleaning the interior surface of the processing equipment 302 with a treatment liquid. For example, and non-limitatively, the apparatus 300 implements a method for cleaning the interior surface of the first pipe section 305.

The treatment liquid is any suitable liquid. For example, the treatment liquid includes water, a treatment solution, or any other treatment liquid. In some embodiments of the invention, only one treatment liquid is used. In other embodiments of the invention, a plurality of treatment liquids is used.

The method includes introducing a predetermined volume of the treatment liquid into the first pipe section 305 at a location adjacent the first pipe section first end 306. The predetermined volume of the treatment liquid is substantially smaller than the first pipe section volume. Subsequently, the predetermined volume of the treatment liquid is circulated through the first pipe section 305 from the first pipe section first end 306 to the second pipe section second end 307. The circulation is performed by simultaneously reducing the internal pressure within the first pipe section 305 at a location adjacent the first pipe section second end 307 to a level substantially below the initial internal pressure and increasing the internal pressure within the first pipe section 305 at a location adjacent the first pipe section first end 306 to a level substantially over the initial internal pressure.

In other words, in this example, a volume of the treatment liquid is introduced into the processing equipment 302, the volume of the treatment liquid being substantially smaller than the volume of the pipe section to clean. Then, this predetermined volume of the treatment liquid is circulated within the pipe section to clean through both a pushing action with relatively high pressure and through a sucking action through a relatively low pressure.

A controller 310 controls at least in part the apparatus 300. In other words, at least some of the components of the equipment 310 are connected to the controller 310. These components include actuators that act on fluids circulating within the apparatus 300 and the processing equipment 302. These components also include valves that redirect fluids circulating within the apparatus 300 and the processing equipment 302 towards various portions of the processing equipment 302 and the apparatus 300. Furthermore, some of these components are sensors that allow the controller 310 to monitor the operation of the apparatus 300, and in some embodiments of the invention, to monitor the processing equipment 302.

Although in a specific embodiment of the invention most of the components of the apparatus 300 are connected to the controller 300, in other embodiments of the invention only a few of these components are connected to the controller 310. In yet other embodiments of the invention, no controller 310 is provided and the claimed method is performed by a user manually performing the claimed method.

The reader skilled in the art will readily appreciate that while no connection is explicitly shown in between the various components connected to the controller 310 and the controller 310 per se, these connection have been omitted from the drawings only for clarity purposes.

The apparatus 300 includes a treatment liquid source in the form of a tank 1. The apparatus 300 includes only one tank, namely tank 1. In this case, the tank 1 is usable to feed fresh water to a supply pump so that the water may be pumped into the processing equipment to clean 302. Also, the tank 1 is usable to store a treatment solution that is also introduced into the processing equipment 302. Furthermore, the tank 1 is usable to recover the predetermined volume of the treatment liquid to allow its reinsertion into the processing equipment 302.

In some embodiments of the invention, the tank 1 is configured to be able to provides the treatment liquid to a supply pump 6, described in further details hereinbelow, even if a relatively small portion of the tank when it is filled with liquid. Therefore, the supply pump 6 is able to operate whether a relatively large or a relatively small quantity of the treatment liquid is contained within the tank 1. This type of tank is well known in the art and will therefore not be described in further details.

The tank 1 is further usable to adjust a property of the treatment liquid prior to its insertion into the processing equipment 302, as described in further details hereinbelow. However, in other embodiments of the invention, there is no need to adjust a property of the treatment liquid prior to its insertion into the processing equipment 302.

In some embodiments of the invention, emptying of the tank 1 is controllable through a tank outlet valve 2. The tank outlet valve 2 allows the treatment liquid to flow out of the tank 1 when in an opened configuration and prevents the treatment liquid to flow out from the tank 1 when in a closed configuration.

A fresh water feed valve 3 allows to selectively admit into the tank 1 aqueduct water through a suitable connection to the aqueduct (not shown in the drawings). However, in alternative embodiments of the invention, no connection to the aqueduct is provided and, therefore, the fresh water feed valve 3 is not necessary in these embodiments.

Also, in some embodiments of the invention, a tank level sensor 4 is provided to measure a level of the treatment liquid within the tank 1. The tank level sensor allows to control the quantity of liquid present within the tank 1, to confirm that the tank 1 is empty if any step of the above described method requires that this tank be empty or to confirm that the first volume of the first treatment liquid is properly recovered within the tank 1 in embodiments of the invention wherein this is desirable.

Also, the tank level sensor allows preventing the operation of the supply pump 6 under conditions wherein an insufficient quantity of the treatment liquid is contained within the tank 1. In some embodiments of the invention, an overflow pipe 5 is provided so that liquid might overflow through the overflow pipe 5 if the level of the treatment liquid within the tank 1 reaches a predetermined level above which operation of the tank 1 becomes, for example, hazardous or sub-optimal, among other conditions wherein the tank 1 should not be operated.

A supply pump 6 is in fluid communication with the tank 1. This supply pump forces the treatment liquid towards the first pipe section 305. In some embodiments of the invention, the supply pump 6 also allows to circulate the treatment liquid in a closed circuit outside of the processing equipment 302 for purposes that are described in further details hereinbelow. Also, the supply pump 6 is in fluid communication with a by-pass pipe 50 so as to be able to pump the liquid supplied through this by-pass pipe 50. In some embodiments of the invention, a check valve 7 is provided downstream of the supply pump 6 so as to stop liquids from flowing towards the tank 1.

In some embodiments of the invention, one or more sources of drinkable aqueduct water are provided in fluid communication with the processing equipment 302. For example, as shown in FIG. 1, one of these sources includes a cross body valve 8 and a block and bleed valve 9. The bleed valve 9 is connected to an aqueduct feed pipe 10 and controls an admission of water towards the cross body valve 8. The cross body valve 8 selectively allows the admission of aqueduct water into the apparatus 300.

In the apparatus 300, the cross body valve 8 is provided immediately downstream from the supply pump 6. However, the location of a drinkable aqueduct water source within a similar apparatuses may be at any other suitable location. Also, in other embodiments of the invention, more than one drinkable aqueduct water sources are provided.

In some embodiments of the invention, a strainer 11 is provided to stop debris from being pumped towards the processing equipment 302. For example, and non-limitatively, the strainer 11 is provided downstream of the pump 6. However, in other embodiments of the invention, the strainer 11 is not provided.

In some embodiments of the invention, a supply flow meter 12 is provided for measuring the flow of the treatment liquid pumped by the supply pump 6 towards the processing equipment 302. However, in alternative embodiments of the invention, the supply flow meter 12 is not provided and determination of the volume of the treatment liquid provided to the processing equipment 302 is performed by measuring time interval during which the pump 6 is activated. In yet other embodiments of the invention, a level sensor in the tank 1 from which the treatment liquid is pumped is used to determine when the predetermined volume of the treatment liquid has been pumped.

If regulation of the temperature of the first treatment liquid is desired, a heat exchanger 13 is provided downstream of the pump 6 so that the temperature of the treatment liquid is suitable adjustable. The heat exchanger 13 admits steam through a shut-off steam valve 14 and a regulating steam valve 15, which may be both connected to the controller 310, but which are not necessarily connected to the controller 310. A temperature sensor 16 is provided downstream of the heat exchanger 13 and allows to suitably control the modulating steam valve 15 so as to suitably adjust the temperature of the treatment liquid.

In some embodiments of the invention, water and a solute are provided separately and thereafter mixed to produce a treatment solution, such as for example a detergent-containing solution, an acid solution, a caustic solution, a buffer solution, a neutral solution, an enzyme-containing solution, or any other suitable treatment solution usable to dean the processing equipment 302. In some embodiments of the invention, water or any suitable solution is also mixable a biologically active components to form a biologically active mixture.

In these embodiments, an adjustment of the concentration of the treatment solution may require that this concentration be sensed. For example, a conductivity sensor 17 is provided to sense a conductivity of the solution, the conductivity of the solution depending on the concentration of solute within the solution. Then, water may be added or the solute may be added to the treatment solution so that concentration of the solute reaches a predetermined level. Adjustment of the concentration is described in further details hereinbelow.

Downstream of the heat exchanger 13, a circuit feed valve 18 is provided to selectively allow delivery of the treatment liquid to the processing equipment 302 or to prevent this delivery. If this delivery is prevented, in some embodiments of the invention, it is possible to circulate the treatment liquid into a closed circuit allowing to adjust the property of the treatment liquid, such as a temperature of the treatment liquid or a concentration of a solute into a treatment solution, among others.

When the circuit feed valve 18 is closed, the treatment liquid is directed towards a circulation valve 20. When the circulation valve 20 is opened, the treatment liquid is fed by the supply pump 6 into a closed loop circulating return pipe 21 connected to the tank 1. In this case, the treatment liquid is recirculated back to the tank 1, which allows adjusting the property of the treatment liquid, such as a temperature, or a concentration of a solute within a treatment solution, among others.

Indeed, using information provided by the temperature sensor 16, the treatment liquid may be circulated through the tank 1 and the heat exchanger 13 until the temperature of the treatment liquid reaches a predetermined temperature. Also, using information provided by the conductivity sensor 17, the treatment liquid may be recirculated through the tank 1 and passed solute and water sources that are suitably operated to add water or solute until the conductivity of the treatment liquid reaches a predetermined conductivity, the predetermined conductivity being indicative of a predetermined concentration of a solute within a treatment solution. An example of such a solute source is an injection port 59 provided between the tank 1 and the pump 6. The injection port 59 allows injecting suitable substances to form treatment solutions, as described hereinabove.

When the circulation valve 20 is closed, the treatment liquid is directed towards a return circuit through which the treatment liquid passes further to its circulation into the treatment equipment 302. The presence of the valve 22 in the apparatus 300 is not required in every embodiment of the invention. However, it allows more control over the flow of liquids within the apparatus 300 and is usable, for example, to empty completely the tank 1 or to heat the return circuit, among other uses.

The increase in pressure that is responsible in part for the circulation of the treatment liquid within the processing equipment 302 is produced in any suitable manner. For example, the increase in pressure is produced by the injection into the processing equipment 302 of an atomized solution, compressed or pressurized gases, or steam, among others. The injection of these pressurized fluids is performed through the use of individually controlled valves 24, 26 and 27 that respectively control the flow of the atomized solution, compressed or pressurized gas, or steam to a pressurization valve 23 provided between the tank 1 and the processing equipment 302. The pressurization valve 23 is opened further to the injection of the treatment liquid through the valve 23.

In a case wherein the increase in pressure is produced through the injection of an atomized solution, a nozzle 25 is provided to atomize the solution. For example, the atomized solution is a chemical solution of a composition similar to a composition of a treatment solution provided to the processing equipment 302. The reader skilled in the art will readily that appreciate the nozzle 25 is any suitable nozzle that may produce a fine or a mist jet, a vaporized jet, a fog jet, a fumigated jet or a pulverized spray, among others. Also, in other embodiments of the invention, either many sources of atomized solutions are present, or no source of atomized solutions is present.

While in some embodiments of the invention the atomized solution is an atomized solution of a composition substantially similar to the composition of the treatment solution, in other embodiments of the invention, the atomized solution is an atomized solution of a composition substantially different from the composition of the cleaning solution.

In addition, in alternative embodiments of the invention a section of the processing equipment 302 to clean, for example the first pipe section 305, is electrically isolated and charged with an electrical charge of a first type. Then, the atomized treatment solution is charged with an opposite electrical charge prior to being introduced into the section to clean, thereby allowing the charged atomized solution to be attracted towards the interior surface of the charged processing equipment.

In cases wherein a compressed or pressurized gas is introduced to increase pressure, any suitable gas such as, for example, air, nitrogen, carbon dioxide, among others, is used. In a specific example, the gas is steam. In other examples, a dedicated steam source is provided.

While providing an increase in pressure, steam also allows to regulate a temperature of the apparatus 300 and of the processing equipment 302. Such regulation in temperature is suitable in many cleaning processes as cleaning sometimes gains in efficiency if temperature is increased above ambient temperature.

In some embodiments of the invention, it is desired that the treatment liquid introduced into the processing equipment 302 be foamed. In these cases, a mixing chamber 28 and a restricting valve 31 are provided downstream of the valves 23 so as to produce the foamed treatment liquid.

Between the valve 23 and the processing equipment 302, sensors, such as a pressure sensor 29 and an anemometer 30 are provided. These sensors monitor the cleaning process and help in ensuring proper operation of the apparatus 300. However, in alternative embodiments of the invention, the sensors 29 and 30 are not present and no monitoring is performed.

For example, the anemometer 30 is usable to measure a quantity of gas or atomized solution introduced into the processing equipment 302. In this case, monitoring the quantity of gas or atomized solution recovered at the outlet of the processing equipment 302 helps in ensuring that leaks within the processing equipment 302 during the cleaning process are minimized.

The pressure sensor 29 is usable to detect a drop in pressure indicative of an equipment failure or malfunction. The pressure sensor 29 is also usable to provide feedback in cases wherein an increase or a decrease in pressure is to be performed, as described hereinbelow.

In the apparatus 300, the treatment liquid may be circulated within the processing equipment 302 in two different directions. To that effect, two three-way valves 32 and 35 are provided so that they are in fluid communication with the valve 23. The three-way valves 32 and 35 are configured so that the treatment liquid is introducible either into the processing equipment 302 through the first pipe section 305 or through the second pipe section 309.

The configuration of the first and second routing valves 35 and 32 is selected so that the treatment liquid is selectively either introduced into the first pipe section 305 and recovered through the second pipe section 309, or introduced into the second pipe section 309 and recovered through the first pipe section 305. A routing pipe 37 interconnects the routing valves 32 and 35 to ensure that the liquid may flow through the processing equipment 302 in two directions, as described hereinabove.

The reader skilled in the art will readily appreciate that in alternative embodiments of the invention, the routing valves 32 and 35 are not present. Also, in other embodiments of the invention, the treatment fluid is routed trough the processing equipment 302 in any other suitable manner.

The ability to introduce the treatment liquid within the processing equipment 302 at two different locations typically improves an ability of the apparatus 300 to reach with the treatment liquid locations within the processing equipment 302 that might be otherwise relatively hard to reach. Also, this ability helps to heat more uniformly the processing equipment 302 with steam when desired.

Circulation of a treatment liquid in a reverse direction may be performed either using the same treatment liquid that has been circulated in a direct direction, eventually following recovery, or using another batch of a similar or different treatment liquid.

A suction pump 38 is provided downstream of the processing equipment 302 so as to provide a low pressure source that sucks the fluid throughout its circulation into the processing equipment 302. In some embodiments of the invention, the suction pump 38 is not present and, instead, an alternative vacuum source is provided, as described in further details hereinbelow.

In some embodiments of the invention, the difference in pressure between an initial internal pressure of the pipe section to clean and a low pressure generated as the second end of the pipe section to clean is substantially equal to the difference in pressure between an initial pressure within the pipe section to clean and a pressure provided by the high pressure source. In other embodiments of the invention, the difference between these two pressure differences is less than about 10%. In yet other embodiments of the invention, the difference between these two pressure differences is about 10% takes any suitable value. An advantage of having relatively similar increase and decrease in pressure with respect to the initial internal pressure resides in that it reduces hydraulic shocks due to the propagation of liquids and gases within the processing equipment 308.

In some embodiments of the invention, another check valve 39, is provided downstream of the pump 38 so as to prevent reverse flow of liquids through the apparatus 300. However, the check valve 39 is not present in other embodiments of the invention.

In some embodiments of the invention, sensors are further provided downstream of processing equipment 302. Examples of such sensors include a temperature sensor 40, a conductivity sensor 41, a vacuum or pressure sensor 42, an anemometer 43 and a flow meter 44, among others. However, in alternative embodiments of the invention, only some of the above-described sensors are present. In yet other embodiments of the invention, none of these sensors are present. In some embodiments of the invention, the output of the temperature sensor 40, conductivity sensor 41, vacuum or pressure sensor 42, anemometer 43 and flow meter 44 as a function of time is recorded to provide historical data regarding the apparatus 300.

The temperature sensor 40 measures the temperature of the liquids, the gas or the gas & atomized solutions that are returning from the processing equipment 302. This measurement is useful to confirm that the solution or the gas is coming back at a predetermined return temperature. The temperature sensor 40 is also useful to confirm that a cleaning step has been performed at a suitable temperature.

The conductivity sensor 41 measures the conductivity of the returning treatment liquids. As such, it is useful to confirm that the treatment liquids returning from the processing equipment 302 are electrically conducting with a conductivity that is within a predetermined interval indicating that the cleaning method performed by the apparatus 300 is working properly. Also, in a rinsing phase after any chemical phase, wherein water is used, the conductivity sensor may be used to confirm that the rinsing phase is completed when the conductivity of the returning rinsing water falls below a predetermined rinsing completion conductivity level.

The vacuum or pressure sensor measures the pressure (positive or negative) of the returning liquid or gas. That measurement is useful to determine when to apply or remove the application of high or low pressures to various portions of the apparatus 300.

The anemometer 43 measures the displacement of an introduced gas, and in some embodiments of the invention, of an introduced atomized treatment solution, further to its passage through the processing equipment 302. That measurement allows to confirm that a proper flow speed is obtained throughout the processing equipment 302.

The flow meter sensor 44 measures the flow of fluids further to their passage through the processing equipment 302. This allows to confirm a substantially complete return of the fluids that have been introduced into the processing equipment 302, which in turn allows to confirm that a predetermined action, such as for example starting a rinsing phase, may be performed. Also, flow meter transmitter 44 allows to identify losses within the processing equipment 302.

In some embodiments of the invention, an aspirator/blower 45 is provided downstream of the processing equipment 302. The aspirator/blower 45 is usable to create the low pressure that is used to circulate the treatment liquid through the processing equipment 302. In addition, the aspirator/blower 45 is usable to produce a high pressure allowing the push the treatment liquid through the processing equipment 302.

In some embodiments of the invention an atomized treatment fluid is introduced by the apparatus 300 and thereafter circulated through the processing equipment 302 and through the apparatus 300. In these embodiments the aspirator/blower 45 may be used to provide a low pressure source simultaneously with a high pressure source to continuously circulate the atomized treatment fluid. In other embodiments of the invention, the aspirator/blower 45 is not provided.

While a specific location for the aspirator/blower 45 is illustrated in FIG. 1, the reader skilled in the art will readily appreciate that in alternative embodiments of the invention, the aspirator/blower 45 is located at any other suitable location. Also, in some embodiments of the invention, the suction pump 38 has the same ability of aspirating and blowing gas or gas & atomized chemical solution mixture and the aspirator/blower 45 may then not be required. Furthermore, depending of the length or size of the circuit through which the treatment liquid is circulated, a plurality of aspirator/blowers may be provided. Also, this device may not be part of the apparatus 300 without departing from the scope of the invention.

A return block valve 46 and a circuit loop valve 48 are provided to either redirect fluids passing through the valve 22 to a liquid/gas separator 51 or directly into the tank 1. Specifically, when the valve 46 is opened and the valve 47 is closed, the fluids are directed into the liquid/gas separator 51, which then separates gases and liquids further to the circulation through the processing equipment 302. Then, liquids are fed back into the tank 1, for example by opening a valve 56 provided between the aspirator 51 and the tank 1, or, alternatively, the liquids may be discarded through an alternative path. In some embodiments of the invention, a level sensor is also provided for the separator 51 so as to measure a quantity of liquid contained within the separator 51.

Regarding the gases produced by the separator 51, they may be vented, or alternatively sucked through a vacuum pump 54. In this later case, a gas evacuation pipe 52 is connected to a three-way valve 53 that either directs the gases to a vent 322 or to the vacuum pump 54. In alternative embodiments of the invention, the vacuum pump 54 is omitted.

In other embodiments of the invention, the pump 54 is included into the apparatus 300 as described hereinabove to replace either one, or both, of the suction pump 38 and the aspirator/blower 45. In addition, in embodiments of the invention wherein either of the pump 38 or the aspirator/blower 45 are present, the vacuum pump 54 is usable to increase a negative pressure produced within the processing equipment 302.

In other embodiments of the invention the vacuum pump 54 is used to build a negative pressure (with respect to the initial internal pressure) within the first pipe section 305. Subsequently, liquids and pressurized gases are introduced into the first pipe section 305, which produces a release of the negative pressure that forces a relatively fast displacement of the treatment liquid within the pipe section to clean.

A routing pipe 49 is connected to the circulation valve 56 and is directed towards another routing valve 48. The routing valve 48 allows to direct any fluid flowing thereinto either towards the tank 1, with which it is in fluid communication, or towards a by-pass pipe 50 that allows to circulate fluids within the apparatus 300 while by-passing the tank 1. By-passing the tank 1 allows, among other possibilities, to re-direct fluids passing through the valve 48 towards a drain valve 58 that allows to drain the apparatus 300.

In use, the processing equipment 302 is first emptied from liquids. While the processing equipment may be emptied using any suitable known method, it is also within the scope of the invention to empty the equipment 302 by increasing a pressure upstream of the processing equipment 302 and by either simultaneously or alternatively reducing a pressure downstream of the processing equipment 302.

Then, a treatment liquid is introduced and circulated within the processing equipment 302 as described hereinabove. The reader skilled in the art will readily appreciate that while the introduction of either atomized treatment liquids or of only one substantially coherent volume of treatment liquid has been described hereinabove, it is within the scope of the invention to introduce a train of substantially coherent volume of treatment liquids. Also, while the description found hereinabove refers to only the introduction of one type of treatment liquid in a so-called cleaning phase, it is within the scope of the invention to perform a successively plurality of cleaning phases using either similar or different treatment liquids. It is furthermore within the scope of the invention to clean the processing equipment 302 while mixing cleaning phases using substantially coherent volume of treatment liquids and atomized treatment liquids.

Figure 2:
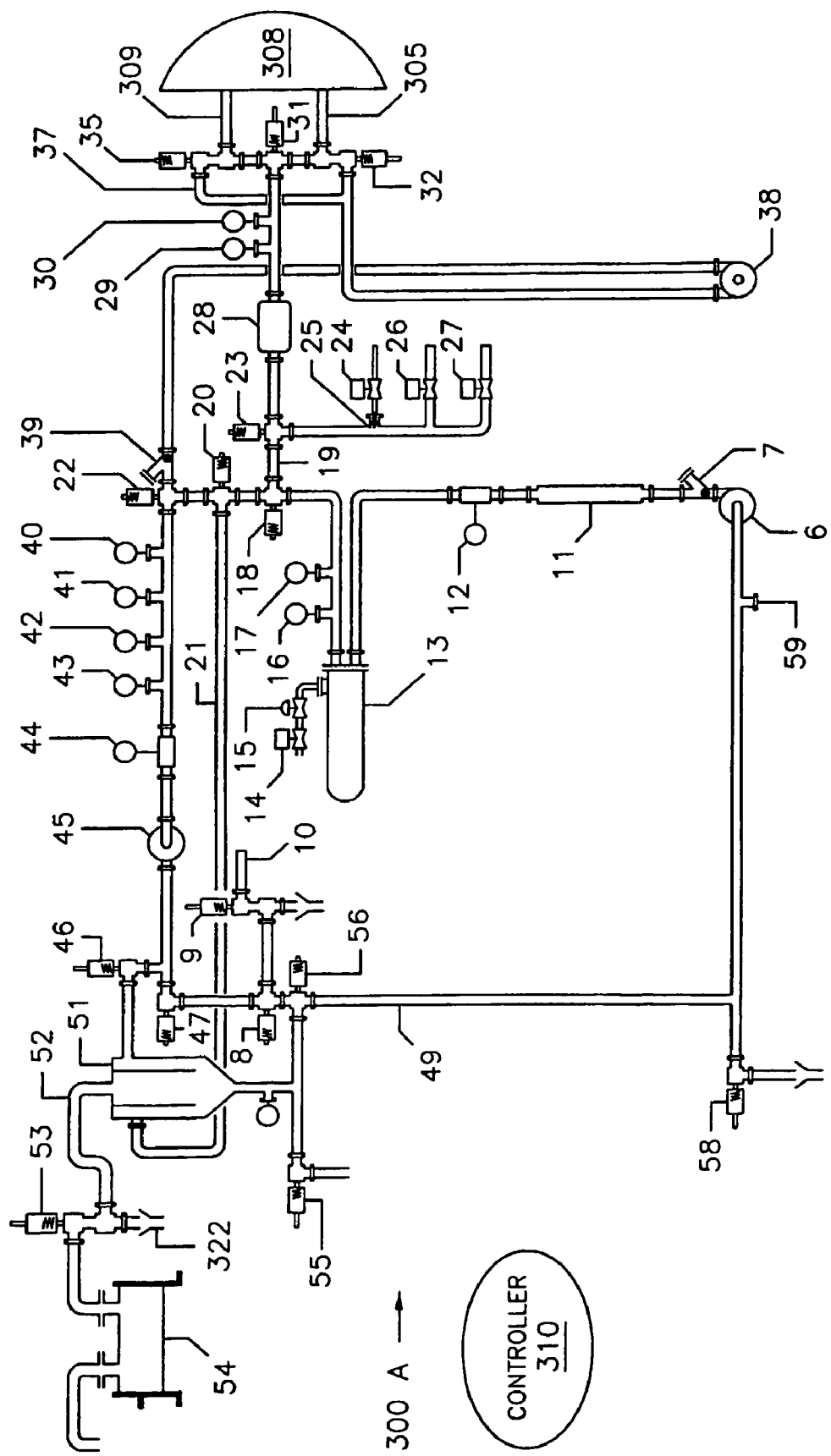
FIG. 2, in a schematic view, illustrates a cleaning apparatus in accordance with an alternative embodiment of the present invention.

FIG. 2 illustrates an alternative apparatus 300a similar to the apparatus 300. A difference between the apparatus 300a and the apparatus 300 resides in that the tank 1, along with the valves 2 and 3, level sensor 4, overflow pipe 5 and valve 48 are not present. Instead, the separator 51 is used both to store the treatment liquid, as the tank 1 performs in the apparatus 300, and to separate liquids from gases, as described with respect to the apparatus 300. To that effect, the valves 8 and 9 are relocated to allow the admission of aqueduct water directly into the routing circulation pipe 49.

Advantageously, this embodiment is more cost effective in some embodiments of the invention as it reduces a number of components required with respect to the number of components required for the apparatus 300.

Figure 3:
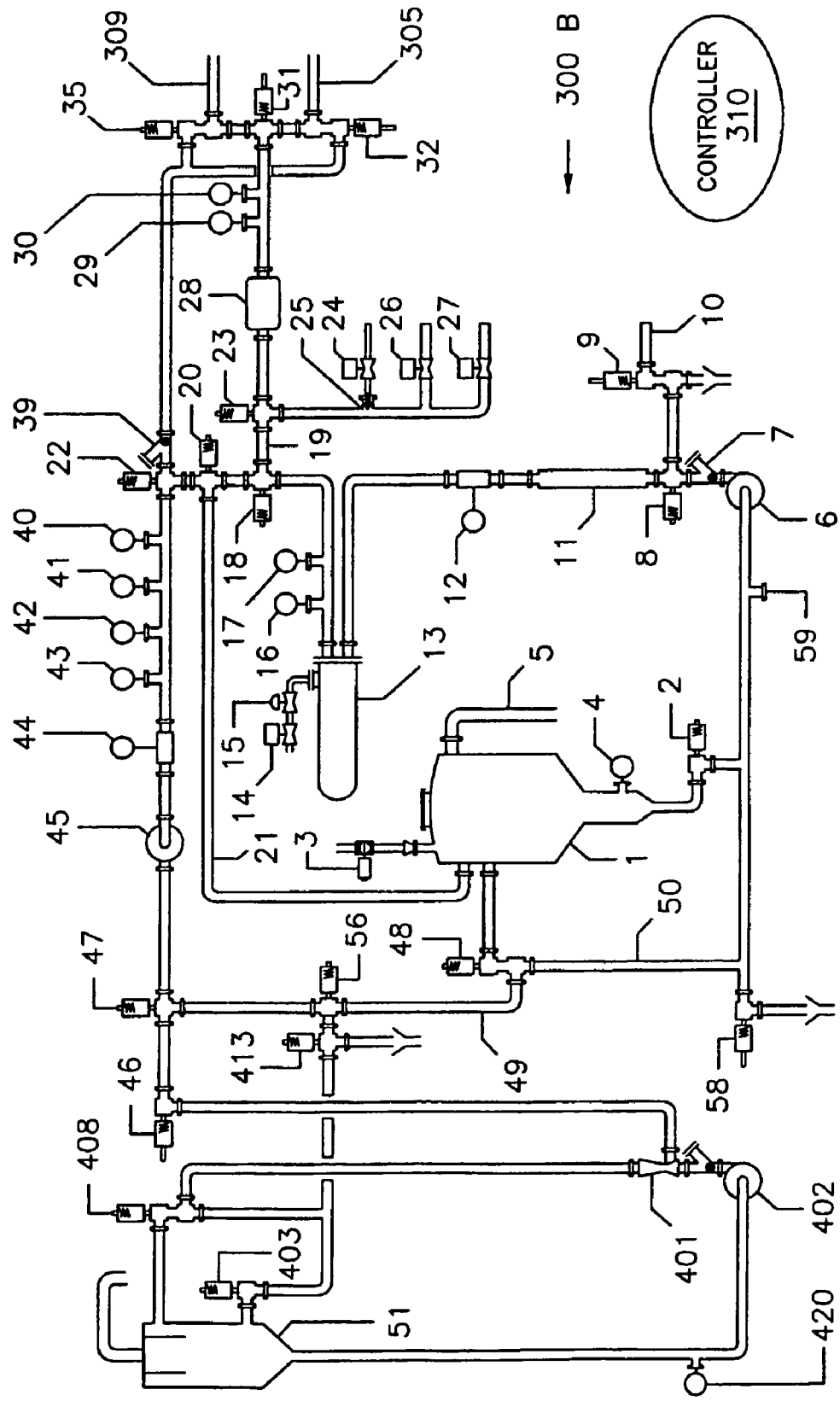
FIG. 3, in a schematic view, illustrates a cleaning apparatus in accordance with another alternative embodiment of the present invention.

FIG. 3 illustrates another alternative embodiment of the invention wherein an apparatus 300b does not include a vacuum pump 54 and associated valves. Instead, an eductor 401 provides a vacuum source. To that effect, a centrifugal pump 402, or any other suitable pump, is connected at an outlet of the separator 51, the pump 402 directs fluids coming out of the separator 51 towards the eductor 401, which is also in fluid communication with the processing equipment 302.

The fluid collected at the eductor 401 is directed towards a valve 408 that either directs the fluid towards the separator 51 or towards the tank 1 through two valves 413 and 56. The valve 413 allows evacuating fluid from the apparatus 300c.

Two sources of fluids arrive at the eductor 401. First, a liquid provided by the separator 51 is pumped by a pump 402 into the eductor 401, thereby creating a suction. Second, liquids and gases that have been pushed and pulled through the processing equipment 302 also arrive at the eductor 401 and are aspired by the suction created by the liquid pushed by the pump 402.

In some embodiments of the invention, an overflow valve is also connected to the separator 51 and allows to direct fluids from the separator 51 towards the valves 413 and 56.

If required, the separator 51 is emptied between phases. In this case, a level sensor 420 is provided below the separator 51 to confirm that the separator 51 is indeed substantially empty. The reader skilled in the art will readily appreciate how to operate the various components of the apparatus 300b to empty the separator 51.

Figure 4:
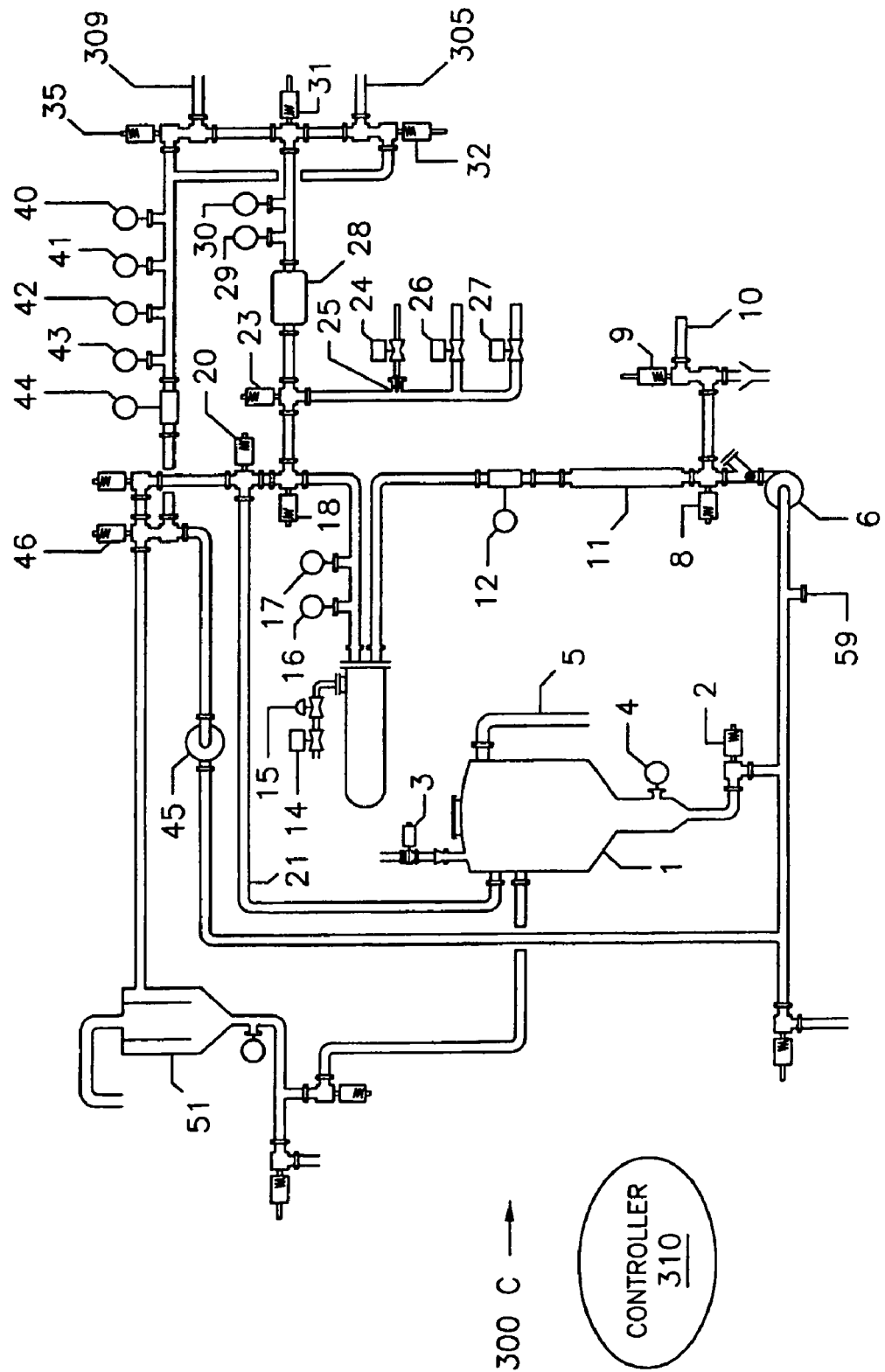
FIG. 4, in a schematic view, illustrates a cleaning apparatus in accordance with yet another alternative embodiment of the present invention.

An alternative apparatus 300c similar to the apparatus 300 is illustrated in FIG. 4. In the apparatus 400c, the vacuum source 54 and associated valves are not present. In addition, the vacuum pump 54 is also absent from the apparatus 300c. In addition, the pump 6 of the apparatus 300c is a pump that acts both by sucking fluids upstream of the pump and pushing fluids in a downstream direction.

The apparatus 300c, and many other alternative embodiments of the invention, allow performing a 2 step batch principle. In a first step, the pump 6 pumps the predetermined volume of the treatment liquid out of tank 1 while other valves that may allow fluids to flow through the pump 6 are closed. The pump 6 forces the liquid from the tank 1 towards the circuit feed valve 18 to valve and into the first pipe section 305. In that first step, no aspiration is performed. However, a gas (or mixture of liquid and gas, or liquid) that is coming back from treatment equipment 302 is allowed to enter the gas/liquid separator 51 is either vented, disposed of, or redirected towards the tank 1.

In a second step, the valve 2 is closed, the three-way valve 46 changes position, the valve 18 is closed and the valve 23 is opened. A pressurized gas is admitted into the first pipe section 305 through the valve 26, which creates an increase in pressure pushing the treatment liquid. At the same time, an aspirating force is produced by the suction of pump 6.

Figure 5:
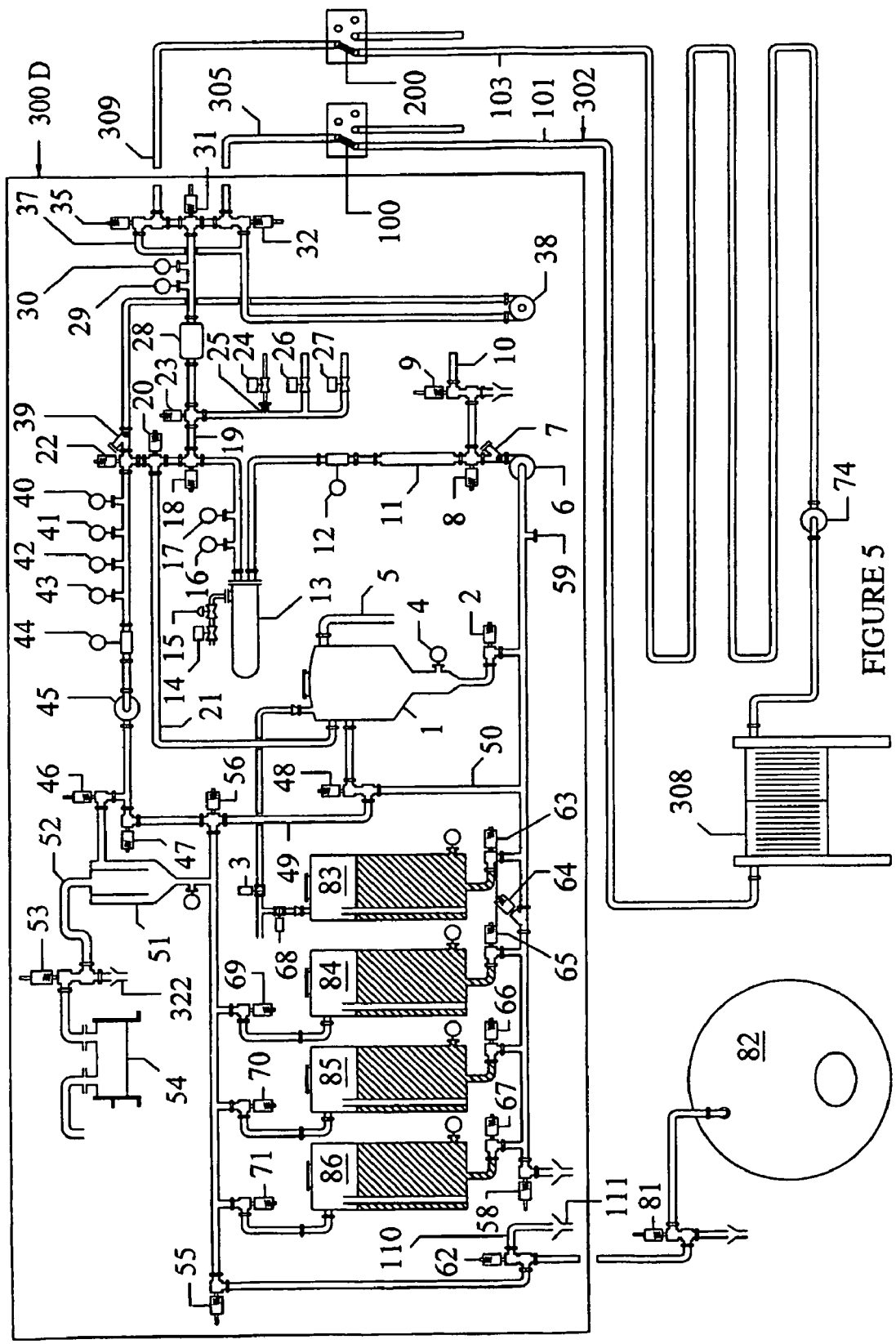
FIG. 5, in a schematic view, illustrates a cleaning apparatus in accordance with yet another alternative embodiment of the present invention.

The apparatus 300c also allows performing a circulation of an atomized treatment solution if the pump 6 is effective to circulate gases FIG. 5 illustrates yet another embodiment of the invention wherein yet an alternative apparatus 300d is connected to the processing equipment 302. The apparatus 300d is substantially similar to the apparatus 300 except that additional tanks are provided. Examples of such additional tanks include non-limitatively a fresh water tank 83, a caustic tank 84, a recovered rinse tank 85, an acid tank 86, and a product recovery silo 82.

Valves 69, 70, 71 and 72 allow to selectively redirect the liquid produced by the separator 51 respectively towards the tanks 84, 85, 86 and the silo 82. Accordingly, in this embodiment of the invention, liquids may be recovered further to their circulation through the processing equipment 302.

Also, valves 63, 65, 66 and 67 control the flow of treatment liquids out from the tanks 83, 84, 85 and 86. The liquids flowing out from the tanks 83 through 86 are directed towards the pump 6.

Also, FIG. 5 illustrates an embodiment of the invention wherein the apparatus 300d may be connectable to a plurality of different sections of the processing equipment 302. To that effect, so-called U-bend connections 100 and 200 are provided to selectively connect the pipes 309 and 305 to different sections of the equipment 308. In other embodiments of the invention, any other suitable switchable pipe connections are provided.

In the embodiment of the invention shown in the drawings, the processing equipment 302 includes pipes 101 and 103 respectively connected to the U-bend connections 100 and 200 so that the pipe sections 309 and 305 are in fluid communication respectively with the pipes 101 and 103. The pipe 103 leads to a pump 74, which pumps fluids towards the apparatus 300d through the pipe 103.

The product recovery silo 82 allows recovering at least in part a substance left within the processing equipment 302. Indeed, circulating a batch of fresh water through the processing equipment 302 and redirecting the fresh water contaminated by any residue left into the processing equipment 302 towards the recovery tank 82 allows to further process the recovered water and product mixture. In some embodiments of the invention, this allows a relatively large increase in the cost effectiveness of the cleaning process.

The appended tables illustrate specific examples of methods that may be performed using various apparatuses illustrated in the drawings. The reader skilled in the art will readily appreciate that the examples given in the tables are non-limiting examples and are provided to better illustrate the claimed invention. However, these examples should not be used to restrict the scope of the invention.

The tables are presented pairwise to improve clarity. For example, tables 1A and 1B illustrate the status of various valves and components shown in FIG. 5 for a specific example of a cleaning method.

In the tables, lines correspond to steps into the example and columns correspond to components illustrated in the drawings. An X at an intersection of a line and a column indicates that for the specific step, the specific component is in an ON or OPEN status. For example, at step 1 of Table 1A, the aqueduct water valve 8 is open, along with the block and bleed aqueduct water valve 9, the routing valve 18, the suction return pump 38 and, as shown in Table 1B, the routing valve to the recovery silo 62. The reader skilled in the art will readily appreciate that this corresponds to introducing aqueduct water through the aqueduct water valve 8 and the block and bleed valve 9 and to route this water through the valve 18 towards the suction return pump 38 and then to the recovery silo 82. The other components of the apparatus 300d mentioned in Tables 1A and 1B are in an OFF or CLOSED status.

Typically, the following actions, generally denoted by the term phase, may be performed during the cleaning process. A phase includes one or more steps. First, there is a recovery phase denoted by letters REC in the Tables wherein any product that might be left within the processing equipment 302 further to emptying is recovered. Then, a rinse phase using water is performed, rinse phases being also typically performed between phases introducing different solutions or liquids within the processing equipment 302.

Another type of phase performed is the so-called wash phase wherein a solution is circulated within the equipment. For example, steps 7 to 12 form a caustic wash phase wherein a caustic solution is circulated within the processing equipment 302. Also, typically at the end of the cleaning method, but not necessarily so, a sanitizing, germicidal, disinfecting, aseptisizing or sterilizing phase is performed.

In each phase, a predetermined volume of the treatment liquid is circulated within the processing equipment 302. Typically, but not exclusively, as shown for example in steps 3 and 4, a treatment liquid is introduced into the equipment and pressure differentials are created to circulate the treatment liquid within the processing equipment 302.

In some embodiments of the invention, this two-steps sequence is performed more than one time during a given phase, sometimes using a reversal of flows within the processing equipment 302, as described hereinabove.

Tables 2A and 2B, 3A and 3B, 4A and 4B, and 5A and 5B, illustrate other non-limitative examples of cleaning methods. Tables 2A and 2B illustrate a cleaning method wherein a treatment solution is foamed during a wash phase. Tables 3A and 3B illustrate a cleaning method wherein atomized treatment solutions and substantially coherent volumes of treatment liquids are both used. Tables 4A and 4B illustrates a cleaning method wherein in some phases an atomized treatment liquid is pressurized into the processing equipment 302, followed by a step wherein a vacuum is provided downstream of the atomized pressurized treatment solution. This pressurization followed by decompression increases a flow speed of the treatment solution within the processing equipment 302, which improves the efficiency of the cleaning method for some specific processing equipment 302. Tables 5A and 5B illustrate a cleaning method wherein in some phases an atomized treatment liquid is introduced into the processing equipment 302 at a pressure below the initial internal pressure within the processing equipment 302. Then an increase in pressure is provided upstream of the atomized pressurized treatment solution while the atomized solution is allowed to flow through the processing equipment 302. This depressurization followed by compression increases a flow speed of the treatment solution within the processing equipment 302, which improves the efficiency of the cleaning method for some specific processing equipment 302.

Figure 6A:
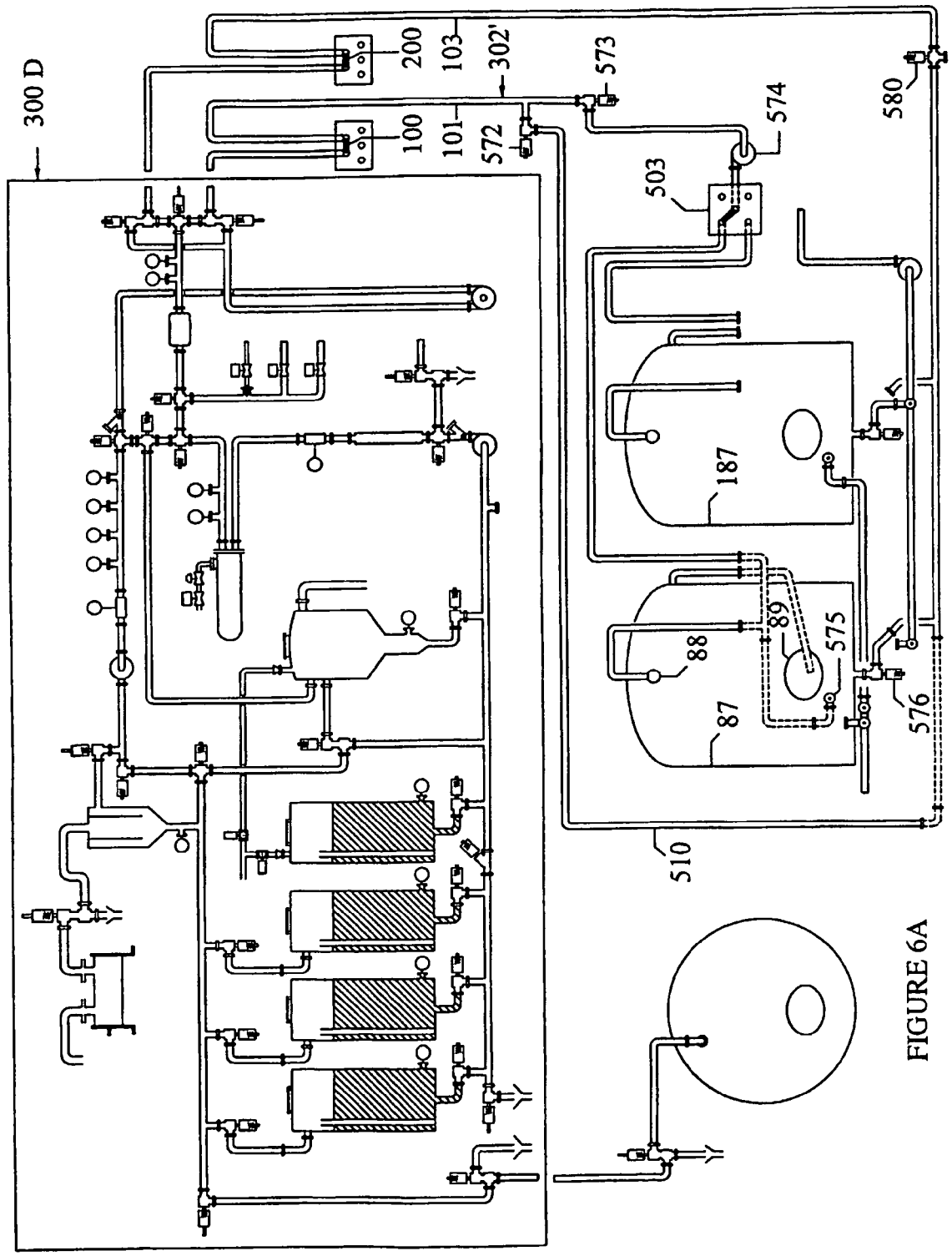
FIG. 6A, in a schematic view, illustrates a cleaning apparatus in accordance with yet another alternative embodiment of the present invention, the cleaning apparatus being shown connected to a processing equipment to clean, the processing equipment including a silo.

FIG. 6A illustrates yet another embodiment of the invention wherein the apparatus 300d is connected to processing equipment 302' that includes at least one silo 87. In FIG. 6A, another silo 187 is shown. However, the apparatus 300d is usable to clean any processing equipments 302' including any suitable number of silos.

Such silos 87 and 187 are well known in the art and typically include a spray ball 88, a door 89, and input and output valves 575 and 576 for respectively admitting and evacuating fluids into and out of the silo 87. The spray ball 88 allows to spray inside the silo 87 any suitable cleaning fluid.

In some embodiments of the invention, a transfer plate 503 is provided so that it is possible to clean selectively one of the silos 87 and 187, or a plurality of silos. However, such a transfer plate is not necessarily present in other embodiments of the invention.

Briefly, valves such as valve 572, valve 573, valve 576 and valve 580 are provided to regulate the flow of cleaning fluid within the silo 87. More specifically, the valves 572 and 573 are located to allow directing any fluid incoming through the pipe 101, including any gas, atomized solution or liquid, to by-pass the silos 87 and 187 and to return directly towards the pipe 503. To that effect, a by-pass pipe 510 is provided between the valve 572 and the pipe 103. This specific path of the treatment liquid through the processing equipment 302' is followed when the valve 572 is opened and the valve 573 is closed.

Alternatively, closing the valve 572 and opening the valve 573 allows to direct the fluid towards the silo 87 so that the treatment liquid first passes through the silo 87 and then drains towards the pipe 103. A valve 580 is provided unto the return pipe 103 and allows controlling the application of a vacuum upstream of the valve 580.

In addition, a pump 574 is provided between the valve 573 and the spray ball 88.

Cleaning of the silo 87 proceeds as follows. First, the valve 572 is closed and the pump 574 is activated with the valve 673 opened. A treatment liquid is introduced by the apparatus 300d as described hereinabove. A pressure drop is caused into the pump 574 within the pipe 101 downstream of the treatment liquid while a pressure increase is produced by the apparatus 300d upstream of the treatment liquid. This allows circulating the treatment liquid within the pipe 101 towards the spray ball 88.

When the treatment liquid reaches the silo, the pump 574 pumps the treatment liquid towards the spray ball 88. Contrarily to prior art equipments, the processing equipment 302' shown in FIG. 6A, along with the apparatus 300d, allow spraying the predetermined volume of treatment liquid into the silo 87 without requiring that the whole pipe 101 leading to the silo 87 be filled with fluid.

Otherwise, cleaning of the silo 87 may proceed in a manner that is well know in the art, including through spraying liquid from the spray ball 88, waiting any suitable amount of time further to spraying and draining the liquid towards the pipe 103. In embodiments of the invention wherein the treatment liquid is atomized the apparatus 300d, the spray ball 88 is used to introduce the atomized treatment liquid within the silo 87.

When the treatment liquid is drained from the silo 87, the valve 573 is closed and the valve 572 is opened, which allows to create an increase in pressure downstream of the treatment liquid within the pipe 103. Also, the valve 580 is opened, which allows creating a pressure decrease upstream of the treatment liquid within the pipe 103. These pressure increase and decrease cause the treatment liquid to circulate within the pipe 103 towards the apparatus 300d, where the treatment liquid is processed similarly in the manner described hereinabove. The reader skilled in the art will appreciate that in alternative embodiments of the invention, the treatment liquid is circulated within the pipes 101 and 103 in any other suitable manner.

The reader skilled in the art will readily appreciate that the above-described manner of operating the processing equipment 302' allows to circulate fluids within the pipes 101 and 103 without necessarily requiring that the silos 87 and 187 be pressurized or depressurized. This allows, among other possibilities, to open the silo door 89. However, if the silos 87 and 187 are designed to withstand pressurization and depressurization, the by-pass pipe 510 may be omitted. In this latter case, the increase in pressure is transmitted to the pipe through the silos 87 and 187 through a suitable operation of the valve 573.

A non-limiting example of a method of operating the apparatus and processing equipment illustrated in FIG. 6 is provided in Tables 6A and 6B.

Figure 6B:
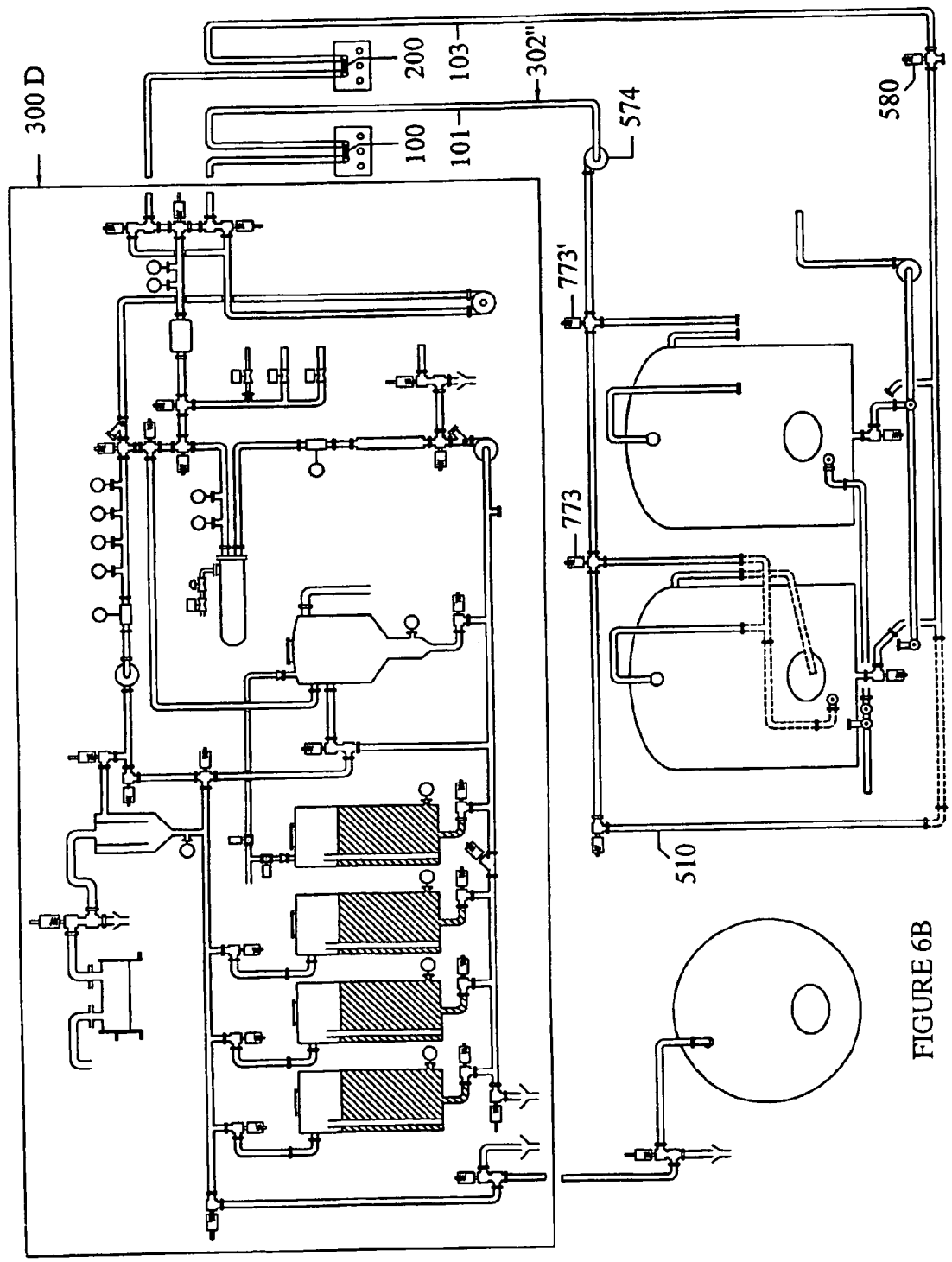
FIG. 6B, in a schematic view, illustrates a cleaning apparatus in accordance with yet another alternative embodiment of the present invention, the cleaning apparatus being shown connected to a processing equipment to clean, the processing equipment including a silo.

FIG. 6B illustrates an alternative embodiment of the invention wherein a processing equipment 302" is configured to direct cleaning fluids towards set-up that is substantially equivalent to the processing equipment 302', but that is realized differently in the processing equipment 302", the transfer plate 503 is replaced by two valves 773 and 773' that direct fluids into the silo 87 or 187, or both, that is to be cleaned. Otherwise, the operation of the processing equipment 302" is substantially similar to the operation of the processing equipment 302'.

Figure 6C:
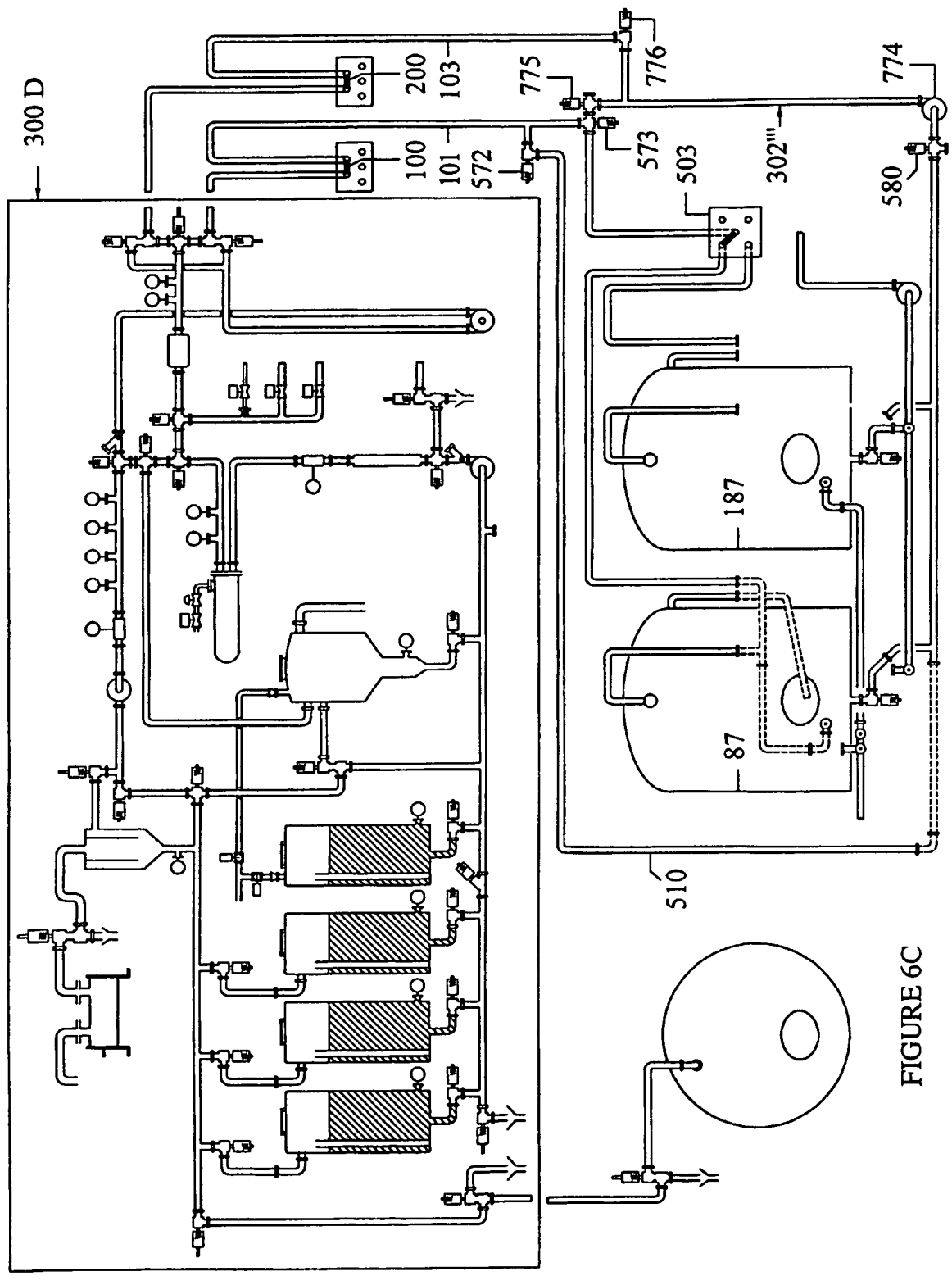
FIG. 6C, in a schematic view, illustrates a cleaning apparatus in accordance with yet another alternative embodiment of the present invention, the cleaning apparatus being shown connected to a processing equipment to clean, the processing equipment including a silo.

FIG. 6C illustrates yet another embodiment of the invention wherein a pump 774 is present downstream of the silos 87 and 187 in a processing equipment 302'''. The pump 774 may be a pump that is used during the process for which the processing equipment 302''' is designed. Valves 775 and 776 are provided to allow to either direct fluids pumped by the pump 774 towards the silos 87 and 187 or towards the apparatus 300d.

If the pump 774 is already present in the processing equipment 302''' prior to the connection thereto of the apparatus 300d, this embodiment of the invention helps in reducing the costs associated with the installation of the apparatus 300d. Indeed, the presence of the pump 774 allows to omit the pump 574 as fluids directed towards the pump 774 through the by-pass pipe 510 may then be directed towards the silos 87 and 187.

Figure 7:
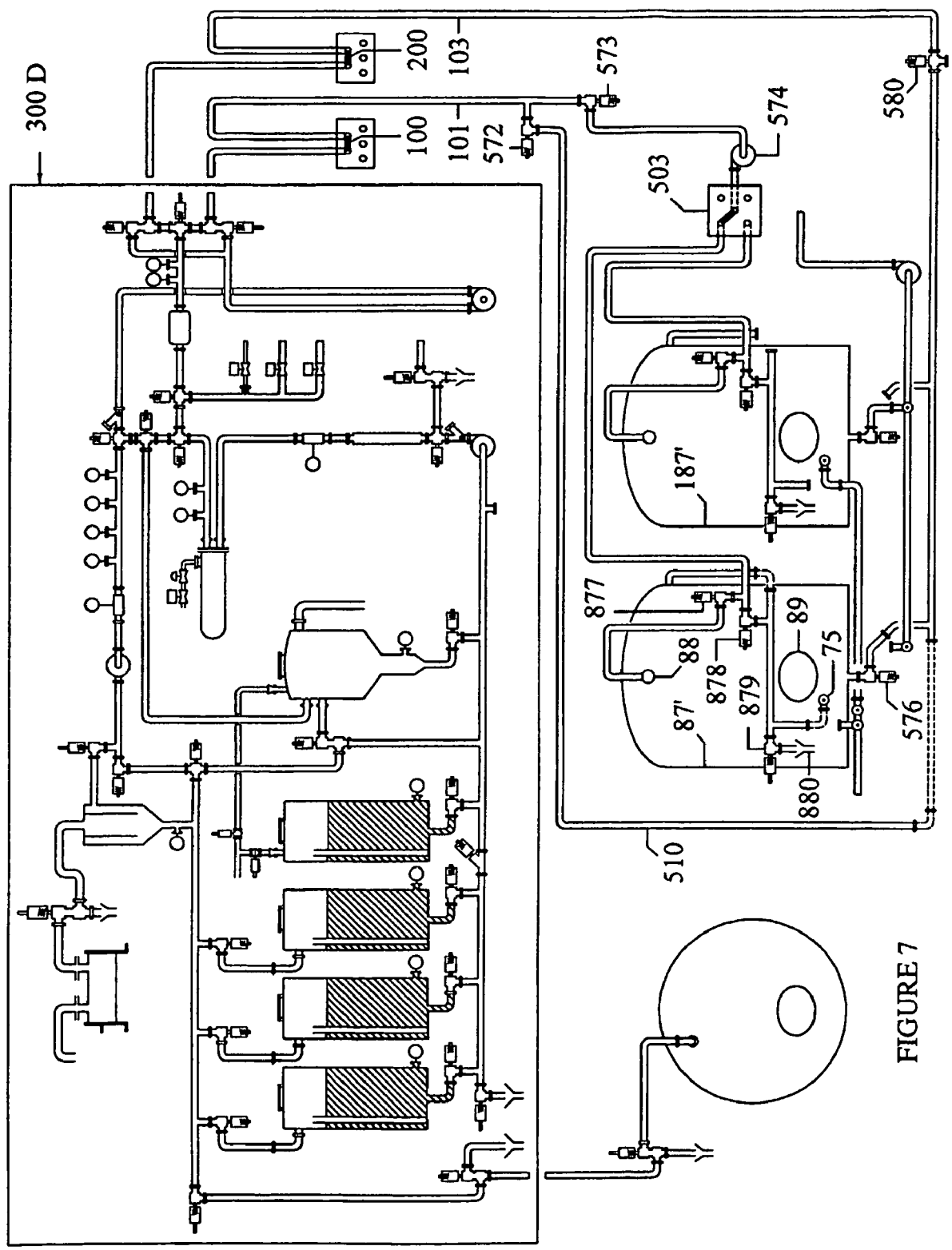
FIG. 7, in a schematic view, illustrates a cleaning apparatus in accordance with yet another alternative embodiment of the present invention, the cleaning apparatus being shown connected to a processing equipment to clean, the processing equipment including a silo.

FIG. 7 illustrates yet another embodiment of the invention that is suitable to clean alternative silos 87' and 187' through the use of atomized treatment liquids. The silos 87' and 187' are similar to the silos 87 and 187 except that additional valves 877, 878 and 879 are provided with suitable interconnecting pipes.

The valve 877 is provided between the wash ball 88 and the valve 573. The valve 877 either allows or prevents fluid to be directed towards the wash ball 88. When the fluids are prevented to reach the wash ball 88, the fluids are directed towards the valve 878, which either allows or prevents fluids to be directed towards the input valve 75.

The valve 879 is provided to prevent the pressure within the silo 87 to increase beyond a safe pressure level. When the safe pressure level is passed, the valve 879 opens and gases are vented through a vent 880.

Therefore, the valves 878, 879 and 880 allow to direct atomized treatment liquids directly into the silos 87' and 187'.

In addition, in some embodiments of the invention the valves 572 and 573, along with the by-pass pipe 510 are omitted and the circulation of the treatment solution through the silos 87' and 187' is performed similarly to the circulation of the treatment solution through the pipes 101 and 103.

Tables 7A and 7B, 8A and 8B, and 9A and 9B illustrate non-limiting examples of methods of operating the apparatus and equipment shown in FIG. 7.

In the embodiments of the invention shown in the drawings, it is possible to also perform other operations similar to cleaning, such as for example destaining, passivaton and dye checks, for example.

Although the present invention has been described hereinabove by way of preferred embodiments thereof, it can be modified, without departing from the spirit and nature of the subject invention as defined in the appended claims.

TABLE 1A

| Step | Phase | CHART 1 (PAGE 1) REFERENCE DRAWING 5 LINE WASH & SANITIZE PROGRAM USING THE PUSH & PULL METHOD STEP DESCRIPTION Item number | Step time or volume | Circulation tank outlet valve - also open 3 in rinse low level 2 | CIP supply pump 6 | Aqueduc water valve 8 | Block & bleed aqueduc water valve 9 | Steam flow valve (also turn on steam shutt off valve 14) 15 | Routing valve from CIP to circuit 18 |
|---|---|---|---|---|---|---|---|---|---|
| 0 |  | Home |  |  |  |  |  |  |  |
| 1 | Rec | Partial rinse to circuit & pull |  |  |  | X | X |  | X |
| 2 |  | Push & pull to recovery silo |  |  |  |  |  |  |  |
| 3 | Rinse | Partial rinse to circuit & pull |  |  | X |  |  |  | X |
| 4 |  | Push & pull to drain |  |  |  |  |  |  |  |
| 5 |  | Do steps 3 & 4 (reverse flow) |  |  |  |  |  |  |  |
| 6 |  | Repeat steps 3-5x time(s) |  |  |  |  |  |  |  |
| 7 | Caustic | Partial caustic sol'n to line |  |  | X |  |  |  | X |
| 8 |  | Push & pull to circulation tk |  |  |  |  |  |  |  |
| 9 |  | Partial caustic sol'n to line |  | X | X |  |  | X | X |
| 10 |  | Push & pull to circulation tk |  | X | X |  |  | X |  |
| 11 |  | Steps 9-10 (+reverse flow) |  |  |  |  |  |  |  |
| 12 |  | Repeat steps 9-11x time(s) |  |  |  |  |  |  |  |
| 13 | Rinse | Empty circulation tank |  | X | X |  |  |  | X |
| 14 |  | Push & pull to caustic tk |  |  |  |  |  |  |  |

TABLE 1A-continued

| Step | Phase | Step Description | | | | | |
|---|---|---|---|---|---|---|---|
| 15 | | Partial rinse to circuit & pull | X | X | | | X |
| 16 | | Push & pull to caustic tk | | | | | |
| 17 | | Repeat steps 15-16x tm(s) | | | | | |
| 18 | Acid | Partial acid sol'n to line | | X | | | X |
| 19 | | Push & pull to circulation tk | | | | | |
| 20 | | Partial acid sol'n to line | X | X | | X | X |
| 21 | | Push & pull to circulation tk | X | X | | X | |
| 22 | | Steps 20-21 (+reverse flow) | | | | | |
| 23 | | Repeat steps 20-22x tm(s) | | | | | |
| 24 | Rinse | Empty circulation tank | X | X | | | X |
| 25 | | Push & pull to acid tank | | | | | |
| 26 | | Partial rinse to circuit & pull | X | X | | | X |
| 27 | | Push & pull to acid tank | | | | | |
| 28 | | Repeat steps 26-27x tm(s) | | | | | |
| 29 | Sanitizing | Partial sanitizer sol'n prep. | | X | | | |
| 30 | | Sol'n sent to circuit & pull | X | X | | | X |
| 31 | | Push & pull to drain | | | | | |
| 32 | | Push & pull (+reverse flow) | | | | | |
| 33 | | Final drain (all lines) | | | X | | X |

| Step | Phase | CHART 1 (PAGE 1) REFERENCE DRAWING 5 LINE WASH & SANITIZE PROGRAM USING THE PUSH & PULL METHOD STEP DESCRIPTION Item number | Routing valve to circulation tank 1  20 | Chemical & compressed gas main valve  23 | Atomized chemical valve (caustic or acid or sanitizer)  24 | Compressed gas valve  26 | Live steam valve (flow controlled)  27 | Flow restriction valve (normally open to circuit)  31 | Routing valves - also activate 35 (reverse flow valves)  32 |
|---|---|---|---|---|---|---|---|---|---|
| 0 | | Home | | | | | | | |
| 1 | Rec | Partial rinse to circuit & pull | | | | | | | |
| 2 | | Push & pull to recovery silo | | X | | X | | | |
| 3 | Rinse | Partial rinse to circuit & pull | | | | | | | |
| 4 | | Push & pull to drain | | X | | X | | | |
| 5 | | Do steps 3 & 4 (reverse flow) | | | | | | | X |
| 6 | | Repeat steps 3-5x time(s) | | | | | | | |
| 7 | Caustic | Partial caustic sol'n to line | | | | | | | |
| 8 | | Push & pull to circulation tk | | X | X | X | X | | |
| 9 | | Partial caustic sol'n to line | | | | | | | |
| 10 | | Push & pull to circulation tk | X | X | X | X | X | | |
| 11 | | Steps 9-10 (+reverse flow) | | | | | | | X |
| 12 | | Repeat steps 9-11x time(s) | | | | | | | |
| 13 | Rinse | Empty circulation tank | | | | | | | |
| 14 | | Push & pull to caustic tk | | X | | X | | | |
| 15 | | Partial rinse to circuit & pull | | | | | | | |
| 16 | | Push & pull to caustic tk | | X | | X | | | |
| 17 | | Repeat steps 15-16x tm(s) | | | | | | | |
| 18 | Acid | Partial acid sol'n to line | | | | | | | |
| 19 | | Push & pull to circulation tk | | X | X | X | X | | |
| 20 | | Partial acid sol'n to line | | | | | | | |
| 21 | | Push & pull to circulation tk | X | X | X | X | X | | |
| 22 | | Steps 20-21 (+reverse flow) | | | | | | | X |
| 23 | | Repeat steps 20-22x tm(s) | | | | | | | |
| 24 | Rinse | Empty circulation tank | | | | | | | |
| 25 | | Push & pull to acid tank | | X | | X | | | |
| 26 | | Partial rinse to circuit & pull | | | | | | | |
| 27 | | Push & pull to acid tank | | X | | X | | | |
| 28 | | Repeat steps 26-27x tm(s) | | | | | | | |
| 29 | Sanitizing | Partial sanitizer sol'n prep. | X | | | | | | |
| 30 | | Sol'n sent to circuit & pull | | | | | | | |
| 31 | | Push & pull to drain | | X | X | X | | | |
| 32 | | Push & pull (+reverse flow) | | X | X | X | | | X |
| 33 | | Final drain (all lines) | | | | | | | |

| Step | Phase | CHART 1 (PAGE 1) REFERENCE DRAWING 5 LINE WASH & SANITIZE PROGRAM USING THE PUSH & PULL METHOD STEP DESCRIPTION Item number | Suction return pump  38 | Aspirator/ blower fan  45 | Routing valve (normally open to 51)  46 | Routing valve to tank 1 (if off, or to pipe 49 when on)  47 | Routing valve to tank 1 (if off, to pipe 61 if on)  48 | Vacuum pump (also open valve 53)  54 | Routing valve (off = to drain, on = to any CIP tank)  55 |
|---|---|---|---|---|---|---|---|---|---|
| 0 | | Home | | | | | | | |
| 1 | Rec | Partial rinse to circuit & pull | X | | | | | | |
| 2 | | Push & pull to recovery silo | X | | | | | | |
| 3 | Rinse | Partial rinse to circuit & pull | X | | | | | | |
| 4 | | Push & pull to drain | X | | | | | | |
| 5 | | Do steps 3 & 4 (reverse flow) | | | | | | | |

TABLE 1A-continued

| Step | Phase | Step Description | Col A | Col B |
|---|---|---|---|---|
| 6 | | Repeat steps 3-5x time(s) | | |
| 7 | Caustic | Partial caustic sol'n to line | X | X |
| 8 | | Push & pull to circulation tk | X | X |
| 9 | | Partial caustic sol'n to line | X | X |
| 10 | | Push & pull to circulation tk | X | X |
| 11 | | Steps 9-10 (+reverse flow) | | |
| 12 | | Repeat steps 9-11x time(s) | | |
| 13 | Rinse | Empty circulation tank | X | X |
| 14 | | Push & pull to caustic tk | X | X |
| 15 | | Partial rinse to circuit & pull | X | X |
| 16 | | Push & pull to caustic tk | X | X |
| 17 | | Repeat steps 15-16x tm(s) | | |
| 18 | Acid | Partial acid sol'n to line | X | X |
| 19 | | Push & pull to circulation tk | X | X |
| 20 | | Partial acid sol'n to line | X | X |
| 21 | | Push & pull to circulation tk | X | X |
| 22 | | Steps 20-21 (+reverse flow) | | |
| 23 | | Repeat steps 20-22x tm(s) | | |
| 24 | Rinse | Empty circulation tank | X | X |
| 25 | | Push & pull to acid tank | X | X |
| 26 | | Partial rinse to circuit & pull | X | X |
| 27 | | Push & pull to acid tank | X | X |
| 28 | | Repeat steps 26-27x tm(s) | | |
| 29 | Sanitizing | Partial sanitizer sol'n prep. | | |
| 30 | | Sol'n sent to circuit & pull | | |
| 31 | | Push & pull to drain | X | |
| 32 | | Push & pull (+reverse flow) | X | |
| 33 | | Final drain (all lines) | X | X |

TABLE 1B

| Step | Phase | CHART 1 (PAGE 2) REFERENCE DRAWING 5 LINE WASH & SANITIZE PROGRAM USING THE PUSH & PULL METHOD STEP DESCRIPTION Item number | Step time or volume | Routing valve (open path from 51 to 49 when on) 56 | CIP drain valve (normally open to drain) 58 | Chemical injection port (add by conductivity or flow) 59 | Routing valve to recov. silo (also turn on valve 81) 62 | Fresh water tank outlet valve (also opens 63 if low level) 63 |
|---|---|---|---|---|---|---|---|---|
| 0 | | Home | | | | | | |
| 1 | Rec | Partial rinse to circuit & pull | | | | | X | |
| 2 | | Push & pull to recovery silo | | | | | X | |
| 3 | Rinse | Partial rinse to circuit & pull | | | X | | | |
| 4 | | Push & pull to drain | | | X | | | |
| 5 | | Do steps 3 & 4 (reverse flow) | | | | | | |
| 6 | | Repeat steps 3-5x time(s) | | | | | | |
| 7 | Caustic wash | Partial caustic sol'n to line | | X | X | | | |
| 8 | | Push & pull to circulation tk | | X | X | | | |
| 9 | | Partial caustic sol'n to line | | X | X | X | | |
| 10 | | Push & pull to circulation tk | | X | X | X | | |
| 11 | | Steps 9-10 (+reverse flow) | | | | | | |
| 12 | | Repeat steps 9-11x time(s) | | | | | | |
| 13 | Rinse | Empty circulation tank | | | | | | |
| 14 | | Push & pull to caustic tk | | | | | | |
| 15 | | Partial rinse to circuit & pull | | | | | | |
| 16 | | Push & pull to caustic tk | | | | | | |
| 17 | | Repeat steps 15-16x tm(s) | | | | | | |
| 18 | Acid wash | Partial acid sol'n to line | | X | X | | | |
| 19 | | Push & pull to circulation tk | | X | X | | | |
| 20 | | Partial acid sol'n to line | | X | X | X | | |
| 21 | | Push & pull to circulation tk | | X | X | X | | |
| 22 | | Steps 20-21 (+reverse flow) | | | | | | |
| 23 | | Repeat steps 20-22x tm(s) | | | | | | |
| 24 | Rinse | Empty circulation tank | | | | | | |
| 25 | | Push & pull to acid tank | | | | | | |
| 26 | | Partial rinse to circuit & pull | | | | | | |
| 27 | | Push & pull to acid tank | | | | | | |
| 28 | | Repeat steps 26-27x tm(s) | | | | | | |
| 29 | Sanitizing | Partial sanitizer sol'n prep. | | | | X | | X |
| 30 | | Sol'n sent to circuit & pull | | | | | | |
| 31 | | Push & pull to drain | | | | | | |
| 32 | | Push & pull (+reverse flow) | | | | | | |
| 33 | | Final drain (all lines) | | | X | | | |

TABLE 1B-continued

| Step | Phase | CHART 1 (PAGE 2) REFERENCE DRAWING 5 LINE WASH & SANITIZE PROGRAM USING THE PUSH & PULL METHOD STEP DESCRIPTION Item number | Chemical solution tanks blocking valve 64 | Caustic tank outlet valve 65 | Recovered rinse tank outlet valve 66 | Acid tank outlet valve (add water 63 at low level) 67 | Caustic tank return valve (switch to 70 at high level) 69 | Recov. rinse tank return valve (to drain at high level) 70 | Acid tank return valve (switch to drain if at high level) 71 |
|---|---|---|---|---|---|---|---|---|---|
| 0 |  | Home |  |  |  |  |  |  |  |
| 1 | Rec | Partial rinse to circuit & pull |  |  |  |  |  |  |  |
| 2 |  | Push & pull to recovery silo |  |  |  |  |  |  |  |
| 3 | Rinse | Partial rinse to circuit & pull | X |  | X |  |  |  |  |
| 4 |  | Push & pull to drain | X |  | X |  |  |  |  |
| 5 |  | Do steps 3 & 4 (reverse flow) |  |  |  |  |  |  |  |
| 6 |  | Repeat steps 3-5x time(s) |  |  |  |  |  |  |  |
| 7 | Caustic | Partial caustic sol'n to line | X | X |  |  |  |  |  |
| 8 | wash | Push & pull to circulation tk | X |  |  |  |  |  |  |
| 9 |  | Partial caustic sol'n to line | X |  |  |  |  |  |  |
| 10 |  | Push & pull to circulation tk | X |  |  |  |  |  |  |
| 11 |  | Steps 9-10 (+reverse flow) |  |  |  |  |  |  |  |
| 12 |  | Repeat steps 9-11x time(s) |  |  |  |  |  |  |  |
| 13 | Rinse | Empty circulation tank |  |  |  |  | X |  |  |
| 14 |  | Push & pull to caustic tk |  |  |  |  | X |  |  |
| 15 |  | Partial rinse to circuit & pull |  |  |  |  | X |  |  |
| 16 |  | Push & pull to caustic tk |  |  |  |  | X |  |  |
| 17 |  | Repeat steps 15-16x tm(s) |  |  |  |  |  |  |  |
| 18 | Acid | Partial acid sol'n to line | X |  |  |  |  |  |  |
| 19 | wash | Push & pull to circulation tk | X |  |  |  |  |  |  |
| 20 |  | Partial acid sol'n to line | X |  |  |  |  |  |  |
| 21 |  | Push & pull to circulation tk | X |  |  |  |  |  |  |
| 22 |  | Steps 20-21 (+reverse flow) |  |  |  |  |  |  |  |
| 23 |  | Repeat steps 20-22x tm(s) |  |  |  |  |  |  |  |
| 24 | Rinse | Empty circulation tank |  |  |  |  |  |  | X |
| 25 |  | Push & pull to acid tank |  |  |  |  |  |  | X |
| 26 |  | Partial rinse to circuit & pull |  |  |  |  |  |  | X |
| 27 |  | Push & pull to acid tank |  |  |  |  |  |  | X |
| 28 |  | Repeat steps 26-27x tm(s) |  |  |  |  |  |  |  |
| 29 | Sani- | Partial sanitizer sol'n prep. |  |  |  |  |  |  |  |
| 30 | tizing | Sol'n sent to circuit & pull |  |  |  |  |  |  |  |
| 31 |  | Push & pull to drain |  |  |  |  |  |  |  |
| 32 |  | Push & pull (+reverse flow) |  |  |  |  |  |  |  |
| 33 |  | Final drain (all lines) | X |  |  |  |  |  |  |

| Step | Phase | CHART 1 (PAGE 2) REFERENCE DRAWING 5 LINE WASH & SANITIZE PROGRAM USING THE PUSH & PULL METHOD STEP DESCRIPTION Item number | Spare 72 | Spare 73 | Aspirator/ blower fan 74 | Spare 75 | Spare 76 | Spare 77 | Spare 78 | Spare 79 | Spare 80 |
|---|---|---|---|---|---|---|---|---|---|---|---|
| 0 |  | Home |  |  |  |  |  |  |  |  |  |
| 1 | Rec | Partial rinse to circuit & pull |  |  |  |  |  |  |  |  |  |
| 2 |  | Push & pull to recovery silo |  |  |  |  |  |  |  |  |  |
| 3 | Rinse | Partial rinse to circuit & pull |  |  |  |  |  |  |  |  |  |
| 4 |  | Push & pull to drain |  |  |  |  |  |  |  |  |  |
| 5 |  | Do steps 3 & 4 (reverse flow) |  |  |  |  |  |  |  |  |  |
| 6 |  | Repeat steps 3-5x time(s) |  |  |  |  |  |  |  |  |  |
| 7 | Caustic | Partial caustic sol'n to line |  |  |  |  |  |  |  |  |  |
| 8 | wash | Push & pull to circulation tk |  |  |  |  |  |  |  |  |  |
| 9 |  | Partial caustic sol'n to line |  |  |  |  |  |  |  |  |  |
| 10 |  | Push & pull to circulation tk |  |  |  |  |  |  |  |  |  |
| 11 |  | Steps 9-10 (+reverse flow) |  |  |  |  |  |  |  |  |  |
| 12 |  | Repeat steps 9-11x time(s) |  |  |  |  |  |  |  |  |  |
| 13 | Rinse | Empty circulation tank |  |  |  |  |  |  |  |  |  |
| 14 |  | Push & pull to caustic tk |  |  |  |  |  |  |  |  |  |
| 15 |  | Partial rinse to circuit & pull |  |  |  |  |  |  |  |  |  |
| 16 |  | Push & pull to caustic tk |  |  |  |  |  |  |  |  |  |
| 17 |  | Repeat steps 15-16x tm(s) |  |  |  |  |  |  |  |  |  |
| 18 | Acid | Partial acid sol'n to line |  |  |  |  |  |  |  |  |  |
| 19 | wash | Push & pull to circulation tk |  |  |  |  |  |  |  |  |  |
| 20 |  | Partial acid sol'n to line |  |  |  |  |  |  |  |  |  |
| 21 |  | Push & pull to circulation tk |  |  |  |  |  |  |  |  |  |
| 22 |  | Steps 20-21 (+reverse flow) |  |  |  |  |  |  |  |  |  |
| 23 |  | Repeat steps 20-22x tm(s) |  |  |  |  |  |  |  |  |  |
| 24 | Rinse | Empty circulation tank |  |  |  |  |  |  |  |  |  |
| 25 |  | Push & pull to acid tank |  |  |  |  |  |  |  |  |  |

TABLE 1B-continued

| | | |
|---|---|---|
| 26 | | Partial rinse to circuit & pull |
| 27 | | Push & pull to acid tank |
| 28 | | Repeat steps 26-27x tm(s) |
| 29 | Sani- | Partial sanitizer sol'n prep. |
| 30 | tizing | Sol'n sent to circuit & pull |
| 31 | | Push & pull to drain |
| 32 | | Push & pull (+reverse flow) |
| 33 | | Final drain (all lines) |

TABLE 2A

| Step | Phase | CHART 2 (PAGE 1) REFERENCE DRAWING 5 LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS STEP DESCRIPTION Item number | Step time or volume | Circulation tk outlet valve - also open 3 in rinse low level 2 | CIP supply pump 6 | Aqueduc water valve 8 | Block & bleed aqueduc water valve 9 | Steam flow valve (also turn on steam shutt off valve 14) 15 | Routing valve from CIP to circuit 18 |
|---|---|---|---|---|---|---|---|---|---|
| 0 | | Home | | | | | | | |
| 1 | Rec | Partial rinse to circuit & pull | | | | X | X | | X |
| 2 | | Push & pull to recovery silo | | | | | | | |
| 3 | Rinse | Partial rinse to circuit & pull | | | X | | | | X |
| 4 | | Push & pull to drain | | | | | | | |
| 5 | | Steps 3 & 4 (+reverse flow) | | | | | | | |
| 6 | | Repeat steps 3-5x time(s) | | | | | | | |
| 7 | Caustic | Circuit pre heating | | | | | | | |
| 8 | | Pre heating (+reverse flow) | | | | | | | |
| 9 | | Foam caustic sol'n & pull | | | | | | | |
| 10 | | Foam (+reverse flow) | | | | | | | |
| 11 | | Pause | | | | | | | |
| 12 | Rinse | Partial rinse to circuit & pull | | | X | | | | X |
| 13 | | Push & pull to drain | | | | | | | |
| 14 | | Repeat steps 12-13x tm(s) | | | | | | | |
| 15 | Acid | Circuit pre heating | | | | | | | |
| 16 | | Pre heating (+reverse flow) | | | | | | | |
| 17 | | Foam acid sol'n & pull | | | | | | | |
| 18 | | Foam (+reverse flow) | | | | | | | |
| 19 | | Pause | | | | | | | |
| 20 | Rinse | Partial rinse to circuit & pull | | | X | | | | X |
| 21 | | Push & pull to drain | | | | | | | |
| 22 | | Repeat steps 20-21x tm(s) | | | | | | | |
| 23 | Sanitiz. | Atom. Sani. + push & pull | | | | | | | |
| 24 | | Atom. Sani. (+reverse flow) | | | | | | | |
| 25 | | Final drain (all lines) | | | X | | | | X |
| 26 | | | | | | | | | |
| 27 | | | | | | | | | |
| 28 | | | | | | | | | |
| 29 | | | | | | | | | |
| 30 | | | | | | | | | |
| 31 | | | | | | | | | |
| 32 | | | | | | | | | |
| 33 | | | | | | | | | |

| Step | Phase | CHART 2 (PAGE 1) REFERENCE DRAWING 5 LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS STEP DESCRIPTION Item number | Routing valve to circulation tank 1 20 | Chemical & com pressed gas main valve 23 | Atomized chemical valve (caustic or acid or sanitizer) 24 | Com- pressed gas valve 26 | Live steam valve (flow con- trolled) 27 | Flow restriction valve (normally open to circuit) 31 | Routing valves - also activate 35 (reverse flow valves) 32 |
|---|---|---|---|---|---|---|---|---|---|
| 0 | | Home | | | | | | | |
| 1 | Rec | Partial rinse to circuit & pull | | | | | | | |
| 2 | | Push & pull to recovery silo | | X | | X | | | |
| 3 | Rinse | Partial rinse to circuit & pull | | | | | | | |
| 4 | | Push & pull to drain | | X | | X | | | |
| 5 | | Steps 3 & 4 (+reverse flow) | | | | | | | X |

TABLE 2A-continued

| Step | Phase | Step description | Col 1 | Col 2 | Col 3 | Col 4 | Col 5 | Col 6 |
|---|---|---|---|---|---|---|---|---|
| 6 | | Repeat steps 3-5x time(s) | | | | | | |
| 7 | Caustic | Circuit pre heating | X | | | X | | |
| 8 | | Pre heating (+reverse flow) | X | | | X | | X |
| 9 | | Foam caustic sol'n & pull | X | X | X | X | X | |
| 10 | | Foam (+reverse flow) | X | X | X | X | X | X |
| 11 | | Pause | | | | | | |
| 12 | Rinse | Partial rinse to circuit & pull | | | | | | |
| 13 | | Push & pull to drain | X | | | X | | |
| 14 | | Repeat steps 12-13x tm(s) | | | | | | |
| 15 | Acid | Circuit pre heating | X | | | X | | |
| 16 | | Pre heating (+reverse flow) | X | | | X | | X |
| 17 | | Foam acid sol'n & pull | X | X | X | X | X | |
| 18 | | Foam (+reverse flow) | X | X | X | X | X | X |
| 19 | | Pause | | | | | | |
| 20 | Rinse | Partial rinse to circuit & pull | | | | | | |
| 21 | | Push & pull to drain | X | | | X | | |
| 22 | | Repeat steps 20-21x tm(s) | | | | | | |
| 23 | Sanitiz. | Atom. Sani. + push & pull | X | X | X | | | |
| 24 | | Atom. Sani. (+reverse flow) | X | X | X | | | X |
| 25 | | Final drain (all lines) | | | | | | |
| 26 | | | | | | | | |
| 27 | | | | | | | | |
| 28 | | | | | | | | |
| 29 | | | | | | | | |
| 30 | | | | | | | | |
| 31 | | | | | | | | |
| 32 | | | | | | | | |
| 33 | | | | | | | | |

CHART 2 (PAGE 1)
REFERENCE DRAWING 5
LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS

| Step | Phase | STEP DESCRIPTION Item number | Suction return pump 38 | Aspirator/ blower fan 45 | Routing valve (normally open to 51) 46 | Routing valve (open path to pipe 49 when on) 47 | Routing valve to tank 1 (if off, or to pipe 61 if on) 48 | Vacuum pump (also open valve 53) 54 | Routing valve (off = to drain, on = to any CIP tank) 55 |
|---|---|---|---|---|---|---|---|---|---|
| 0 | | Home | | | | | | | |
| 1 | Rec | Partial rinse to circuit & pull | X | | | | | | |
| 2 | | Push & pull to recovery silo | X | | | | | | |
| 3 | Rinse | Partial rinse to circuit & pull | X | | | | | | |
| 4 | | Push & pull to drain | X | | | | | | |
| 5 | | Steps 3 & 4 (+reverse flow) | | | | | | | |
| 6 | | Repeat steps 3-5x time(s) | | | | | | | |
| 7 | Caustic | Circuit pre heating | X | | | | | | |
| 8 | | Pre heating (+reverse flow) | X | | | | | | |
| 9 | | Foam caustic sol'n & pull | X | | | | | | |
| 10 | | Foam (+reverse flow) | X | | | | | | |
| 11 | | Pause | | | | | | | |
| 12 | Rinse | Partial rinse to circuit & pull | X | | | | | | |
| 13 | | Push & pull to drain | X | | | | | | |
| 14 | | Repeat steps 12-13x tm(s) | | | | | | | |
| 15 | Acid | Circuit pre heating | X | | | | | | |
| 16 | | Pre heating (+reverse flow) | X | | | | | | |
| 17 | | Foam acid sol'n & pull | X | | | | | | |
| 18 | | Foam (+reverse flow) | X | | | | | | |
| 19 | | Pause | | | | | | | |
| 20 | Rinse | Partial rinse to circuit & pull | X | | | | | | |
| 21 | | Push & pull to drain | X | | | | | | |
| 22 | | Repeat steps 20-21x tm(s) | | | | | | | |
| 23 | Sanitiz. | Atom. Sani. + push & pull | X | | | | | | |
| 24 | | Atom. Sani. (+reverse flow) | X | | | | | | |
| 25 | | Final drain (all lines) | | | | X | X | | |
| 26 | | | | | | | | | |
| 27 | | | | | | | | | |
| 28 | | | | | | | | | |
| 29 | | | | | | | | | |
| 30 | | | | | | | | | |
| 31 | | | | | | | | | |
| 32 | | | | | | | | | |
| 33 | | | | | | | | | |

TABLE 2B

| Step | Phase | CHART 2 (PAGE 2) REFERENCE DRAWING 5 LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS STEP DESCRIPTION Item number | Step time or volume | Routing valve (open path from 51 to 49 when on) 56 | CIP drain valve (normally open to drain) 58 | Chemical injection port (add by conductivity of flow) 59 | Routing valve to recov. silo (also turn on valve 81) 62 | Fresh water tank outlet valve 63 |
|---|---|---|---|---|---|---|---|---|
| 0 |  | Home |  |  |  |  |  |  |
| 1 | Rec | Partial rinse to circuit & pull |  |  |  |  | X |  |
| 2 |  | Push & pull to recovery silo |  |  |  |  | X |  |
| 3 | Rinse | Partial rinse to circuit & pull |  |  | X |  |  |  |
| 4 |  | Push & pull to drain |  |  | X |  |  |  |
| 5 |  | Steps 3 & 4 (+reverse flow) |  |  |  |  |  |  |
| 6 |  | Repeat steps 3-5x time(s) |  |  |  |  |  |  |
| 7 | Caustic | Circuit pre heating |  |  |  |  |  |  |
| 8 |  | Pre heating (+reverse flow) |  |  |  |  |  |  |
| 9 |  | Foam caustic sol'n & pull |  |  |  |  |  |  |
| 10 |  | Foam (+reverse flow) |  |  |  |  |  |  |
| 11 |  | Pause |  |  |  |  |  |  |
| 12 | Rinse | Partial rinse to circuit & pull |  |  |  |  |  | X |
| 13 |  | Push & pull to drain |  |  |  |  |  |  |
| 14 |  | Repeat steps 12-13x tm(s) |  |  |  |  |  |  |
| 15 | Acid | Circuit pre heating |  |  |  |  |  |  |
| 16 |  | Pre heating (+reverse flow) |  |  |  |  |  |  |
| 17 |  | Foam acid sol'n & pull |  |  |  |  |  |  |
| 18 |  | Foam (+reverse flow) |  |  |  |  |  |  |
| 19 |  | Pause |  |  |  |  |  |  |
| 20 | Rinse | Partial rinse to circuit & pull |  |  |  |  |  | X |
| 21 |  | Push & pull to drain |  |  |  |  |  |  |
| 22 |  | Repeat steps 20-21x tm(s) |  |  |  |  |  |  |
| 23 | Sanit. | Atom. Sani. + push & pull |  |  |  |  |  |  |
| 24 |  | Atom. Sani. (+reverse flow) |  |  |  |  |  |  |
| 25 |  | Final drain (all lines) |  |  | X |  |  |  |
| 26 |  |  |  |  |  |  |  |  |
| 27 |  |  |  |  |  |  |  |  |
| 28 |  |  |  |  |  |  |  |  |
| 29 |  |  |  |  |  |  |  |  |
| 30 |  |  |  |  |  |  |  |  |
| 31 |  |  |  |  |  |  |  |  |
| 32 |  |  |  |  |  |  |  |  |
| 33 |  |  |  |  |  |  |  |  |

| Step | Phase | CHART 2 (PAGE 2) REFERENCE DRAWING 5 LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS STEP DESCRIPTION Item number | Chemical solution tanks blocking valve 64 | Caustic tank outlet valve 65 | Recovered rinse tank outlet valve 66 | Acid tank outlet valve 67 | Caustic tank return valve (switch to 70 at high level) 69 | Recov. rinse tank return valve (to drain at high level) 70 | Acid tank return valve (switch to drain if at high level) 71 |
|---|---|---|---|---|---|---|---|---|---|
| 0 |  | Home |  |  |  |  |  |  |  |
| 1 | Rec | Partial rinse to circuit & pull |  |  |  |  |  |  |  |
| 2 |  | Push & pull to recovery silo |  |  |  |  |  |  |  |
| 3 | Rinse | Partial rinse to circuit & pull | X |  | X |  |  |  |  |
| 4 |  | Push & pull to drain | X |  | X |  |  |  |  |
| 5 |  | Steps 3 & 4 (+reverse flow) |  |  |  |  |  |  |  |
| 6 |  | Repeat steps 3-5x time(s) |  |  |  |  |  |  |  |
| 7 | Caustic | Circuit pre heating |  |  |  |  |  |  |  |
| 8 |  | Pre heating (+reverse flow) |  |  |  |  |  |  |  |
| 9 |  | Foam caustic sol'n & pull |  |  |  |  |  |  |  |
| 10 |  | Foam (+reverse flow) |  |  |  |  |  |  |  |
| 11 |  | Pause |  |  |  |  |  |  |  |
| 12 | Rinse | Partial rinse to circuit & pull |  |  |  |  |  |  |  |
| 13 |  | Push & pull to drain |  |  |  |  |  |  |  |
| 14 |  | Repeat steps 12-13x tm(s) |  |  |  |  |  |  |  |
| 15 | Acid | Circuit pre heating |  |  |  |  |  |  |  |
| 16 |  | Pre heating (+reverse flow) |  |  |  |  |  |  |  |

TABLE 2B-continued

| | | | | | | | | | | | |
|---|---|---|---|---|---|---|---|---|---|---|---|
| 17 | | Foam acid sol'n & pull | | | | | | | | | |
| 18 | | Foam (+reverse flow) | | | | | | | | | |
| 19 | | Pause | | | | | | | | | |
| 20 | Rinse | Partial rinse to circuit & pull | | | | | | | | | |
| 21 | | Push & pull to drain | | | | | | | | | |
| 22 | | Repeat steps 20-21x tm(s) | | | | | | | | | |
| 23 | Sanit. | Atom. Sani. + push & pull | | | | | | | | | |
| 24 | | Atom. Sani. (+reverse flow) | | | | | | | | | |
| 25 | | Final drain (all lines) | X | | | | | | | | |
| 26 | | | | | | | | | | | |
| 27 | | | | | | | | | | | |
| 28 | | | | | | | | | | | |
| 29 | | | | | | | | | | | |
| 30 | | | | | | | | | | | |
| 31 | | | | | | | | | | | |
| 32 | | | | | | | | | | | |
| 33 | | | | | | | | | | | |

| Step | Phase | CHART 2 (PAGE 2) REFERENCE DRAWING 5 LINE WASH & SANITIZE PROGRAM USING THE PUSH & PULL METHOD FOR THE RINSE STEPS & THE FOAMING METHOD FOR THE WASH STEPS & THE CHEMICAL ATOMIZING METHOD FOR THE SANITIZE STEPS STEP DESCRIPTION Item number | Spare 72 | Spare 73 | Aspirator/ blower fan 74 | Spare 75 | Spare 76 | Spare 77 | Spare 78 | Spare 79 | Spare 80 |
|---|---|---|---|---|---|---|---|---|---|---|---|
| 0 | | Home | | | | | | | | | |
| 1 | Rec | Partial rinse to circuit & pull | | | | | | | | | |
| 2 | | Push & pull to recovery silo | | | | | | | | | |
| 3 | Rinse | Partial rinse to circuit & pull | | | | | | | | | |
| 4 | | Push & pull to drain | | | | | | | | | |
| 5 | | Steps 3 & 4 (+reverse flow) | | | | | | | | | |
| 6 | | Repeat steps 3-5x time(s) | | | | | | | | | |
| 7 | Caustic | Circuit pre heating | | | | | | | | | |
| 8 | | Pre heating (+reverse flow) | | | | | | | | | |
| 9 | | Foam caustic sol'n & pull | | | | | | | | | |
| 10 | | Foam (+reverse flow) | | | | | | | | | |
| 11 | | Pause | | | | | | | | | |
| 12 | Rinse | Partial rinse to circuit & pull | | | | | | | | | |
| 13 | | Push & pull to drain | | | | | | | | | |
| 14 | | Repeat steps 12-13x tm(s) | | | | | | | | | |
| 15 | Acid | Circuit pre heating | | | | | | | | | |
| 16 | | Pre heating (+reverse flow) | | | | | | | | | |
| 17 | | Foam acid sol'n & pull | | | | | | | | | |
| 18 | | Foam (+reverse flow) | | | | | | | | | |
| 19 | | Pause | | | | | | | | | |
| 20 | Rinse | Partial rinse to circuit & pull | | | | | | | | | |
| 21 | | Push & pull to drain | | | | | | | | | |
| 22 | | Repeat steps 20-21x tm(s) | | | | | | | | | |
| 23 | Sanit. | Atom. Sani. + push & pull | | | | | | | | | |
| 24 | | Atom. Sani. (+reverse flow) | | | | | | | | | |
| 25 | | Final drain (all lines) | | | | | | | | | |
| 26 | | | | | | | | | | | |
| 27 | | | | | | | | | | | |
| 28 | | | | | | | | | | | |
| 29 | | | | | | | | | | | |
| 30 | | | | | | | | | | | |
| 31 | | | | | | | | | | | |
| 32 | | | | | | | | | | | |
| 33 | | | | | | | | | | | |

TABLE 3A

CHART 3 (PAGE 1)
REFERENCE DRAWING 5
LINE WASH & SANITIZE
PROGRAM USING THE
PUSH & PULL METHOD
FOR THE RINSE STEPS &
THE ATOMIZING METHOD
FOR THE WASH &                    Circulation TABLE 3A-continued

| Step | Phase | SANITIZE STEPS (CHEMICAL ATOMIZATION IS FOLLOWED BY CIRCULATION OF THE ATOMIZED SOLUTION) STEP DESCRIPTION Item number | Step time or volume | tk outlet valve - also open 3 in rinse low level 2 | CIP supply pump 6 | Aqueduc water valve 8 | Block & bleed aqueduc water valve 9 | Steam modulating valve (set point controlled by RTD) 15 | Routing valve from CIP to circuit 18 |
|---|---|---|---|---|---|---|---|---|---|
| 0 | | Home | | | | | | | |
| 1 | Rec | Partial rinse to circuit & pull | | | | X | X | | X |
| 2 | | Push & pull to recovery silo | | | | | | | |
| 3 | Rinse | Partial rinse to circuit & pull | | | X | | | | X |
| 4 | | Push & pull to drain | | | | | | | |
| 5 | | Do steps 3-4 (+reverse flow) | | | | | | | |
| 6 | | Repeat steps 3-5x time(s) | | | | | | | |
| 7 | Caustic | Partial caustic sol'n to line | | | X | | | X | X |
| 8 | | Push & pull to caustic tank | | X | | | | | |
| 9 | | Push & pull + atom. caust. | | | | | | | |
| 10 | | Push & pull + atom + rev. flow | | | | | | | |
| 11 | | Circulation of atomized sol'n | | | X | | | | X |
| 12 | | Circulation with reverse flow | | | X | | | | X |
| 13 | | Repeat steps 9-12x time(s) | | | | | | | |
| 14 | Rinse | Partial rinse to circuit & pull | | | X | | | | X |
| 15 | | Push & pull to caustic tank | | | | | | | |
| 16 | | Repeat steps 14-15x time(s) | | | | | | | |
| 17 | Acid | Partial acid sol'n to line | | | X | | | X | X |
| 18 | | Push & pull to acid tank | | X | | | | | |
| 19 | | Push & pull + atomized acid | | | | | | | |
| 20 | | Push & pull + atom + rev. flow | | | | | | | |
| 21 | | Circulation of atomized sol'n | | | X | | | | X |
| 22 | | Circulation with reverse flow | | | X | | | | X |
| 23 | | Repeat steps 19-22x time(s) | | | | | | | |
| 24 | Rinse | Partial rinse to circuit & pull | | | X | | | | X |
| 25 | | Push & pull to acid tank | | | | | | | |
| 26 | | Repeat steps 25-26x time(s) | | | | | | | |
| 27 | Sanitizer | Atom. sani. push & pull | | X | | | | | |
| 28 | | Atom. push & pull + rev. flow | | | | | | | |
| 29 | | Circulation atom. sani sol'n | | | X | | | | X |
| 30 | | Circulation with reverse flow | | | X | | | | X |
| 31 | | Final drain (all lines) | | | X | | | | X |
| 32 | | | | | | | | | |
| 33 | | | | | | | | | |

| Step | Phase | CHART 3 (PAGE 1) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY CIRCULATION OF THE ATOMIZED SOLUTION) STEP DESCRIPTION Item number | Routing valve to circulation tank 1 20 | Chemical & compressed gas main valve 23 | Atomized chemical valve (caustic or acid or sanitizer) 24 | Compressed gas valve 26 | Live steam valve (flow controlled) 27 | Flow restriction valve (normally open to circuit) 31 | Routing valves - also activate 35 (reverse flow valves) 32 |
|---|---|---|---|---|---|---|---|---|---|
| 0 | | Home | | | | | | | |
| 1 | Rec | Partial rinse to circuit & pull | | | | | | | |
| 2 | | Push & pull to recovery silo | | X | | X | | | |
| 3 | Rinse | Partial rinse to circuit & pull | | | | | | | |
| 4 | | Push & pull to drain | | X | | X | | | |
| 5 | | Do steps 3-4 (+reverse flow) | | | | | | | X |
| 6 | | Repeat steps 3-5x time(s) | | | | | | | |
| 7 | Caustic | Partial caustic sol'n to line | | | | | | | |
| 8 | | Push & pull to caustic tank | | X | X | X | X | | |
| 9 | | Push & pull + atom. caust. | | X | X | X | X | | |
| 10 | | Push & pull + atom + rev. flow | | X | X | X | X | | X |
| 11 | | Circulation of atomized sol'n | | X | | | X | | |
| 12 | | Circulation with reverse flow | | X | | | X | | X |
| 13 | | Repeat steps 9-12x time(s) | | | | | | | |
| 14 | Rinse | Partial rinse to circuit & pull | | | | | | | |
| 15 | | Push & pull to caustic tank | | X | | X | | | |
| 16 | | Repeat steps 14-15x time(s) | | | | | | | |
| 17 | Acid | Partial acid sol'n to line | | | | | | | |
| 18 | | Push & pull to acid tank | | X | X | X | X | | |
| 19 | | Push & pull + atomized acid | | X | X | X | X | | |
| 20 | | Push & pull + atom + rev. flow | | X | X | X | X | | X |

TABLE 3A-continued

| Step | Phase | Description | | | | | |
|---|---|---|---|---|---|---|---|
| 21 | | Circulation of atomized sol'n | X | | X | | |
| 22 | | Circulation with reverse flow | X | | X | | X |
| 23 | | Repeat steps 19-22x time(s) | | | | | |
| 24 | Rinse | Partial rinse to circuit & pull | | | | | |
| 25 | | Push & pull to acid tank | X | | X | | |
| 26 | | Repeat steps 25-26x time(s) | | | | | |
| 27 | Sanitizer | Atom. sani. push & pull | X | X | X | | |
| 28 | | Atom. push & pull + rev. flow | X | X | X | | X |
| 29 | | Circulation atom. sani sol'n | | | | X | |
| 30 | | Circulation with reverse flow | | | | X | X |
| 31 | | Final drain (all lines) | | | | | |
| 32 | | | | | | | |
| 33 | | | | | | | |

CHART 3 (PAGE 1)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY CIRCULATION OF THE ATOMIZED SOLUTION)

| Step | Phase | Step Description / Item number | Suction return pump 38 | Aspirator/ blower fan 45 | Routing valve (normally open to 51) 46 | Routing valve (open path to pipe 49 when on) 47 | Routing valve to tank 1 (if off, or to pipe 61 if on) 48 | Vacuum pump (also open valve 53) 54 | Routing valve (off = to drain, on = to any CIP tank) 55 |
|---|---|---|---|---|---|---|---|---|---|
| 0 | | Home | | | | | | | |
| 1 | Rec | Partial rinse to circuit & pull | X | | | | | | |
| 2 | | Push & pull to recovery silo | X | | | | | | |
| 3 | Rinse | Partial rinse to circuit & pull | X | | | | | | |
| 4 | | Push & pull to drain | X | | | | | | |
| 5 | | Do steps 3-4 (+reverse flow) | | | | | | | |
| 6 | | Repeat steps 3-5x time(s) | | | | | | | |
| 7 | Caustic | Partial caustic sol'n to line | X | | | | | | X |
| 8 | | Push & pull to caustic tank | X | | | | | | X |
| 9 | | Push & pull + atom. caust. | X | | | | X | | X |
| 10 | | Push & pull + atom + rev. flow | X | | | | | | X |
| 11 | | Circulation of atomized sol'n | X | X | X | X | X | | X |
| 12 | | Circulation with reverse flow | X | X | X | X | X | | X |
| 13 | | Repeat steps 9-12x time(s) | | | | | | | |
| 14 | Rinse | Partial rinse to circuit & pull | X | | | | | | X |
| 15 | | Push & pull to caustic tank | X | | | | | | X |
| 16 | | Repeat steps 14-15x time(s) | | | | | | | |
| 17 | Acid | Partial acid sol'n to line | X | | | | | | X |
| 18 | | Push & pull to acid tank | X | | | | X | | X |
| 19 | | Push & pull + atomized acid | X | | | | | | X |
| 20 | | Push & pull + atom + rev. flow | X | | | | | | X |
| 21 | | Circulation of atomized sol'n | X | X | X | X | X | | X |
| 22 | | Circulation with reverse flow | X | X | X | X | X | | X |
| 23 | | Repeat steps 19-22x time(s) | | | | | | | |
| 24 | Rinse | Partial rinse to circuit & pull | X | | | | | | X |
| 25 | | Push & pull to acid tank | X | | | | | | X |
| 26 | | Repeat steps 25-26x time(s) | | | | | | | |
| 27 | Sanitizer | Atom. sani. push & pull | X | | | | X | | |
| 28 | | Atom. push & pull + rev. flow | X | | | | | | |
| 29 | | Circulation atom. sani sol'n | X | X | X | X | X | | |
| 30 | | Circulation with reverse flow | X | X | X | X | X | | |
| 31 | | Final drain (all lines) | | | | X | X | | |
| 32 | | | | | | | | | |
| 33 | | | | | | | | | |

TABLE 3B

CHART 3 (PAGE 2)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION

| | Routing valve (open path | CIP drain | Chemical injection port | Routing valve to recov. | Fresh | Chemical |
|---|---|---|---|---|---|---|

TABLE 3B-continued

| Step | Phase | IS FOLLOWED BY CIRCULATION OF THE ATOMIZED SOLUTION) STEP DES

TABLE 3B-continued

| Step | Phase | Item number | Spare 72 | Spare 73 | Aspirator/blower fan 74 | Spare 75 | Spare 76 | Spare 77 | Spare 78 | Spare 79 | Spare 80 |
|---|---|---|---|---|---|---|---|---|---|---|---|
| 23 | | Repeat steps 19-22x time(s) | | | | | | | | | |
| 24 | Rinse | Partial rinse to circuit & pull | | | | | | | | | X |
| 25 | | Push & pull to acid tank | | | | | | | | | X |
| 26 | | Repeat steps 25-26x time(s) | | | | | | | | | |
| 27 | Sanitizer | Atom. sani. push & pull | | | | | | | | | |
| 28 | | Atom. push & pull + rev. flow | | | | | | | | | |
| 29 | | Circulation atom. sani sol'n | | | | | | | | | |
| 30 | | Circulation with reverse flow | | | | | | | | | |
| 31 | | Final drain (all lines) | | | | | | | | | |
| 32 | | | | | | | | | | | |
| 33 | | | | | | | | | | | |

CHART 3 (PAGE 2)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY CIRCULATION OF THE ATOMIZED SOLUTION)

| Step | Phase | STEP DESCRIPTION Item number | Spare 72 | Spare 73 | Aspirator/blower fan 74 | Spare 75 | Spare 76 | Spare 77 | Spare 78 | Spare 79 | Spare 80 |
|---|---|---|---|---|---|---|---|---|---|---|---|
| 0 | | Home | | | | | | | | | |
| 1 | Rec | Partial rinse to circuit & pull | | | | | | | | | |
| 2 | | Push & pull to recovery silo | | | | | | | | | |
| 3 | Rinse | Partial rinse to circuit & pull | | | | | | | | | |
| 4 | | Push & pull to drain | | | | | | | | | |
| 5 | | Do steps 3-4 (+reverse flow) | | | | | | | | | |
| 6 | | Repeat steps 3-5x time(s) | | | | | | | | | |
| 7 | Caustic | Partial caustic sol'n to line | | | | | | | | | |
| 8 | | Push & pull to caustic tank | | | | | | | | | |
| 9 | | Push & pull + atom. caust. | | | | | | | | | |
| 10 | | Push & pull + atom + rev. flow | | | | | | | | | |
| 11 | | Circulation of atomized sol'n | | | X | | | | | | |
| 12 | | Circulation with reverse flow | | | X | | | | | | |
| 13 | | Repeat steps 9-12x time(s) | | | | | | | | | |
| 14 | Rinse | Partial rinse to circuit & pull | | | | | | | | | |
| 15 | | Push & pull to caustic tank | | | | | | | | | |
| 16 | | Repeat steps 14-15x time(s) | | | | | | | | | |
| 17 | Acid | Partial acid sol'n to line | | | | | | | | | |
| 18 | | Push & pull to acid tank | | | | | | | | | |
| 19 | | Push & pull + atomized acid | | | | | | | | | |
| 20 | | Push & pull + atom + rev. flow | | | | | | | | | |
| 21 | | Circulation of atomized sol'n | | | X | | | | | | |
| 22 | | Circulation with reverse flow | | | X | | | | | | |
| 23 | | Repeat steps 19-22x time(s) | | | | | | | | | |
| 24 | Rinse | Partial rinse to circuit & pull | | | | | | | | | |
| 25 | | Push & pull to acid tank | | | | | | | | | |
| 26 | | Repeat steps 25-26x time(s) | | | | | | | | | |
| 27 | Sanitizer | Atom. sani. push & pull | | | | | | | | | |
| 28 | | Atom. push & pull + rev. flow | | | | | | | | | |
| 29 | | Circulation atom. sani sol'n | | | X | | | | | | |
| 30 | | Circulation with reverse flow | | | X | | | | | | |
| 31 | | Final drain (all lines) | | | | | | | | | |
| 32 | | | | | | | | | | | |
| 33 | | | | | | | | | | | |

TABLE 4A

CHART 4 (PAGE 1)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE

| | Circulation tk outlet valve - also open | | Block & bleed | Steam modulating valve | Routing valve |
|---|---|---|---|---|---|

TABLE 4A-continued

| Step | Phase | CIRCUIT FOLLOWED BY DEPRESSURIZATION) STEP DESCRIPTION Item number | Step time or volume | 3 in rinse low level 2 | CIP supply pump 6 | Aqueduc water valve 8 | aqueduc water valve 9 | (set point controlled by RTD) 15 | from CIP to circuit 18 |
|---|---|---|---|---|---|---|---|---|---|
| 0 | | Home | | | | | | | |
| 1 | Rec | Partial rinse to circuit & pull | | | | X | X | | X |
| 2 | | Push & pull to recovery silo | | | | | | | |
| 3 | Rinse | Partial rinse to circuit & pull | | | X | | | | X |
| 4 | | Push & pull to drain | | | | | | | |
| 5 | | Do steps 3-4 (reverse flow) | | | | | | | |
| 6 | | Repeat steps 3-5x time(s) | | | | | | | |
| 7 | Caustic | Partial caustic sol'n to circuit | | | X | | | X | X |
| 8 | | Push & pull + atom. caust. | | | | | | | |
| 9 | | Push + atom + pressurization | | | | | | | |
| 10 | | Depress. + atom + push & pull | | | | | | | |
| 11 | | Repeat steps 9-10x time(s) | | | | | | | |
| 12 | Rinse | Empty circulation tank | | X | X | | | | X |
| 13 | | Push & pull to caustic tank | | | | | | | |
| 14 | | Partial rinse to circuit & pull | | X | X | | | | X |
| 15 | | Push & pull to caustic tank | | | | | | | |
| 16 | | Repeat steps 14-15x time(s) | | | | | | | |
| 17 | Acid | Partial acid sol'n to circuit | | | X | | | X | X |
| 18 | | Push & pull + atom. acid | | | | X | | | |
| 19 | | Push + atom + pressurization | | | | | | | |
| 20 | | Depress. + atom. push & pull | | | | | | | |
| 21 | | Repeat steps 19-20x time(s) | | | | | | | |
| 22 | Rinse | Empty circulation tank | | X | X | | | | X |
| 23 | | Push & pull to acid tank | | | | | | | |
| 24 | | Partial rinse & pull to acid tk | | X | X | | | | X |
| 25 | | Push & pull to acid tank | | | | | | | |
| 26 | | Repeat steps 24-25x time(s) | | | | | | | |
| 27 | Sanitizer | Push + atom. sani & pressur. | | | | | | | |
| 28 | | Push + atom sani & depress. | | | | | | | |
| 29 | | Repeat steps 27-28x time(s) | | | | | | | |
| 30 | | Final drain (all lines) | | | | X | | | X |
| 31 | | | | | | | | | |
| 32 | | | | | | | | | |
| 33 | | | | | | | | | |

| Step | Phase | CHART 4 (PAGE 1) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION) STEP DESCRIPTION Item number | Routing valve to circulation tank 1 20 | Chemical & compressed gas main valve 23 | Atomized chemical valve (caustic or acid or sanitizer) 24 | Compressed gas valve 26 | Live steam valve (flow controlled) 27 | Flow restriction valve (normally open to circuit) 31 | Routing valves - also activate 35 (reverse flow valves) 32 |
|---|---|---|---|---|---|---|---|---|---|
| 0 | | Home | | | | | | | |
| 1 | Rec | Partial rinse to circuit & pull | | | | | | | |
| 2 | | Push & pull to recovery silo | | X | | X | | | |
| 3 | Rinse | Partial rinse to circuit & pull | | | | | | | |
| 4 | | Push & pull to drain | | X | | X | | | |
| 5 | | Do steps 3-4 (reverse flow) | | | | | | | |
| 6 | | Repeat steps 3-5x time(s) | | | | | | | |
| 7 | Caustic | Partial caustic sol'n to circuit | | | | | | | |
| 8 | | Push & pull + atom. caust. | | X | X | X | X | | |
| 9 | | Push + atom + pressurization | | X | X | X | X | | |
| 10 | | Depress. + atom + push & pull | | X | X | X | X | | |
| 11 | | Repeat steps 9-10x time(s) | | | | | | | |
| 12 | Rinse | Empty circulation tank | | | | | | | |
| 13 | | Push & pull to caustic tank | | X | | X | | | |
| 14 | | Partial rinse to circuit & pull | | | | | | | |
| 15 | | Push & pull to caustic tank | | X | | X | | | |
| 16 | | Repeat steps 14-15x time(s) | | | | | | | |
| 17 | Acid | Partial acid sol'n to circuit | | | | | | | |
| 18 | | Push & pull + atom. acid | | X | X | X | X | | |
| 19 | | Push + atom + pressurization | | X | X | X | X | | |
| 20 | | Depress. + atom. push & pull | | X | X | X | X | | |
| 21 | | Repeat steps 19-20x time(s) | | | | | | | |
| 22 | Rinse | Empty circulation tank | | | | | | | |

TABLE 4A-continued

| Step | Phase | Item number | | | |
|---|---|---|---|---|---|
| 23 | | Push & pull to acid tank | X | | X |
| 24 | | Partial rinse & pull to acid tk | | | |
| 25 | | Push & pull to acid tank | X | | X |
| 26 | | Repeat steps 24-25x time(s) | X | | X |
| 27 | Sanitizer | Push + atom. sani & pressur. | X | X | X |
| 28 | | Push + atom sani & depress. | X | X | X |
| 29 | | Repeat steps 27-28x time(s) | | | |
| 30 | | Final drain (all lines) | | | |
| 31 | | | | | |
| 32 | | | | | |
| 33 | | | | | |

CHART 4 (PAGE 1)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS
(CHEMICAL ATOMIZATION IS DONE WITH PRESSURIZATION OF THE CIRCUIT FOLLOWED BY DEPRESSURIZATION)
STEP DESCRIPTION

| Step | Phase | Item number | Suction return pump 38 | Aspirator/ blower fan 45 | Routing valve (normally open to 51) 46 | Routing valve (open path to pipe 49 when on) 47 | Routing valve to tank 1 (if off, or to pipe 61 if on) 48 | Vacuum pump (also open valve 53) 54 | Routing valve (off = to drain, on = to any CIP tank) 55 |
|---|---|---|---|---|---|---|---|---|---|
| 0 | | Home | | | | | | | |
| 1 | Rec | Partial rinse to circuit & pull | X | | | | | | |
| 2 | | Push & pull to recovery silo | X | | | | | | |
| 3 | Rinse | Partial rinse to circuit & pull | X | | | | | | |
| 4 | | Push & pull to drain | X | | | | | | |
| 5 | | Do steps 3-4 (reverse flow) | | | | | | | |
| 6 | | Repeat steps 3-5x time(s) | | | | | | | |
| 7 | Caustic | Partial caustic sol'n to circuit | X | | | | | | X |
| 8 | | Push & pull + atom. caust. | X | | | | | | X |
| 9 | | Push + atom + pressurization | X | | | X | | | X |
| 10 | | Depress. + atom + push & pull | X | | | | | | X |
| 11 | | Repeat steps 9-10x time(s) | | | | | | | |
| 12 | Rinse | Empty circulation tank | X | | | | | | X |
| 13 | | Push & pull to caustic tank | X | | | | | | X |
| 14 | | Partial rinse to circuit & pull | X | | | | | | X |
| 15 | | Push & pull to caustic tank | X | | | | | | X |
| 16 | | Repeat steps 14-15x time(s) | | | | | | | |
| 17 | Acid | Partial acid sol'n to circuit | X | | | | | | X |
| 18 | | Push & pull + atom. acid | X | | | | | | X |
| 19 | | Push + atom + pressurization | X | | | X | | | X |
| 20 | | Depress. + atom. push & pull | X | | | | | | X |
| 21 | | Repeat steps 19-20x time(s) | | | | | | | |
| 22 | Rinse | Empty circulation tank | X | | | | | | X |
| 23 | | Push & pull to acid tank | X | | | | | | X |
| 24 | | Partial rinse & pull to acid tk | X | | | | | | X |
| 25 | | Push & pull to acid tank | X | | | | | | X |
| 26 | | Repeat steps 24-25x time(s) | X | | | | | | X |
| 27 | Sanitizer | Push + atom. sani & pressur. | X | | | X | | | |
| 28 | | Push + atom sani & depress. | X | | | | | | |
| 29 | | Repeat steps 27-28x time(s) | | | | | | | |
| 30 | | Final drain (all lines) | | | | | X | X | |
| 31 | | | | | | | | | |
| 32 | | | | | | | | | |
| 33 | | | | | | | | | |

TABLE 4B

CHART 4 (PAGE 2)
REFERENCE DRAWING 5
LINE WASH & SANITIZE PROGRAM USING THE PUSH & PULL METHOD FOR THE RINSE STEPS & THE ATOMIZING METHOD FOR THE WASH & SANITIZE STEPS
(CHEMICAL ATOMIZATION IS DONE WITH

| | Routing valve (open | CIP drain | Chemical injection port | Routing valve to recov. silo | Fresh |
|---|---|---|---|---|---|

TABLE 4B-continued

| Step | Phase | Item number | Step time or volume | path from 51 to 49 when on 56 | valve (normally open to drain) 58 | (add by conductivity or flow) 59 | (also turn on valve 81) 62 | water tank outlet valve 63 |
|---|---|---|---|---|---|---|---|---|
| | | PRESSURIZATION OF THE CIRCUIT FOLLOWED BY DEPRESSURIZATION) STEP DESCRIPTION | | | | | | |
| 0 | | Home | | | | | | |
| 1 | Rec | Partial rinse to circuit & pull | | | | | X | |
| 2 | | Push & pull to recovery silo | | | | | X | |
| 3 | Rinse | Partial rinse to circuit & pull | | | X | | | |
| 4 | | Push & pull to drain | | | X | | | |
| 5 | | Do steps 3-4 (reverse flow) | | | | | | |
| 6 | | Repeat steps 3-5x time(s) | | | | | | |
| 7 | Caustic | Partial caustic sol'n to circuit | | X | X | | | |
| 8 | | Push & pull + atom. caust. | | X | | | | |
| 9 | | Push + atom + pressurization | | X | | | | |
| 10 | | Depress. + atom + push & pull | | X | | | | |
| 11 | | Repeat steps 9-10x time(s) | | | | | | |
| 12 | Rinse | Empty circulation tank | | | | | | |
| 13 | | Push & pull to caustic tank | | | | | | |
| 14 | | Partial rinse to circuit & pull | | | | | | |
| 15 | | Push & pull to caustic tank | | | | | | |
| 16 | | Repeat steps 14-15x time(s) | | | | | | |
| 17 | Acid | Partial acid sol'n to circuit | | X | X | | | |
| 18 | | Push & pull + atom. acid | | X | | | | |
| 19 | | Push + atom + pressurization | | X | | | | |
| 20 | | Depress. + atom. push & pull | | X | | | | |
| 21 | | Repeat steps 19-20x time(s) | | | | | | |
| 22 | Rinse | Empty circulation tank | | | | | | |
| 23 | | Push & pull to acid tank | | | | | | |
| 24 | | Partial rinse & pull to acid tk | | | | | | |
| 25 | | Push & pull to acid tank | | | | | | |
| 26 | | Repeat steps 24-25x time(s) | | | | | | |
| 27 | Sanitizer | Push + atom. sani & pressur. | | | | | | |
| 28 | | Push + atom sani & depress. | | | | | | |
| 29 | | Repeat steps 27-28x time(s) | | | | | | |
| 30 | | Final drain (all lines) | | X | | | | |
| 31 | | | | | | | | |
| 32 | | | | | | | | |
| 33 | | | | | | | | |

| Step | Phase | Item number | Chemical solution tanks blocking valve 64 | Caustic tank outlet valve 65 | Recovered rinse tank outlet valve 66 | Acid tank outlet valve 67 | Caustic tank return valve (switch to 70 at high level) 69 | Recov. rinse tank return valve (to drain at high level) 70 | Acid tank return valve (switch to drain if at high level) 71 |
|---|---|---|---|---|---|---|---|---|---|
| | | CHART 4 (PAGE 2) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION) STEP DESCRIPTION | | | | | | | |
| 0 | | Home | | | | | | | |
| 1 | Rec | Partial rinse to circuit & pull | | | | | | | |
| 2 | | Push & pull to recovery silo | | | | | | | |
| 3 | Rinse | Partial rinse to circuit & pull | X | | X | | | | |
| 4 | | Push & pull to drain | X | | X | | | | |
| 5 | | Do steps 3-4 (reverse flow) | | | | | | | |
| 6 | | Repeat steps 3-5x time(s) | | | | | | | |
| 7 | Caustic | Partial caustic sol'n to circuit | X | X | | | | | |
| 8 | | Push & pull + atom. caust. | | | | | | | |
| 9 | | Push + atom + pressurization | | | | | | | |
| 10 | | Depress. + atom + push & pull | | | | | | | |
| 11 | | Repeat steps 9-10x time(s) | | | | | | | |
| 12 | Rinse | Empty circulation tank | | | | | X | | |
| 13 | | Push & pull to caustic tank | | | | | X | | |
| 14 | | Partial rinse to circuit & pull | | | | | X | | |
| 15 | | Push & pull to caustic tank | | | | | X | | |
| 16 | | Repeat steps 14-15x time(s) | | | | | | | |
| 17 | Acid | Partial acid sol'n to circuit | X | | | X | | | |
| 18 | | Push & pull + atom. acid | X | | | | | | |
| 19 | | Push + atom + pressurization | | | | | | | |
| 20 | | Depress. + atom. push & pull | | | | | | | |
| 21 | | Repeat steps 19-20x time(s) | | | | | | | |

TABLE 4B-continued

| Step | Phase | Step Description | | | | | | | | | |
|---|---|---|---|---|---|---|---|---|---|---|---|
| 22 | Rinse | Empty circulation tank | | | | | | | | | X |
| 23 | | Push & pull to acid tank | | | | | | | | | X |
| 24 | | Partial rinse & pull to acid tk | | | | | | | | | X |
| 25 | | Push & pull to acid tank | | | | | | | | | X |
| 26 | | Repeat steps 24-25x time(s) | | | | | | | | | X |
| 27 | Sanitizer | Push + atom. sani & pressur. | | | | | | | | | |
| 28 | | Push + atom sani & depress. | | | | | | | | | |
| 29 | | Repeat steps 27-28x time(s) | | | | | | | | | |
| 30 | | Final drain (all lines) | X | | | | | | | | |
| 31 | | | | | | | | | | | |
| 32 | | | | | | | | | | | |
| 33 | | | | | | | | | | | |

CHART 4 (PAGE 2) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION)

| Step | Phase | Step Description Item number | Spare 72 | Spare 73 | Aspirator/blower fan 74 | Spare 75 | Spare 76 | Spare 77 | Spare 78 | Spare 79 | Spare 80 |
|---|---|---|---|---|---|---|---|---|---|---|---|
| 0 | | Home | | | | | | | | | |
| 1 | Rec | Partial rinse to circuit & pull | | | | | | | | | |
| 2 | | Push & pull to recovery silo | | | | | | | | | |
| 3 | Rinse | Partial rinse to circuit & pull | | | | | | | | | |
| 4 | | Push & pull to drain | | | | | | | | | |
| 5 | | Do steps 3-4 (reverse flow) | | | | | | | | | |
| 6 | | Repeat steps 3-5x time(s) | | | | | | | | | |
| 7 | Caustic | Partial caustic sol'n to circuit | | | | | | | | | |
| 8 | | Push & pull + atom. caust. | | | | | | | | | |
| 9 | | Push + atom + pressurization | | | | | | | | | |
| 10 | | Depress. + atom + push & pull | | | | | | | | | |
| 11 | | Repeat steps 9-10x time(s) | | | | | | | | | |
| 12 | Rinse | Empty circulation tank | | | | | | | | | |
| 13 | | Push & pull to caustic tank | | | | | | | | | |
| 14 | | Partial rinse to circuit & pull | | | | | | | | | |
| 15 | | Push & pull to caustic tank | | | | | | | | | |
| 16 | | Repeat steps 14-15x time(s) | | | | | | | | | |
| 17 | Acid | Partial acid sol'n to circuit | | | | | | | | | |
| 18 | | Push & pull + atom. acid | | | | | | | | | |
| 19 | | Push + atom + pressurization | | | | | | | | | |
| 20 | | Depress. + atom. push & pull | | | | | | | | | |
| 21 | | Repeat steps 19-20x time(s) | | | | | | | | | |
| 22 | Rinse | Empty circulation tank | | | | | | | | | |
| 23 | | Push & pull to acid tank | | | | | | | | | |
| 24 | | Partial rinse & pull to acid tk | | | | | | | | | |
| 25 | | Push & pull to acid tank | | | | | | | | | |
| 26 | | Repeat steps 24-25x time(s) | | | | | | | | | |
| 27 | Sanitizer | Push + atom. sani & pressur. | | | | | | | | | |
| 28 | | Push + atom sani & depress. | | | | | | | | | |
| 29 | | Repeat steps 27-28x time(s) | | | | | | | | | |
| 30 | | Final drain (all lines) | | | | | | | | | |
| 31 | | | | | | | | | | | |
| 32 | | | | | | | | | | | |
| 33 | | | | | | | | | | | |

TABLE 5A

| Step | Phase | CHART 5 (PAGE 1) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD) STEP DESCRIPTION Item number | Step time or volume | Circulation tk outlet valve - also open 3 in rinse low level 2 | CIP supply pump 6 | Aqueduc water valve 8 | Block & bleed aqueduc water valve 9 | Steam modulating valve (set point controlled by RTD) 15 | Routing valve from CIP to circuit 18 |
|---|---|---|---|---|---|---|---|---|---|
| 0 | | Home | | | | | | | |
| 1 | Rec | Partial rinse to circuit & pull | | | | X | X | | X |
| 2 | | Push & pull to recovery silo | | | | | | | |
| 3 | Rinse | Partial rinse to circuit & pull | | | X | | | | X |
| 4 | | Push & pull to drain | | | | | | | |
| 5 | | Do steps 3-4 (+reverse flow) | | | | | | | |
| 6 | | Repeat steps 3-5x time(s) | | | | | | | |
| 7 | Caustic | Caust. atom. + vacuumization | | | | | | | |
| 8 | | Push & pull + atomization | | | | | | | |
| 9 | | Pause | | | | | | | |
| 10 | | Repeat steps 7-9x time(s) | | | | | | | |
| 11 | Rinse | Partial rinse to circuit & pull | | | X | | | | X |
| 12 | | Push & pull to caustic tank | | | | | | | |
| 13 | | Repeat steps 11-12x time(s) | | | | | | | |
| 14 | Acid | Acid atom. + vacuumization | | | | | | | |
| 15 | | Push & pull + atomization | | | | | | | |
| 16 | | Pause | | | | | | | |
| 17 | | Repeat steps 14-16x time(s) | | | | | | | |
| 18 | Rinse | Partial rinse to circuit & pull | | | X | | | | X |
| 19 | | Push & pull to acid tank | | | | | | | |
| 20 | | Repeat steps 18-19x time(s) | | | | | | | |
| 21 | Sanitizer | Sani. Atom. + vacuumization | | | | | | | |
| 22 | | Push & pull + atomization | | | | | | | |
| 23 | | Repeat steps 21-22x time(s) | | | | | | | |
| 24 | | Final drain (all lines) | | | | X | | | X |
| 25 | | | | | | | | | |
| 26 | | | | | | | | | |
| 27 | | | | | | | | | |
| 28 | | | | | | | | | |
| 29 | | | | | | | | | |
| 30 | | | | | | | | | |
| 31 | | | | | | | | | |
| 32 | | | | | | | | | |

| Step | Phase | CHART 5 (PAGE 1) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD) STEP DESCRIPTION Item number | Routing valve to circulation tank 1 20 | Chemical & compressed gas main valve 23 | Atomized chemical valve (caustic or acid or sanitizer) 24 | Compressed gas valve 26 | Live steam valve (flow controlled) 27 | Flow restriction valve (normally open to circuit) 31 | Routing valves - also activate 35 (reverse flow valves) 32 |
|---|---|---|---|---|---|---|---|---|
| 0 | | Home | | | | | | | |
| 1 | Rec | Partial rinse to circuit & pull | | | | | | | |
| 2 | | Push & pull to recovery silo | | X | | X | | | |
| 3 | Rinse | Partial rinse to circuit & pull | | | | | | | |
| 4 | | Push & pull to drain | | X | | X | | | |
| 5 | | Do steps 3-4 (+reverse flow) | | | | | | | X |
| 6 | | Repeat steps 3-5x time(s) | | | | | | | |
| 7 | Caustic | Caust. atom. + vacuumization | | X | X | | X | | |
| 8 | | Push & pull + atomization | | X | X | X | X | | |
| 9 | | Pause | | | | | | | |

TABLE 5A-continued

| Step | Phase | Item number | 38 | 45 | 46 | 47 | 48 | 54 | 55 |
|---|---|---|---|---|---|---|---|---|---|
| 10 | | Repeat steps 7-9x time(s) | | | | | | | |
| 11 | Rinse | Partial rinse to circuit & pull | | | | | | | |
| 12 | | Push & pull to caustic tank | | | X | | X | | |
| 13 | | Repeat steps 11-12x time(s) | | | | | | | |
| 14 | Acid | Acid atom. + vacuumization | | | X | X | | X | |
| 15 | | Push & pull + atomization | | | X | X | X | X | |
| 16 | | Pause | | | | | | | |
| 17 | | Repeat steps 14-16x time(s) | | | | | | | |
| 18 | Rinse | Partial rinse to circuit & pull | | | | | | | |
| 19 | | Push & pull to acid tank | | | X | | X | | |
| 20 | | Repeat steps 18-19x time(s) | | | | | | | |
| 21 | Sanitizer | Sani. Atom. + vacuumization | | | | | | | |
| 22 | | Push & pull + atomization | | | X | X | | X | |
| 23 | | Repeat steps 21-22x time(s) | | | X | X | X | X | |
| 24 | | Final drain (all lines) | | | | | | | |
| 25 | | | | | | | | | |
| 26 | | | | | | | | | |
| 27 | | | | | | | | | |
| 28 | | | | | | | | | |
| 29 | | | | | | | | | |
| 30 | | | | | | | | | |
| 31 | | | | | | | | | |
| 32 | | | | | | | | | |

CHART 5 (PAGE 1) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD)

| Step | Phase | Item number / STEP DESCRIPTION | Suction return pump 38 | Aspirator/ blower fan 45 | Routing valve (normally open to 51) 46 | Routing valve (open path to pipe 49 when on) 47 | Routing valve to tank 1 (if off, or to pipe 61 if on) 48 | Vacuum pump (also open valve 53) 54 | Routing valve (off = to drain, on = to any CIP tank) 55 |
|---|---|---|---|---|---|---|---|---|---|
| 0 | | Home | | | | | | | |
| 1 | Rec | Partial rinse to circuit & pull | X | | | | | | |
| 2 | | Push & pull to recovery silo | X | | | | | | |
| 3 | Rinse | Partial rinse to circuit & pull | X | | | | | | |
| 4 | | Push & pull to drain | X | | | | | | |
| 5 | | Do steps 3-4 (+reverse flow) | | | | | | | |
| 6 | | Repeat steps 3-5x time(s) | | | | | | | |
| 7 | Caustic | Caust. atom. + vacuumization | X | | | | | X | X |
| 8 | | Push & pull + atomization | X | | | | | X | X |
| 9 | | Pause | | | | | | | |
| 10 | | Repeat steps 7-9x time(s) | | | | | | | |
| 11 | Rinse | Partial rinse to circuit & pull | X | | | | | | X |
| 12 | | Push & pull to caustic tank | X | | | | | | X |
| 13 | | Repeat steps 11-12x time(s) | | | | | | | |
| 14 | Acid | Acid atom. + vacuumization | X | | | | | X | X |
| 15 | | Push & pull + atomization | X | | | | | X | X |
| 16 | | Pause | | | | | | | |
| 17 | | Repeat steps 14-16x time(s) | | | | | | | |
| 18 | Rinse | Partial rinse to circuit & pull | X | | | | | | X |
| 19 | | Push & pull to acid tank | X | | | | | | X |
| 20 | | Repeat steps 18-19x time(s) | | | | | | | |
| 21 | Sanitizer | Sani. Atom. + vacuumization | | | | | | | |
| 22 | | Push & pull + atomization | X | | | | | X | X |
| 23 | | Repeat steps 21-22x time(s) | X | | | | | X | X |
| 24 | | Final drain (all lines) | | | | X | X | | |
| 25 | | | | | | | | | |
| 26 | | | | | | | | | |
| 27 | | | | | | | | | |
| 28 | | | | | | | | | |
| 29 | | | | | | | | | |
| 30 | | | | | | | | | |
| 31 | | | | | | | | | |
| 32 | | | | | | | | | |

TABLE 5B

| Step | Phase | CHART 5 (PAGE 2) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD) STEP DESCRIPTION Item number | Step time or volume | Routing valve (open path from 51 to 49 when on) 56 | CIP drain valve (normally open to drain) 58 | Chemical injection port (add by conductivity or flow) 59 | Routing valve to recov. silo (also turn on valve 81) 62 | Fresh water tank outlet valve 63 |
|---|---|---|---|---|---|---|---|---|
| 0 | | Home | | | | | | |
| 1 | Rec | Partial rinse to circuit & pull | | | | | X | |
| 2 | | Push & pull to recovery silo | | | | | X | |
| 3 | Rinse | Partial rinse to circuit & pull | | | X | | | |
| 4 | | Push & pull to drain | | | X | | | |
| 5 | | Do steps 3-4 (+reverse flow) | | | | | | |
| 6 | | Repeat steps 3-5x time(s) | | | | | | |
| 7 | Caustic | Caust. atom. + vacuumization | | | | | | |
| 8 | | Push & pull + atomization | | | | | | |
| 9 | | Pause | | | | | | |
| 10 | | Repeat steps 7-9x time(s) | | | | | | |
| 11 | Rinse | Partial rinse to circuit & pull | | | | | | X |
| 12 | | Push & pull to caustic tank | | | | | | |
| 13 | | Repeat steps 11-12x time(s) | | | | | | |
| 14 | Acid | Acid atom. + vacuumization | | | | | | |
| 15 | | Push & pull + atomization | | | | | | |
| 16 | | Pause | | | | | | |
| 17 | | Repeat steps 14-16x time(s) | | | | | | |
| 18 | Rinse | Partial rinse to circuit & pull | | | | | | X |
| 19 | | Push & pull to acid tank | | | | | | |
| 20 | | Repeat steps 18-19x time(s) | | | | | | |
| 21 | Sanitizer | Sani. Atom. + vacuumization | | | | | | |
| 22 | | Push & pull + atomization | | | | | | |
| 23 | | Repeat steps 21-22x time(s) | | | | | | |
| 24 | | Final drain (all lines) | | | X | | | |
| 25 | | | | | | | | |
| 26 | | | | | | | | |
| 27 | | | | | | | | |
| 28 | | | | | | | | |
| 29 | | | | | | | | |
| 30 | | | | | | | | |
| 31 | | | | | | | | |
| 32 | | | | | | | | |

| Step | Phase | CHART 5 (PAGE 2) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD) STEP DESCRIPTION Item number | Chemical solution tanks blocking valve 64 | Caustic tank outlet valve 65 | Recovered rinse tank outlet valve 66 | Acid tank outlet valve 67 | Caustic tank return valve (switch to 70 at high level) 69 | Recov. rinse tank return valve (to drain at high level) 70 |
|---|---|---|---|---|---|---|---|---|
| 0 | | Home | | | | | | |
| 1 | Rec | Partial rinse to circuit & pull | | | | | | |
| 2 | | Push & pull to recovery silo | | | | | | |
| 3 | Rinse | Partial rinse to circuit & pull | X | | X | | | |
| 4 | | Push & pull to drain | X | | X | | | |
| 5 | | Do steps 3-4 (+reverse flow) | | | | | | |
| 6 | | Repeat steps 3-5x time(s) | | | | | | |
| 7 | Caustic | Caust. atom. + vacuumization | | | | | | |
| 8 | | Push & pull + atomization | | | | | | |
| 9 | | Pause | | | | | | |

TABLE 5B-continued

| Step | Phase | Step Description | | | | | | | | | | |
|---|---|---|---|---|---|---|---|---|---|---|---|---|
| 10 | | Repeat steps 7-9x time(s) | | | | | | | | | | |
| 11 | Rinse | Partial rinse to circuit & pull | | | | | | | | | | X |
| 12 | | Push & pull to caustic tank | | | | | | | | | | X |
| 13 | | Repeat steps 11-12x time(s) | | | | | | | | | | |
| 14 | Acid | Acid atom. + vacuumization | | | | | | | | | | |
| 15 | | Push & pull + atomization | | | | | | | | | | |
| 16 | | Pause | | | | | | | | | | |
| 17 | | Repeat steps 14-16x time(s) | | | | | | | | | | |
| 18 | Rinse | Partial rinse to circuit & pull | | | | | | | | | | |
| 19 | | Push & pull to acid tank | | | | | | | | | | |
| 20 | | Repeat steps 18-19x time(s) | | | | | | | | | | |
| 21 | Sanitizer | Sani. Atom. + vacuumization | | | | | | | | | | |
| 22 | | Push & pull + atomization | | | | | | | | | | |
| 23 | | Repeat steps 21-22x time(s) | | | | | | | | | | |
| 24 | | Final drain (all lines) | X | | | | | | | | | |
| 25 | | | | | | | | | | | | |
| 26 | | | | | | | | | | | | |
| 27 | | | | | | | | | | | | |
| 28 | | | | | | | | | | | | |
| 29 | | | | | | | | | | | | |
| 30 | | | | | | | | | | | | |
| 31 | | | | | | | | | | | | |
| 32 | | | | | | | | | | | | |

CHART 5 (PAGE 2) REFERENCE DRAWING 5 LINE WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH VACUUMIZATION OF THE CIRCUIT FOLLOWED BY VACUUM LOSS WITH THE PUSH & PULL METHOD)

| Step | Phase | Step Description / Item number | Acid tank return valve (switch to drain if at high level) 71 | Spare 72 | Spare 73 | Aspirator/ blower fan 74 | Spare 75 | Spare 76 | Spare 77 | Spare 78 | Spare 79 | Spare 80 |
|---|---|---|---|---|---|---|---|---|---|---|---|---|
| 0 | | Home | | | | | | | | | | |
| 1 | Rec | Partial rinse to circuit & pull | | | | | | | | | | |
| 2 | | Push & pull to recovery silo | | | | | | | | | | |
| 3 | Rinse | Partial rinse to circuit & pull | | | | | | | | | | |
| 4 | | Push & pull to drain | | | | | | | | | | |
| 5 | | Do steps 3-4 (+reverse flow) | | | | | | | | | | |
| 6 | | Repeat steps 3-5x time(s) | | | | | | | | | | |
| 7 | Caustic | Caust. atom. + vacuumization | | | | | | | | | | |
| 8 | | Push & pull + atomization | | | | | | | | | | |
| 9 | | Pause | | | | | | | | | | |
| 10 | | Repeat steps 7-9x time(s) | | | | | | | | | | |
| 11 | Rinse | Partial rinse to circuit & pull | | | | | | | | | | |
| 12 | | Push & pull to caustic tank | | | | | | | | | | |
| 13 | | Repeat steps 11-12x time(s) | | | | | | | | | | |
| 14 | Acid | Acid atom. + vacuumization | | | | | | | | | | |
| 15 | | Push & pull + atomization | | | | | | | | | | |
| 16 | | Pause | | | | | | | | | | |
| 17 | | Repeat steps 14-16x time(s) | | | | | | | | | | |
| 18 | Rinse | Partial rinse to circuit & pull | X | | | | | | | | | |
| 19 | | Push & pull to acid tank | X | | | | | | | | | |
| 20 | | Repeat steps 18-19x time(s) | | | | | | | | | | |
| 21 | Sanitizer | Sani. Atom. + vacuumization | | | | | | | | | | |
| 22 | | Push & pull + atomization | | | | | | | | | | |
| 23 | | Repeat steps 21-22x time(s) | | | | | | | | | | |
| 24 | | Final drain (all lines) | | | | | | | | | | |
| 25 | | | | | | | | | | | | |
| 26 | | | | | | | | | | | | |
| 27 | | | | | | | | | | | | |
| 28 | | | | | | | | | | | | |
| 29 | | | | | | | | | | | | |
| 30 | | | | | | | | | | | | |
| 31 | | | | | | | | | | | | |
| 32 | | | | | | | | | | | | |

TABLE 6A

CHART 6 (PAGE 1) REFERENCE DRAWING 6a
SILO WASH & SANITIZE PROGRAM USING THE PUSH & PULL METHOD

| Step | Phase | STEP DESCRIPTION / Item number | Step time or volume | Circulation tk outlet valve - also open 3 in rinse low level (2) | CIP supply pump (6) | Aqueduc water valve (8) | Block & bleed aqueduc water valve (9) | Steam flow valve (also turn on steam shutt off valve 14) (15) | Routing valve from CIP to circuit (18) | Routing valve to circulation tank 1 (20) | Chemical & compressed gas main valve (23) | Atomized chemical valve (caustic or acid or sanitizer) (24) | Compressed gas valve (26) | Live steam valve (flow controlled) (27) | Flow restriction valve (normally open to circuit) (31) |
|---|---|---|---|---|---|---|---|---|---|---|---|---|---|---|---|
| 0 |  | Home |  |  |  |  |  |  |  |  |  |  |  |  |  |
| 1 | Recovery | Partial rinse to circuit & pull |  |  |  | X | X |  | X |  |  |  |  |  |  |
| 2 |  | Push & pull to recovery silo |  |  |  |  |  |  |  |  | X |  | X |  |  |
| 3 |  | Push & pull to recovery silo |  |  |  |  |  |  |  |  | X |  | X |  |  |
| 4 |  | Push & pull to recovery silo |  |  |  |  |  |  |  |  | X |  | X |  |  |
| 5 | Rinse | Partial rinse to circuit & pull |  |  | X |  |  |  | X |  |  |  |  |  |  |
| 6 |  | Push & pull to drain |  |  |  |  |  |  |  |  | X |  | X |  |  |
| 7 |  | Push & pull to drain |  |  |  |  |  |  |  |  | X |  | X |  |  |
| 8 |  | Repeat steps 5-7 twice |  |  |  |  |  |  |  |  |  |  |  |  |  |
| 9 |  | Push & pull (empty lines) |  |  |  |  |  |  |  |  | X |  | X |  |  |
| 10 |  | Drain silo & lines |  |  |  |  |  |  |  |  | X |  | X |  |  |
| 11 | Caustic | Partial caustic Sol'n to silo |  |  | X |  |  |  | X |  |  |  |  |  |  |
| 12 |  | Push & pull to circulation tk |  |  |  |  |  |  |  |  | X | X | X | X |  |
| 13 |  | Same caustic sol'n to silo |  | X | X |  |  | X | X |  |  |  |  |  |  |
| 14 |  | Push & pull to circulation tk |  | X | X |  |  | X |  | X | X | X | X | X |  |
| 15 |  | Push & pull to circulation tk |  | X | X |  |  | X |  | X | X | X | X | X |  |
| 16 |  | Push & pull (empty lines) |  | X | X |  |  | X |  | X | X | X | X | X |  |
| 17 |  | Repeat steps 13-16x times |  |  |  |  |  |  |  |  |  |  |  |  |  |
| 18 | Rinse | Empty circulation tank |  | X | X |  |  |  | X |  |  |  |  |  |  |
| 19 |  | Push & pull to caustic tank |  |  |  |  |  |  |  |  | X |  | X |  |  |
| 20 |  | Push & pull to caustic tank |  |  |  |  |  |  |  |  | X |  | X |  |  |
| 21 |  | Push & pull (empty lines) |  |  |  |  |  |  |  |  | X |  | X |  |  |
| 22 |  | Partial rinse to circuit & pull |  | X | X |  |  |  | X |  |  |  |  |  |  |
| 23 |  | Push & pull to caustic tank |  |  |  |  |  |  |  |  | X |  | X |  |  |
| 24 |  | Push & pull to caustic tank |  |  |  |  |  |  |  |  | X |  | X |  |  |
| 25 |  | Push & pull (empty lines) |  |  |  |  |  |  |  |  |  |  |  |  |  |
| 26 |  | Repeat steps 22-25x times |  |  |  |  |  |  |  |  |  |  |  |  |  |
| 27 |  | Drain silo & lines |  |  |  |  |  |  |  |  |  |  |  |  |  |
| 28 | Sanitizing | Partial sanitizer sol'n prep. |  |  | X |  |  |  |  |  |  |  |  |  |  |
| 29 |  | Sol'n sent to circuit & pull |  | X | X |  |  |  | X |  |  |  |  |  |  |
| 30 |  | Push & pull to drain |  |  |  |  |  |  |  |  |  |  |  |  |  |
| 31 |  | Push & pull (pulse silo valve) |  |  |  |  |  |  |  |  |  |  |  |  |  |
| 32 |  | Push & pull to drain |  |  |  |  |  |  |  |  |  |  |  |  |  |
| 33 |  | Final drain (silo & lines) |  |  |  |  |  |  |  |  |  |  |  |  |  |

TABLE 6A-continued

| Step | Phase | Step Description | | | |
|---|---|---|---|---|---|
| 25 | | Push & pull (empty lines) | | X | X |
| 26 | | Repeat steps 22-25x times | | | |
| 27 | | Drain silo & lines | | X | X |
| 28 | Sanitizing | Partial sanitizer sol'n prep. | X | | |
| 29 | | Sol'n sent to circuit & pull | | | |
| 30 | | Push & pull to drain | X | X | X |
| 31 | | Push & pull (pulse silo valve) | X | X | X |
| 32 | | Push & pull to drain | X | X | X |
| 33 | | Final drain (silo & lines) | X | X | X |

| Step | Phase | CHART 6 (PAGE 1) REFERENCE DRAWING 6a SILO WASH & SANITIZE PROGRAM USING THE PUSH & PULL METHOD STEP DESCRIPTION Item number | Routing valves - also activate 35 (reverse flow valves) 32 | Suction return pump 38 | Aspirator/ blower fan 45 | Routing valve (normally open to 51) 46 | Routing valve (open path to pipe 49 when on) 47 | Routing valve to tank 1 (if off, or to pipe 61 if on) 48 | Vacuum pump (also open valve 53) 54 | Routing valve (off = to drain, on = to any CIP tank) 55 |
|---|---|---|---|---|---|---|---|---|---|---|
| 0 | | Home | | | | | | | | |
| 1 | Re- | Partial rinse to circuit & pull | | X | | | | | | |
| 2 | covery | Push & pull to recovery silo | | X | | | | | | |
| 3 | | Push & pull to recovery silo | | X | | | | | | |
| 4 | | Push & pull to recovery silo | | X | | | | | | |
| 5 | Rinse | Partial rinse to circuit & pull | | X | | | | | | |
| 6 | | Push & pull to drain | | X | | | | | | |
| 7 | | Push & pull to drain | | X | | | | | | |
| 8 | | Repeat steps 5-7 twice | | | | | | | | |
| 9 | | Push & pull (empty lines) | | X | | | | | | |
| 10 | | Drain silo & lines | | | | | | | | |
| 11 | Caustic | Partial caustic Sol'n to silo | | X | | | | | | X |
| 12 | | Push & pull to circulation tk | | X | | | | | | X |
| 13 | | Same caustic sol'n to silo | | X | | | | | | X |
| 14 | | Push & pull to circulation tk | | X | | | | | | X |
| 15 | | Push & pull to circulation tk | | X | | | | | | X |
| 16 | | Push & pull (empty lines) | | X | | | | | | X |
| 17 | | Repeat steps 13-16x times | | | | | | | | |
| 18 | Rinse | Empty circulation tank | | X | | | | | | X |
| 19 | | Push & pull to caustic tank | | X | | | | | | X |
| 20 | | Push & pull to caustic tank | | X | | | | | | X |
| 21 | | Push & pull (empty lines) | | X | | | | | | X |
| 22 | | Partial rinse to circuit & pull | | X | | | | | | X |
| 23 | | Push & pull to caustic tank | | X | | | | | | X |
| 24 | | Push & pull to caustic tank | | X | | | | | | X |
| 25 | | Push & pull (empty lines) | | X | | | | | | X |
| 26 | | Repeat steps 22-25x times | | | | | | | | |
| 27 | | Drain silo & lines | | | | | | | | |
| 28 | Sani- | Partial sanitizer sol'n prep. | | | | | | | | |
| 29 | tizing | Sol'n sent to circuit & pull | | | | | | | | |
| 30 | | Push & pull to drain | | X | | | | | | |
| 31 | | Push & pull (pulse silo valve) | | X | | | | | | |
| 32 | | Push & pull to drain | | X | | | | | | |
| 33 | | Final drain (silo & lines) | | | | | | | | |

TABLE 6B

| Step | Phase | CHART 6 (PAGE 2) REFERENCE DRAWING 6a SILO WASH & SANITIZE PROGRAM USING THE PUSH & PULL METHOD STEP DESCRIPTION Item number | Step time or volume | Routing valve (open path from 51 to 49 when on) 56 | CIP drain valve (normally open to drain) 58 | Chemical injection port (added by conductivity or flow) 59 | Routing valve to drain or re-covery silo (also turn on 81) 62 | Fresh water tank outlet valve 63 | Chemical solution tanks blocking valve 64 |
|---|---|---|---|---|---|---|---|---|---|
| 0 | | Home | | | | | | | |
| 1 | Re- | Partial rinse to circuit & pull | | | | | X | | |
| 2 | covery | Push & pull to recovery silo | | | | | X | | |
| 3 | | Push & pull to recovery silo | | | | | X | | |
| 4 | | Push & pull to recovery silo | | | | | X | | |
| 5 | Rinse | Partial rinse to circuit & pull | | | X | | | | X |
| 6 | | Push & pull to drain | | | X | | | | X |
| 7 | | Push & pull to drain | | | X | | | | X |
| 8 | | Repeat steps 5-7 twice | | | | | | | |

TABLE 6B-continued

| Step | Phase | Step Description | | | | | | |
|---|---|---|---|---|---|---|---|---|
| 9 | | Push & pull (empty lines) | | X | | | | X |
| 10 | | Drain silo & lines | | X | | | | X |
| 11 | Caustic | Partial caustic sol'n to silo | X | X | | | | X |
| 12 | wash | Push & pull to circulation tk | X | X | | | | X |
| 13 | | Same caustic sol'n to silo | X | X | | X | | X |
| 14 | | Push & pull to circulation tk | X | X | | X | | X |
| 15 | | Push & pull to circulation tk | X | X | | X | | X |
| 16 | | Push & pull (empty lines) | X | X | | X | | X |
| 17 | | Repeat steps 13-16x times | | | | | | |
| 18 | Rinse | Empty circulation tank | | X | | | | |
| 19 | | Push & pull to caustic tank | | | | | | |
| 20 | | Push & pull to caustic tank | | | | | | |
| 21 | | Push & pull (empty lines) | | | | | | |
| 22 | | Partial rinse to circuit & pull | | | | | | |
| 23 | | Push & pull to caustic tank | | | | | | |
| 24 | | Push & pull to caustic tank | | | | | | |
| 25 | | Push & pull (empty lines) | | | | | | |
| 26 | | Repeat steps 22-25x times | | | | | | |
| 27 | | Drain silo & lines | | | | | | X |
| 28 | Sani- | Partial sanitizer sol'n prep. | | | | X | | X |
| 29 | tizing | Sol'n sent to circuit & pull | | | | | | |
| 30 | | Push & pull to drain | | | | | | |
| 31 | | Push & pull (pulse silo valve) | | | | | | |
| 32 | | Push & pull to drain | | | | | | |
| 33 | | Final drain (silo & lines) | | | | | | |

| Step | Phase | CHART 6 (PAGE 2) REFERENCE DRAWING 6a SILO WASH & SANITIZE PROGRAM USING THE PUSH & PULL METHOD STEP DESCRIPTION Item number | Caustic tank outlet valve 65 | Re-covered rinse tank outlet valve 66 | Acid tank outlet valve 67 | Caustic tank return valve (switch to 70 at high level) 69 | Re-covered rinse tank return valve (to drain at high level) 70 | Acid tank return valve (switch to drain if at high level) 71 |
|---|---|---|---|---|---|---|---|---|
| 0 | | Home | | | | | | |
| 1 | Re- | Partial rinse to circuit & pull | | | | | | |
| 2 | covery | Push & pull to recovery silo | | | | | | |
| 3 | | Push & pull to recovery silo | | | | | | |
| 4 | | Push & pull to recovery silo | | | | | | |
| 5 | Rinse | Partial rinse to circuit & pull | | X | | | | |
| 6 | | Push & pull to drain | | X | | | | |
| 7 | | Push & pull to drain | | X | | | | |
| 8 | | Repeat steps 5-7 twice | | | | | | |
| 9 | | Push & pull (empty lines) | | | | | | |
| 10 | | Drain silo & lines | | | | | | |
| 11 | Caustic | Partial caustic sol'n to silo | X | | | | | |
| 12 | wash | Push & pull to circulation tk | X | | | | | |
| 13 | | Same caustic sol'n to silo | | | | | | |
| 14 | | Push & pull to circulation tk | | | | | | |
| 15 | | Push & pull to circulation tk | | | | | | |
| 16 | | Push & pull (empty lines) | | | | | | |
| 17 | | Repeat steps 13-16x times | | | | | | |
| 18 | Rinse | Empty circulation tank | | | | X | | |
| 19 | | Push & pull to caustic tank | | | | X | | |
| 20 | | Push & pull to caustic tank | | | | X | | |
| 21 | | Push & pull (empty lines) | | | | X | | |
| 22 | | Partial rinse to circuit & pull | | | | X | | |
| 23 | | Push & pull to caustic tank | | | | X | | |
| 24 | | Push & pull to caustic tank | | | | X | | |
| 25 | | Push & pull (empty lines) | | | | X | | |
| 26 | | Repeat steps 22-25x times | | | | | | |
| 27 | | Drain silo & lines | | | | | | |
| 28 | Sani- | Partial sanitizer sol'n prep. | | | | | | |
| 29 | tizing | Sol'n sent to circuit & pull | | | | | | |
| 30 | | Push & pull to drain | | | | | | |
| 31 | | Push & pull (pulse silo valve) | | | | | | |
| 32 | | Push & pull to drain | | | | | | |
| 33 | | Final drain (silo & lines) | | | | | | |

TABLE 6B-continued

| Step | Phase | CHART 6 (PAGE 2) REFERENCE DRAWING 6a SILO WASH & SANITIZE PROGRAM USING THE PUSH & PULL METHOD STEP DESCRIPTION Item number | Silo by pass valve 572 | Routing valve to flow panel and to selected silo 573 | Suction pump prior to silo 574 | Silo inlet valve 575 | Silo outlet valve 576 | Spare 577 | Spare 578 | Spare 579 | Silo & return line drain valve 580 |
|---|---|---|---|---|---|---|---|---|---|---|---|
| 0 | | Home | | | | | | | | | |
| 1 | Re- | Partial rinse to circuit & pull | | X | X | | X | | | | |
| 2 | covery | Push & pull to recovery silo | | X | X | | X | | | | |
| 3 | | Push & pull to recovery silo | | X | X | X | X | | | | |
| 4 | | Push & pull to recovery silo | X | | | | | | | | |
| 5 | Rinse | Partial rinse to circuit & pull | | X | X | | X | | | | |
| 6 | | Push & pull to drain | | X | X | | X | | | | |
| 7 | | Push & pull to drain | | X | X | X | X | | | | |
| 8 | | Repeat steps 5-7 twice | | | | | | | | | |
| 9 | | Push & pull (empty lines) | X | | | | | | | | |
| 10 | | Drain silo & lines | X | X | | X | X | | | | X |
| 11 | Caustic | Partial caustic sol'n to silo | | X | X | | X | | | | |
| 12 | wash | Push & pull to circulation tk | | X | X | | X | | | | |
| 13 | | Same caustic sol'n to silo | | X | X | | X | | | | |
| 14 | | Push & pull to circulation tk | | X | X | | X | | | | |
| 15 | | Push & pull to circulation tk | | X | X | X | X | | | | |
| 16 | | Push & pull (empty lines) | X | | | | | | | | |
| 17 | | Repeat steps 13-16x times | | | | | | | | | |
| 18 | Rinse | Empty circulation tank | | X | X | | X | | | | |
| 19 | | Push & pull to caustic tank | | X | X | | X | | | | |
| 20 | | Push & pull to caustic tank | | X | X | X | X | | | | |
| 21 | | Push & pull (empty lines) | X | | | | | | | | |
| 22 | | Partial rinse to circuit & pull | | X | X | | X | | | | |
| 23 | | Push & pull to caustic tank | | X | X | | X | | | | |
| 24 | | Push & pull to caustic tank | | X | X | X | X | | | | |
| 25 | | Push & pull (empty lines) | X | | | | | | | | |
| 26 | | Repeat steps 22-25x times | | | | | | | | | |
| 27 | | Drain silo & lines | X | X | | X | X | | | | X |
| 28 | Sani- | Partial sanitizer sol'n prep. | | | | | | | | | |
| 29 | tizing | Sol'n sent to circuit & pull | | X | X | | X | | | | |
| 30 | | Push & pull to drain | | X | X | | X | | | | |
| 31 | | Push & pull (pulse silo valve) | | X | X | X | | | | | |
| 32 | | Push & pull to drain | | X | X | X | X | | | | |
| 33 | | Final drain (silo & lines) | X | X | | X | X | | | | X |

TABLE 7A

| Step | Phase | CHART 7 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS CHEMICAL ATOMIZATION IS FOLLOWED BY AN OPTIONAL PAUSE) STEP DESCRIPTION Item number | Step time or volume | Circulation tk outlet valve - also open 3 in rinse low level 2 | CIP supply pump 6 | Aqueduc water valve 8 | Aqueduc block & bleed water valve 9 | Steam modulating valve (set point controlled by RTD) 15 | Routing valve from CIP to circuit 18 |
|---|---|---|---|---|---|---|---|---|---|
| 0 | | Home | | | | | | | |
| 10 | | Steps 1-10 same as chart 6 | | | | | | | |
| 11 | Caustic | Partial caustic sol'n to silo | | | X | | | X | X |
| 12 | | Push + atom. caustic & pull | | | | | | | |
| 13 | | Push + atom. caustic & pull | | | | | | | |
| 14 | | Push + atom. caustic & pull | | | | | | | |
| 15 | | Pause | | | | | | | |
| 16 | | Repeat steps 12-16x tm(s) | | | | | | | |
| 17 | Rinse | Partial rinse to silo & pull | | | X | | | | X |
| 18 | | Push & pull to caustic tank | | | | | | | |
| 19 | | Push & pull to caustic tank | | | | | | | |
| 20 | | Push & pull to caustic tank | | | | | | | |
| 21 | | Push & pull to empty lines | | | | | | | |
| 22 | | Repeat steps 18-21x times | | | | | | | |
| 23 | | Drain silo & lines | | | | | | | |

TABLE 7A-continued

| Step | Phase | Item number | | | | | | |
|---|---|---|---|---|---|---|---|---|
| 24 | Sanitizing | Partial sani sol'n preparat. | | X | | | | |
| 25 | | Partial sani sol'n to silo | X | X | | | | |
| 26 | | Push + atom. sani & pull | | | | | | |
| 27 | | Push + atom. sani & pull | | | | | | |
| 28 | | Push + atom. sani & pull | | | | | | |
| 29 | | Pause | | | | | | |
| 30 | | Final drain (silo & lines) | | | | | | |
| 31 | | | | | | | | |
| 32 | | | | | | | | |
| 33 | | | | | | | | |
| 34 | | | | | | | | |
| 35 | | | | | | | | |
| 36 | | | | | | | | |
| 37 | | | | | | | | |
| 38 | | | | | | | | |
| 39 | | | | | | | | |
| 40 | | | | | | | | |
| 41 | | | | | | | | |

CHART 7 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS CHEMICAL AUTOMATION IS FOLLOWED BY AN OPTIONAL PAUSE

| Step | Phase | Item number STEP DESCRIPTION | Routing valve to circulation tank 1 — 20 | Chemical & compressed gas main valve — 23 | Atomized chemical valve (caustic or acid or sanitizer) — 24 | Compressed gas valve — 26 | Live steam valve (flow controlled) — 27 | Flow restriction valve (normally open to circuit) — 31 | Routing valves - also activate 35 (reverse flow valves) — 32 |
|---|---|---|---|---|---|---|---|---|---|
| 0 | | Home | | | | | | | |
| 10 | | Steps 1-10 same as chart 6 | | | | | | | |
| 11 | Caustic | Partial caustic sol'n to silo | | | | | | | |
| 12 | | Push + atom. caustic & pull | | X | X | X | X | | |
| 13 | | Push + atom. caustic & pull | | X | X | X | X | | |
| 14 | | Push + atom. caustic & pull | | X | X | X | X | | |
| 15 | | Pause | | X | | | | | |
| 16 | | Repeat steps 12-16x tm(s) | | | | | | | |
| 17 | Rinse | Partial rinse to silo & pull | | | | | | | |
| 18 | | Push & pull to caustic tank | | X | | X | | | |
| 19 | | Push & pull to caustic tank | | X | | X | | | |
| 20 | | Push & pull to caustic tank | | X | | X | | | |
| 21 | | Push & pull to empty lines | | X | | X | | | |
| 22 | | Repeat steps 18-21x times | | | | | | | |
| 23 | | Drain silo & lines | | X | | X | | | |
| 24 | Sanitizing | Partial sani sol'n preparat. | X | | | | | | |
| 25 | | Partial sani sol'n to silo | | | | | | | |
| 26 | | Push + atom. sani & pull | | X | X | X | | | |
| 27 | | Push + atom. sani & pull | | X | X | X | | | |
| 28 | | Push + atom. sani & pull | | X | X | X | | | |
| 29 | | Pause | | X | | | | | |
| 30 | | Final drain (silo & lines) | | | | | | | |
| 31 | | | | | | | | | |
| 32 | | | | | | | | | |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

CHART 7 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS CHEMICAL AUTOMATION

| | Routing valve | Routing valve (open path | Routing valve to tank 1 (if off, | Vacuum pump (also | Routing valve (off = to |

TABLE 7A-continued

| Step | Phase | IS FOLLOWED BY AN OPTIONAL PAUSE) STEP DESCRIPTION Item number | Suction return pump 38 | Aspirator/ blower fan 45 | (normally open to 51) 46 | to pipe 49 when on) 47 | or to pipe 61 if on) 48 | open valve 53) 54 | drain, on = to any CIP tank) 55 |
|---|---|---|---|---|---|---|---|---|---|
| 0 | | Home | | | | | | | |
| 10 | | Steps 1-10 same as chart 6 | | | | | | | |
| 11 | Caustic | Partial caustic sol'n to silo | X | | | | | | X |
| 12 | | Push + atom. caustic & pull | X | | | | | | X |
| 13 | | Push + atom. caustic & pull | X | | | | | | X |
| 14 | | Push + atom. caustic & pull | X | | | | | | X |
| 15 | | Pause | | | | | | | X |
| 16 | | Repeat steps 12-16x tm(s) | | | | | | | |
| 17 | Rinse | Partial rinse to silo & pull | | | | | | | X |
| 18 | | Push & pull to caustic tank | X | | | | | | X |
| 19 | | Push & pull to caustic tank | X | | | | | | X |
| 20 | | Push & pull to caustic tank | X | | | | | | X |
| 21 | | Push & pull to empty lines | X | | | | | | X |
| 22 | | Repeat steps 18-21x times | | | | | | | X |
| 23 | | Drain silo & lines | | | | | | | |
| 24 | Sanitizing | Partial sani sol'n preparat. | | | | | | | |
| 25 | | Partial sani sol'n to silo | X | | | | | | |
| 26 | | Push + atom. sani & pull | X | | | | | | |
| 27 | | Push + atom. sani & pull | X | | | | | | |
| 28 | | Push + atom. sani & pull | X | | | | | | |
| 29 | | Pause | | | | | | | |
| 30 | | Final drain (silo & lines) | | | | | | | |
| 31 | | | | | | | | | |
| 32 | | | | | | | | | |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

TABLE 7B

| Step | Phase | CHART 7 (PAGE 2) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY AN OPTIONAL PAUSE) STEP DESCRIPTION Item number | Step time or Volume | Routing valve (open path from 51 to 49 when on) 56 | CIP drain valve (normally open to drain) 58 | Chemical injection port (add by conductivity or flow) 59 | Routing valve to recov. silo (also turn on valve 81) 62 | Fresh water tank outlet valve 63 | Chemical solution tanks blocking valve 64 |
|---|---|---|---|---|---|---|---|---|---|
| 0 | | Home | | | | | | | |
| 10 | | Steps 1-10 same as chart 6 | | | | | | | |
| 11 | Caustic | Partial caustic sol'n to silo | | | X | | | | X |
| 12 | | Push + atom. caustic & pull | | | | | | | |
| 13 | | Push + atom. caustic & pull | | | | | | | |
| 14 | | Push + atom. caustic & pull | | | | | | | |
| 15 | | Pause | | | | | | | |
| 16 | | Repeat steps 12-16x tm(s) | | | | | | | |
| 17 | Rinse | Partial rinse to silo & pull | | | | | | X | |
| 18 | | Push & pull to caustic tank | | | | | | X | |
| 19 | | Push & pull to caustic tank | | | | | | | |
| 20 | | Push & pull to caustic tank | | | | | | | |
| 21 | | Push & pull to empty lines | | | | | | | |
| 22 | | Repeat steps 18-21x times | | | | | | | |
| 23 | | Drain silo & lines | | | | | | | X |
| 24 | Sanitizing | Partial sani sol'n preparat. | | | | X | X | | |
| 25 | | Partial sani sol'n to silo | | | | | | | |
| 26 | | Push + atom. sani & pull | | | | | | | |
| 27 | | Push + atom. sani & pull | | | | | | | |
| 28 | | Push + atom. sani & pull | | | | | | | |
| 29 | | Pause | | | | | | | |

TABLE 7B-continued

| Step | | | |
|---|---|---|---|
| 30 | | Final drain (silo & lines) | |
| 31 | | | |
| 32 | | | |
| 33 | | | |
| 34 | | | |
| 35 | | | |
| 36 | | | |
| 37 | | | |
| 38 | | | |
| 39 | | | |
| 40 | | | |
| 41 | | | |

CHART 7 (PAGE 2) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY AN OPTIONAL PAUSE)

| Step | Phase | STEP DESCRIPTION Item number | Caustic tank outlet valve 65 | Recovered rinse tank outlet valve 66 | Acid tank outlet valve 67 | Caustic tank return valve (switch to 70 at high level) 69 | Recov. rinse tank return valve (to drain at high level) 70 | Acid tank return valve (switch to drain if at high level) 71 | Silo by pass valve 572 | Routing valve to flow panel and to selected silo 573 |
|---|---|---|---|---|---|---|---|---|---|---|
| 0 | | Home | | | | | | | | |
| 10 | | Steps 1-10 same as chart 6 | | | | | | | | |
| 11 | Caustic | Partial caustic sol'n to silo | X | | | | | | | X |
| 12 | | Push + atom. caustic & pull | | | | X | | | | X |
| 13 | | Push + atom. caustic & pull | | | | X | | | | X |
| 14 | | Push + atom. caustic & pull | | | | X | | | | X |
| 15 | | Pause | | | | X | | | | X |
| 16 | | Repeat steps 12-16x tm(s) | | | | | | | | |
| 17 | Rinse | Partial rinse to silo & pull | | | | X | | | | X |
| 18 | | Push & pull to caustic tank | | | | X | | | | X |
| 19 | | Push & pull to caustic tank | | | | X | | | | X |
| 20 | | Push & pull to caustic tank | | | | X | | | | X |
| 21 | | Push & pull to empty lines | | | | X | | | X | |
| 22 | | Repeat steps 18-21x times | | | | | | | | |
| 23 | | Drain silo & lines | | | | | | | X | X |
| 24 | Sani- tizing | Partial sani sol'n preparat. | | | | | | | | |
| 25 | | Partial sani sol'n to silo | | | | | | | | X |
| 26 | | Push + atom. sani & pull | | | | | | | | X |
| 27 | | Push + atom. sani & pull | | | | | | | | X |
| 28 | | Push + atom. sani & pull | | | | | | | | X |
| 29 | | Pause | | | | | | | | X |
| 30 | | Final drain (silo & lines) | | | | | | | X | X |
| 31 | | | | | | | | | | |
| 32 | | | | | | | | | | |
| 33 | | | | | | | | | | |
| 34 | | | | | | | | | | |
| 35 | | | | | | | | | | |
| 36 | | | | | | | | | | |
| 37 | | | | | | | | | | |
| 38 | | | | | | | | | | |
| 39 | | | | | | | | | | |
| 40 | | | | | | | | | | |
| 41 | | | | | | | | | | |

CHART 7 (PAGE 2) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY AN OPTIONAL PAUSE)

| Step | Phase | STEP DESCRIPTION Item number | Suction pump prior to silo 574 | Silo inlet valve 75 | Silo outlet valve 576 | Routing valve to silo spray ball 877 | Routing valve to silo inlet valve & overflow pipe 878 | Silo vent valve (off = open/ opens if vacuum or pressure) 879 | Silo & return line drain valve 580 |
|---|---|---|---|---|---|---|---|---|---|
| 0 | | Home | | | | | | | |
| 10 | | Steps 1-10 same as chart 6 | | | | | | | |
| 11 | Caustic | Partial caustic sol'n to silo | X | X | X | | X | | |

TABLE 7B-continued

| Step | Phase | Description | | | | | | |
|---|---|---|---|---|---|---|---|---|
| 12 | | Push + atom. caustic & pull | X | | X | X | | X |
| 13 | | Push + atom. caustic & pull | X | | X | | X | X |
| 14 | | Push + atom. caustic & pull | X | X | X | | X | X |
| 15 | | Pause | | X | X | X | X | X |
| 16 | | Repeat steps 12-16x tm(s) | | | | | | |
| 17 | Rinse | Partial rinse to silo & pull | X | | X | X | | |
| 18 | | Push & pull to caustic tank | X | | X | X | | |
| 19 | | Push & pull to caustic tank | X | | X | | X | X |
| 20 | | Push & pull to caustic tank | X | X | X | | X | X |
| 21 | | Push & pull to empty lines | | | | | | |
| 22 | | Repeat steps 18-21x times | | | | | | |
| 23 | | Drain silo & lines | | X | X | X | X | | X |
| 24 | Sanitizing | Partial sani sol'n preparat. | | | | | | |
| 25 | | Partial sani sol'n to silo | X | | X | X | | X |
| 26 | | Push + atom. sani & pull | X | | X | X | | X |
| 27 | | Push + atom. sani & pull | X | | X | | X | X |
| 28 | | Push + atom. sani & pull | X | X | X | | X | X |
| 29 | | Pause | | X | X | X | X | X |
| 30 | | Final drain (silo & lines) | | X | X | X | X | | X |
| 31 | | | | | | | | |
| 32 | | | | | | | | |
| 33 | | | | | | | | |
| 34 | | | | | | | | |
| 35 | | | | | | | | |
| 36 | | | | | | | | |
| 37 | | | | | | | | |
| 38 | | | | | | | | |
| 39 | | | | | | | | |
| 40 | | | | | | | | |
| 41 | | | | | | | | |

TABLE 8A

CHART 8 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY THE CIRCULATION OF THE ATOMIZED SOLUTION)

| Step | Phase | STEP DESCRIPTION Item number | Step time or volume | Circulation tk outlet valve - also open 3 in rinse low level 2 | CIP supply pump 6 | Aqueduc water valve 8 | Aqueduc block & bleed water valve 9 | Steam modulating valve (set point controlled by RTD) 15 | Routing valve from CIP to circuit 18 |
|---|---|---|---|---|---|---|---|---|---|
| 0 | | Home | | | | | | | |
| 10 | | Steps 1-10 same as chart 6 | | | | | | | |
| 11 | Caustic | Drain CIP suction & disch. | | | | X | | | X |
| 12 | | Push + atom. caustic & pull | | | | | | | |
| 13 | | Push + atom. caustic & pull | | | | | | | |
| 14 | | Push + atom. caustic & pull | | | | | | | |
| 15 | | Push + atom. caustic & pull | | | | | | | |
| 16 | | Circulate via silo spray ball | | | X | | | | X |
| 17 | | Circulate via silo overflow | | | X | | | | X |
| 18 | | Circulate via silo inlet valve | | | X | | | | X |
| 19 | | Circulate via silo by pass | | | X | | | | X |
| 20 | | Repeat steps 12-19x tm(s) | | | | | | | |
| 21 | Rinse | Partial rinse to silo & pull | | | X | | | | X |
| 22 | | Push & pull to caustic tank | | | | | | | |
| 23 | | Push & pull to caustic tank | | | | | | | |
| 24 | | Push & pull to caustic tank | | | | | | | |
| 25 | | Push & pull to empty lines | | | | | | | |
| 26 | | Repeat steps 22-25x tm(s) | | | | | | | |
| 27 | | Drain silo & lines | | | | | | | |
| 28 | Sanitizing | Partial sani. sol'n preparat. | | | X | | | | |
| 29 | | Partial sani to silo & pull | | X | X | | | | X |
| 30 | | Drain CIP suction & disch. | | | | X | | | |
| 31 | | Push + atom. Sani. & pull | | | | | | | |
| 32 | | Push + atom. Sani. & pull | | | | | | | |
| 33 | | Push + atom. Sani. & pull | | | | | | | |
| 34 | | Push + atom. Sani. & pull | | | | | | | |
| 35 | | Circulate via silo spray ball | | | X | | | | X |
| 36 | | Circulate via silo overflow | | | | | | | |

TABLE 8A-continued

| Step | Phase | Step Description | | | | | | |
|---|---|---|---|---|---|---|---|---|
| 37 | | Circulate via silo inlet valve | | | | | | |
| 38 | | Circulate via silo by pass | | | | | | |
| 39 | | Final drain (silo & lines) | X | | | | | X |
| 40 | | | | | | | | |
| 41 | | | | | | | | |

CHART 8 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY THE CIRCULATION OF THE ATOMIZED SOLUTION)

| Step | Phase | STEP DESCRIPTION Item number | Routing valve to circulation tank 1 | Chemical & compressed gas main valve | Atomized chemical valve (caustic or acid or sanitizer) | Compressed gas valve | Live steam valve (flow controlled) | Flow restriction valve (normally open to circuit) | Routing valves - also activate 35 (reverse flow valves) |
|---|---|---|---|---|---|---|---|---|---|
| | | | 20 | 23 | 24 | 26 | 27 | 31 | 32 |
| 0 | | Home | | | | | | | |
| 10 | | Steps 1-10 same as chart 6 | | | | | | | |
| 11 | Caustic | Drain CIP suction & disch. | | | | | | | |
| 12 | | Push + atom. caustic & pull | | X | X | X | X | | |
| 13 | | Push + atom. caustic & pull | | X | X | X | X | | |
| 14 | | Push + atom. caustic & pull | | X | X | X | X | | |
| 15 | | Push + atom. caustic & pull | | X | X | X | X | | |
| 16 | | Circulate via silo spray ball | | X | | | X | | |
| 17 | | Circulate via silo overflow | | X | | | X | | |
| 18 | | Circulate via silo inlet valve | | X | | | X | | |
| 19 | | Circulate via silo by pass | | X | | | X | | |
| 20 | | Repeat steps 12-19x tm(s) | | | | | | | |
| 21 | Rinse | Partial rinse to silo & pull | | | | | | | |
| 22 | | Push & pull to caustic tank | | X | | X | | | |
| 23 | | Push & pull to caustic tank | | X | | X | | | |
| 24 | | Push & pull to caustic tank | | X | | X | | | |
| 25 | | Push & pull to empty lines | | X | | X | | | |
| 26 | | Repeat steps 22-25x tm(s) | | | | | | | |
| 27 | | Drain silo & lines | | X | | X | | | |
| 28 | Sanitizing | Partial sani. sol'n preparat. | X | | | | | | |
| 29 | | Partial sani to silo & pull | | | | | | | |
| 30 | | Drain CIP suction & disch. | | | | | | | |
| 31 | | Push + atom. Sani. & pull | | X | X | X | | | |
| 32 | | Push + atom. Sani. & pull | | X | X | X | | | |
| 33 | | Push + atom. Sani. & pull | | X | X | X | | | |
| 34 | | Push + atom. Sani. & pull | | X | X | X | | | |
| 35 | | Circulate via silo spray ball | | | | | | | |
| 36 | | Circulate via silo overflow | | | | | | | |
| 37 | | Circulate via silo inlet valve | | | | | | | |
| 38 | | Circulate via silo by pass | | | | | | | |
| 39 | | Final drain (silo & lines) | | | | | | | |
| 40 | | | | | | | | | |
| 41 | | | | | | | | | |

CHART 8 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY THE CIRCULATION OF THE ATOMIZED SOLUTION)

| Step | Phase | STEP DESCRIPTION Item number | Suction return pump | Aspirator/ blower fan | Routing valve (normally open to 51) | Routing valve (open path to pipe 49 when on) | Routing valve to tank 1 (if off, or to pipe 61 if on) | Vacuum pump (also open valve 53) | Routing valve (off = to drain/ rec tk, on = To CIP tks) |
|---|---|---|---|---|---|---|---|---|---|
| | | | 38 | 45 | 46 | 47 | 48 | 54 | 55 |
| 0 | | Home | | | | | | | |
| 10 | | Steps 1-10 same as chart 6 | | | | | | | |
| 11 | Caustic | Drain CIP suction & disch. | | | | | X | | |
| 12 | | Push + atom. caustic & pull | X | | | | | | X |
| 13 | | Push + atom. caustic & pull | X | | | | | | X |
| 14 | | Push + atom. caustic & pull | X | | | | | | X |
| 15 | | Push + atom. caustic & pull | X | | | | | | X |
| 16 | | Circulate via silo spray ball | X | X | X | X | X | | X |

TABLE 8A-continued

| Step | Phase | Step Description | | | | | | |
|---|---|---|---|---|---|---|---|---|
| 17 | | Circulate via silo overflow | X | X | X | X | X | X |
| 18 | | Circulate via silo inlet valve | X | X | X | X | X | X |
| 19 | | Circulate via silo by pass | X | X | X | X | X | X |
| 20 | | Repeat steps 12-19x tm(s) | | | | | | |
| 21 | Rinse | Partial rinse to silo & pull | X | | | | | X |
| 22 | | Push & pull to caustic tank | X | | | | | X |
| 23 | | Push & pull to caustic tank | X | | | | | X |
| 24 | | Push & pull to caustic tank | X | | | | | X |
| 25 | | Push & pull to empty lines | X | | | | | X |
| 26 | | Repeat steps 22-25x tm(s) | | | | | | |
| 27 | | Drain silo & lines | | | | | | |
| 28 | Sani- | Partial sani. sol'n preparat. | | | | | | |
| 29 | tizing | Partial sani to silo & pull | X | | | | | |
| 30 | | Drain CIP suction & disch. | | | | | X | |
| 31 | | Push + atom. Sani. & pull | X | | | | | |
| 32 | | Push + atom. Sani. & pull | X | | | | | |
| 33 | | Push + atom. Sani. & pull | X | | | | | |
| 34 | | Push + atom. Sani. & pull | X | | | | | |
| 35 | | Circulate via silo spray ball | X | X | X | X | X | |
| 36 | | Circulate via silo overflow | X | X | X | X | X | |
| 37 | | Circulate via silo inlet valve | X | X | X | X | X | |
| 38 | | Circulate via silo by pass | X | X | X | X | X | |
| 39 | | Final drain (silo & lines) | | | | | X | |
| 40 | | | | | | | | |
| 41 | | | | | | | | |

TABLE 8B

CHART 8 (PAGE 2) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS FOLLOWED BY THE CIRCULATION OF THE ATOMIZED SOLUTION)

| Step | Phase | STEP DESCRIPTION Item number | Step time or volume | Routing valve (open path from 51 to 49 when on) 56 | CIP drain valve (normally open to drain) 58 | Chemical injection port (add by conductivity or flow) 59 | Routing valve to recov. silo (also turn on valve 81) 62 | Fresh water tank outlet valve 63 | Chemical solution tanks blocking valve 64 |
|---|---|---|---|---|---|---|---|---|---|
| 0 | | Home | | | | | | | |
| 10 | | Steps 1-10 same as chart 6 | | | | | | | |
| 11 | Caustic | Drain CIP suction & disch. | | | | | | | X |
| 12 | | Push + atom. caustic & pull | | | | | | | |
| 13 | | Push + atom. caustic & pull | | | | | | | |
| 14 | | Push + atom. caustic & pull | | | | | | | |
| 15 | | Push + atom. caustic & pull | | | | | | | |
| 16 | | Circulate via silo spray ball | | | | | | | |
| 17 | | Circulate via silo overflow | | | | | | | |
| 18 | | Circulate via silo inlet valve | | | | | | | |
| 19 | | Circulate via silo by pass | | | | | | | |
| 20 | | Repeat steps 12-19x tm(s) | | | | | | | |
| 21 | Rinse | Partial rinse to silo & pull | | | | | | X | |
| 22 | | Push & pull to caustic tank | | | | | | | |
| 23 | | Push & pull to caustic tank | | | | | | | |
| 24 | | Push & pull to caustic tank | | | | | | | |
| 25 | | Push & pull to empty lines | | | | | | | |
| 26 | | Repeat steps 22-25x tm(s) | | | | | | | |
| 27 | | Drain silo & lines | | | | | | | |
| 28 | Sani- | Partial sani. sol'n preparat. | | | | X | | X | |
| 29 | tizing | Partial sani to silo & pull | | | | | | | |
| 30 | | Drain CIP suction & disch. | | | | | | | X |
| 31 | | Push + atom. Sani. & pull | | | | | | | |
| 32 | | Push + atom. Sani. & pull | | | | | | | |
| 33 | | Push + atom. Sani. & pull | | | | | | | |
| 34 | | Push + atom. Sani. & pull | | | | | | | |
| 35 | | Circulate via silo spray ball | | | | | | | |
| 36 | | Circulate via silo overflow | | | | | | | |
| 37 | | Circulate via silo inlet valve | | | | | | | |
| 38 | | Circulate via silo by pass | | | | | | | |
| 39 | | Final drain (silo & lines) | | X | | | | | |
| 40 | | | | | | | | | |
| 41 | | | | | | | | | |

TABLE 8B-continued

CHART 8 (PAGE 2)
REFERENCE DRAWING 7
SILO WASH & SANITIZE
PROGRAM USING THE
PUSH & PULL METHOD
FOR THE RINSE STEPS &
THE ATOMIZING METHOD
FOR THE WASH &
SANITIZE STEPS
(CHEMICAL ATOMIZATION
IS FOLLOWED BY THE
CIRCULATION OF THE
ATOMIZED SOLUTION)

| Step | Phase | Item number / STEP DESCRIPTION | Caustic tank outlet valve 65 | Recovered rinse tank outlet valve 66 | Acid tank outlet valve 67 | Caustic tank return valve (switch to 70 at high level) 69 | Recov. rinse tank return valve (to drain at high level) 70 | Acid tank return valve (switch to drain if at high level) 71 | Silo by pass valve 572 | Routing valve to flow panel and to selected silo 573 |
|---|---|---|---|---|---|---|---|---|---|---|
| 0 |  | Home |  |  |  |  |  |  |  |  |
| 10 |  | Steps 1-10 same as chart 6 |  |  |  |  |  |  |  |  |
| 11 | Caustic | Drain CIP suction & disch. |  |  |  |  |  |  |  |  |
| 12 |  | Push + atom. caustic & pull |  |  |  | X |  |  |  | X |
| 13 |  | Push + atom. caustic & pull |  |  |  | X |  |  |  | X |
| 14 |  | Push + atom. caustic & pull |  |  |  | X |  |  |  | X |
| 15 |  | Push + atom. caustic & pull |  |  |  | X |  |  | X |  |
| 16 |  | Circulate via silo spray ball |  |  |  |  |  |  |  | X |
| 17 |  | Circulate via silo overflow |  |  |  |  |  |  |  | X |
| 18 |  | Circulate via silo inlet valve |  |  |  |  |  |  |  | X |
| 19 |  | Circulate via silo by pass |  |  |  |  |  |  | X |  |
| 20 |  | Repeat steps 12-19x tm(s) |  |  |  |  |  |  |  |  |
| 21 | Rinse | Partial rinse to silo & pull |  |  |  | X |  |  |  | X |
| 22 |  | Push & pull to caustic tank |  |  |  | X |  |  |  | X |
| 23 |  | Push & pull to caustic tank |  |  |  | X |  |  |  | X |
| 24 |  | Push & pull to caustic tank |  |  |  | X |  |  |  | X |
| 25 |  | Push & pull to empty lines |  |  |  | X |  |  | X |  |
| 26 |  | Repeat steps 22-25x tm(s) |  |  |  |  |  |  |  |  |
| 27 |  | Drain silo & lines |  |  |  |  |  |  |  | X |
| 28 | Sani- | Partial sani. sol'n preparat. |  |  |  |  |  |  |  |  |
| 29 | tizing | Partial sani to silo & pull |  |  |  |  |  |  |  | X |
| 30 |  | Drain CIP suction & disch. |  |  |  |  |  |  |  |  |
| 31 |  | Push + atom. Sani. & pull |  |  |  |  |  |  |  | X |
| 32 |  | Push + atom. Sani. & pull |  |  |  |  |  |  |  | X |
| 33 |  | Push + atom. Sani. & pull |  |  |  |  |  |  |  | X |
| 34 |  | Push + atom. Sani. & pull |  |  |  |  |  |  | X |  |
| 35 |  | Circulate via silo spray ball |  |  |  |  |  |  |  | X |
| 36 |  | Circulate via silo overflow |  |  |  |  |  |  |  | X |
| 37 |  | Circulate via silo inlet valve |  |  |  |  |  |  |  | X |
| 38 |  | Circulate via silo by pass |  |  |  |  |  |  | X |  |
| 39 |  | Final drain (silo & lines) |  |  |  |  |  |  | X | X |
| 40 |  |  |  |  |  |  |  |  |  |  |
| 41 |  |  |  |  |  |  |  |  |  |  |

CHART 8 (PAGE 2)
REFERENCE DRAWING 7
SILO WASH & SANITIZE
PROGRAM USING THE
PUSH & PULL METHOD
FOR THE RINSE STEPS &
THE ATOMIZING METHOD
FOR THE WASH &
SANITIZE STEPS
(CHEMICAL ATOMIZATION
IS FOLLOWED BY THE
CIRCULATION OF THE
ATOMIZED SOLUTION)

| Step | Phase | Item number / STEP DESCRIPTION | Suction pump prior to silo 574 | Silo inlet valve 75 | Silo outlet valve 576 | Routing valve to silo spray ball 877 | Routing valve to silo inlet valve & overflow pipe 878 | Silo vent valve (off = open/opens if vacuum or pressure) 879 | Silo & return line drain valve 580 |
|---|---|---|---|---|---|---|---|---|---|
| 0 |  | Home |  |  |  |  |  |  |  |
| 10 |  | Steps 1-10 same as chart 6 |  |  |  |  |  |  |  |
| 11 | Caustic | Drain CIP suction & disch. |  |  |  |  |  |  |  |
| 12 |  | Push + atom. caustic & pull | X |  | X | X |  | X |  |
| 13 |  | Push + atom. caustic & pull | X |  | X |  | X | X |  |
| 14 |  | Push + atom. caustic & pull | X | X | X |  | X | X |  |
| 15 |  | Push + atom. caustic & pull |  |  |  |  |  | X |  |
| 16 |  | Circulate via silo spray ball | X |  | X | X |  | X |  |
| 17 |  | Circulate via silo overflow | X |  | X |  | X | X |  |
| 18 |  | Circulate via silo inlet valve | X | X | X |  | X | X |  |
| 19 |  | Circulate via silo by pass |  |  |  |  |  |  |  |
| 20 |  | Repeat steps 12-19x tm(s) |  |  |  |  |  |  |  |
| 21 | Rinse | Partial rinse to silo & pull | X | X | X |  | X |  |  |

TABLE 8B-continued

| | | | | | | | | |
|---|---|---|---|---|---|---|---|---|
| 22 | | Push & pull to caustic tank | X | | X | X | | X |
| 23 | | Push & pull to caustic tank | X | | X | | X | X |
| 24 | | Push & pull to caustic tank | X | X | X | | X | X |
| 25 | | Push & pull to empty lines | | | | | | |
| 26 | | Repeat steps 22-25x tm(s) | | | | | | |
| 27 | | Drain silo & lines | | X | X | X | X | | X |
| 28 | Sani- | Partial sani. sol'n preparat. | | | | | | |
| 29 | tizing | Partial sani to silo & pull | X | | X | X | | X |
| 30 | | Drain CIP suction & disch. | | | | | | |
| 31 | | Push + atom. Sani. & pull | X | | X | X | | X |
| 32 | | Push + atom. Sani. & pull | X | | X | | X | X |
| 33 | | Push + atom. Sani. & pull | X | X | X | | X | X |
| 34 | | Push + atom. Sani. & pull | | | | | | X |
| 35 | | Circulate via silo spray ball | X | | X | X | | X |
| 36 | | Circulate via silo overflow | X | | X | | X | X |
| 37 | | Circulate via silo inlet valve | X | X | X | | X | X |
| 38 | | Circulate via silo by pass | | | | | | |
| 39 | | Final drain (silo & lines) | | X | X | X | X | | X |
| 40 | | | | | | | | |
| 41 | | | | | | | | |

TABLE 9A

CHART 9 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION)

| Step | Phase | STEP DESCRIPTION Item number | Step time or volume | Circulation tk outlet valve - also open 3 in rinse low level 2 | CIP supply pump 6 | Aqueduc water valve 8 | Aqueduc block & bleed water valve 9 | Steam shutt off valve 15 | Routing valve from CIP to circuit 18 |
|---|---|---|---|---|---|---|---|---|---|
| 0 | | Home | | | | | | | |
| 10 | | Steps 1-10 same as chart 6 | | | | | | | |
| 11 | Caustic | Push atom. caustic & press. | | | | | | | |
| 12 | | Push atom. caustic & pull | | | | | | | |
| 13 | | Push atom. caustic & press. | | | | | | | |
| 14 | | Push atom. caustic & pull | | | | | | | |
| 15 | | Push atom. caustic & pull | | | | | | | |
| 16 | | Repeat steps 11-15x tm(s) | | | | | | | |
| 17 | Rinse | Partial rinse to silo & pull | | | X | | | | X |
| 18 | | Push & pull to caustic tank | | | | | | | |
| 19 | | Push & pull to caustic tank | | | | | | | |
| 20 | | Push & pull to caustic tank | | | | | | | |
| 21 | | Push & pull to empty lines | | | | | | | |
| 22 | | Repeat steps 17-21x tm(s) | | | | | | | |
| 23 | | Drain silo & lines | | | | | | | |
| 24 | Sani- | Partial sani sol'n preparat. | | | X | | | | |
| 25 | tizing | Partial sani sol'n to silo | | X | X | | | | X |
| 26 | | Push + atom. sani & press. | | | | | | | |
| 27 | | Push + atom. sani & pull | | | | | | | |
| 28 | | Push + atom. sani & press. | | | | | | | |
| 29 | | Push + atom. sani & pull | | | | | | | |
| 30 | | Push + atom. sani & pull | | | | | | | |
| 31 | | Push + atom. sani & pull | | | | | | | |
| 32 | | Final drain (silo & lines) | | X | | X | | | X |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

TABLE 9A-continued

| | | | | | | | | | Routing valves - |
|---|---|---|---|---|---|---|---|---|---|
| | | CHART 9 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION) STEP DESCRIPTION | Routing valve to circulation tank 1 | Chemical & compressed gas main valve | Atomized chemical valve (caustic or acid or sanitizer) | Compressed gas valve | Live steam valve (flow controlled) | Flow restriction valve (normally open to circuit) | also activate 35 (reverse flow valves) |
| Step | Phase | Item number | 20 | 23 | 24 | 26 | 27 | 31 | 32 |
| 0 | | Home | | | | | | | |
| 10 | | Steps 1-10 same as chart 6 | | | | | | | |
| 11 | Caustic | Push atom. caustic & press. | | X | X | X | X | | |
| 12 | | Push atom. caustic & pull | | X | X | X | X | | |
| 13 | | Push atom. caustic & press. | | X | X | X | X | | |
| 14 | | Push atom. caustic & pull | | X | X | X | X | | |
| 15 | | Push atom. caustic & pull | | X | X | X | X | | |
| 16 | | Repeat steps 11-15x tm(s) | | | | | | | |
| 17 | Rinse | Partial rinse to silo & pull | | | | | | | |
| 18 | | Push & pull to caustic tank | | X | | X | | | |
| 19 | | Push & pull to caustic tank | | X | | X | | | |
| 20 | | Push & pull to caustic tank | | X | | X | | | |
| 21 | | Push & pull to empty lines | | X | | X | | | |
| 22 | | Repeat steps 17-21x tm(s) | | | | | | | |
| 23 | | Drain silo & lines | | X | | X | | | |
| 24 | Sanitizing | Partial sani sol'n preparat. | X | | | | | | |
| 25 | | Partial sani sol'n to silo | | | | | | | |
| 26 | | Push + atom. sani & press. | | X | X | X | | | |
| 27 | | Push + atom. sani & pull | | X | X | X | | | |
| 28 | | Push + atom. sani & press. | | X | X | X | | | |
| 29 | | Push + atom. sani & pull | | X | X | X | | | |
| 30 | | Push + atom. sani & pull | | X | X | X | | | |
| 31 | | Push + atom. sani & pull | | X | X | X | | | |
| 32 | | Final drain (silo & lines) | | | | | | | |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

| | | CHART 9 (PAGE 1) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION) STEP DESCRIPTION | Aspirator/ blower fan | Aspirator/ blower fan | Routing valve (normally open to 51) | Routing valve (open path to pipe 49 when on) | Routing valve to tank 1 (if off, or to pipe 61 if on) | Vacuum pump (also open valve 53) | Routing valve (off = to drain/rec tk, on = To CIP tks) |
|---|---|---|---|---|---|---|---|---|
| Step | Phase | Item number | 38 | 45 | 46 | 47 | 48 | 54 | 55 |
| 0 | | Home | | | | | | | |
| 10 | | Steps 1-10 same as chart 6 | | | | | | | |
| 11 | Caustic | Push atom. caustic & press. | X | | | | | | X |
| 12 | | Push atom. caustic & pull | X | | | | | | X |
| 13 | | Push atom. caustic & press. | X | | | | | | X |
| 14 | | Push atom. caustic & pull | X | | | | | | X |
| 15 | | Push atom. caustic & pull | X | | | | | | X |
| 16 | | Repeat steps 11-15x tm(s) | | | | | | | |
| 17 | Rinse | Partial rinse to silo & pull | X | | | | | | X |
| 18 | | Push & pull to caustic tank | X | | | | | | X |
| 19 | | Push & pull to caustic tank | X | | | | | | X |
| 20 | | Push & pull to caustic tank | X | | | | | | X |

TABLE 9A-continued

| Step | Phase | Item number | | | | | | | |
|---|---|---|---|---|---|---|---|---|---|
| 21 | | Push & pull to empty lines | X | | | | | | X |
| 22 | | Repeat steps 17-21x tm(s) | | | | | | | |
| 23 | | Drain silo & lines | | | | | | | |
| 24 | Sani- | Partial sani sol'n preparat. | | | | | | | |
| 25 | tizing | Partial sani sol'n to silo | X | | | | | | |
| 26 | | Push + atom. sani & press. | | | | | | | |
| 27 | | Push + atom. sani & pull | X | | | | | | |
| 28 | | Push + atom. sani & press. | | | | | | | |
| 29 | | Push + atom. sani & pull | X | | | | | | |
| 30 | | Push + atom. sani & pull | X | | | | | | |
| 31 | | Push + atom. sani & pull | X | | | | | | |
| 32 | | Final drain (silo & lines) | | | | | | | |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

TABLE 9B

CHART 9 (PAGE 2) REFERENCE DRAWING 7 SILO WASH & SANITIZE PROGRAM USING THE PUSH & PULL METHOD FOR THE RINSE STEPS & THE ATOMIZING METHOD FOR THE WASH & SANITIZE STEPS (CHEMICAL ATOMIZATION IS DONE WITH PRESSURIZATION OF THE CIRCUIT FOLLOWED BY DEPRESSURIZATION)

| Step | Phase | STEP DESCRIPTION Item number | Step time or volume | Routing valve (open path from 51 to 49 when on) 56 | CIP drain valve (normally open to drain) 58 | Chemical injection port (add by conductivity or flow) 59 | Routing valve to recov. silo (also turn on valve 81) 62 | Fresh water tank outlet valve 63 | Chemical solution tanks blocking valve 64 | Caustic tank outlet valve 65 |
|---|---|---|---|---|---|---|---|---|---|---|
| 0 | | Home | | | | | | | | |
| 10 | Caustic | Steps 1-10 same as chart 6 | | | | | | | | |
| 11 | | Push atom. caustic & press. | | | | | | | | |
| 12 | | Push atom. caustic & pull | | | | | | | | |
| 13 | | Push atom. caustic & press. | | | | | | | | |
| 14 | | Push atom. caustic & pull | | | | | | | | |
| 15 | | Push atom. caustic & pull | | | | | | | | |
| 16 | | Repeat steps 11-15x tm(s) | | | | | | | | |
| 17 | Rinse | Partial rinse to silo & pull | | | | | | X | | |
| 18 | | Push & pull to caustic tank | | | | | | | | |
| 19 | | Push & pull to caustic tank | | | | | | | | |
| 20 | | Push & pull to caustic tank | | | | | | | | |
| 21 | | Push & pull to empty lines | | | | | | | | |
| 22 | | Repeat steps 17-21x tm(s) | | | | | | | | |
| 23 | | Drain silo & lines | | | | | | | | |
| 24 | Sani- | Partial sani sol'n preparat. | | | | X | | X | | |
| 25 | tizing | Partial sani sol'n to silo | | | | | | | | |
| 26 | | Push + atom. sani & press. | | | | | | | | |
| 27 | | Push + atom. sani & pull | | | | | | | | |
| 28 | | Push + atom. sani & press. | | | | | | | | |
| 29 | | Push + atom. sani & pull | | | | | | | | |
| 30 | | Push + atom. sani & pull | | | | | | | | |
| 31 | | Push + atom. sani & pull | | | | | | | | |
| 32 | | Final drain (silo & lines) | | | | | | | X | |
| 33 | | | | | | | | | | |
| 34 | | | | | | | | | | |
| 35 | | | | | | | | | | |
| 36 | | | | | | | | | | |
| 37 | | | | | | | | | | |
| 38 | | | | | | | | | | |
| 39 | | | | | | | | | | |
| 40 | | | | | | | | | | |
| 41 | | | | | | | | | | |

TABLE 9B-continued

CHART 9 (PAGE 2)
REFERENCE DRAWING 7
SILO WASH & SANITIZE
PROGRAM USING THE
PUSH & PULL METHOD
FOR THE RINSE STEPS &
THE ATOMIZING METHOD
FOR THE WASH &
SANITIZE STEPS
(CHEMICAL ATOMIZATION
IS DONE WITH
PRESSURIZATION OF THE
CIRCUIT FOLLOWED BY
DEPRESSURIZATION)

| Step | Phase | Step Description / Item number | Recovered rinse tank outlet valve 66 | Acid tank outlet valve 67 | Caustic tank return valve (switch to 70 at high level) 69 | Recov. rinse tank return valve (to drain at high level) 70 | Acid tank return valve (switch to drain if at high level) 71 | Silo by pass valve 572 | Routing valve to flow panel and to selected silo 573 |
|---|---|---|---|---|---|---|---|---|---|
| 0 |  | Home |  |  |  |  |  |  |  |
| 10 | Caustic | Steps 1-10 same as chart 6 |  |  |  |  |  |  |  |
| 11 |  | Push atom. caustic & press. |  |  | X |  |  |  | X |
| 12 |  | Push atom. caustic & pull |  |  | X |  |  |  | X |
| 13 |  | Push atom. caustic & press. |  |  | X |  |  |  | X |
| 14 |  | Push atom. caustic & pull |  |  | X |  |  |  | X |
| 15 |  | Push atom. caustic & pull |  |  | X |  |  |  | X |
| 16 |  | Repeat steps 11-15x tm(s) |  |  |  |  |  |  |  |
| 17 | Rinse | Partial rinse to silo & pull |  |  |  |  |  |  | X |
| 18 |  | Push & pull to caustic tank |  |  | X |  |  |  | X |
| 19 |  | Push & pull to caustic tank |  |  | X |  |  |  | X |
| 20 |  | Push & pull to caustic tank |  |  | X |  |  |  | X |
| 21 |  | Push & pull to empty lines |  |  | X |  |  | X |  |
| 22 |  | Repeat steps 17-21x tm(s) |  |  |  |  |  |  |  |
| 23 |  | Drain silo & lines |  |  |  |  |  | X | X |
| 24 | Sanitizing | Partial sani sol'n preparat. |  |  |  |  |  |  |  |
| 25 |  | Partial sani sol'n to silo |  |  |  |  |  |  | X |
| 26 |  | Push + atom. sani & press. |  |  |  |  |  |  | X |
| 27 |  | Push + atom. sani & pull |  |  |  |  |  |  | X |
| 28 |  | Push + atom. sani & press. |  |  |  |  |  |  | X |
| 29 |  | Push + atom. sani & pull |  |  |  |  |  |  | X |
| 30 |  | Push + atom. sani & pull |  |  |  |  |  |  | X |
| 31 |  | Push + atom. sani & pull |  |  |  |  |  | X |  |
| 32 |  | Final drain (silo & lines) |  |  |  |  |  | X | X |
| 33 |  |  |  |  |  |  |  |  |  |
| 34 |  |  |  |  |  |  |  |  |  |
| 35 |  |  |  |  |  |  |  |  |  |
| 36 |  |  |  |  |  |  |  |  |  |
| 37 |  |  |  |  |  |  |  |  |  |
| 38 |  |  |  |  |  |  |  |  |  |
| 39 |  |  |  |  |  |  |  |  |  |
| 40 |  |  |  |  |  |  |  |  |  |
| 41 |  |  |  |  |  |  |  |  |  |

CHART 9 (PAGE 2)
REFERENCE DRAWING 7
SILO WASH & SANITIZE
PROGRAM USING THE
PUSH & PULL METHOD
FOR THE RINSE STEPS &
THE ATOMIZING METHOD
FOR THE WASH &
SANITIZE STEPS
(CHEMICAL ATOMIZATION
IS DONE WITH
PRESSURIZATION OF THE
CIRCUIT FOLLOWED BY
DEPRESSURIZATION)

| Step | Phase | Step Description / Item number | Suction pump prior to silo 574 | Silo inlet valve 75 | Silo outlet valve 576 | Routing valve to silo spray ball 877 | Routing valve to silo inlet valve & overflow pipe 878 | Silo vent valve (off = open/opens if vacuum or pressure) 879 | Silo & return line drain valve 580 |
|---|---|---|---|---|---|---|---|---|---|
| 0 |  | Home |  |  |  |  |  |  |  |
| 10 | Caustic | Steps 1-10 same as chart 6 |  |  |  |  |  |  |  |
| 11 |  | Push atom. caustic & press. | X |  | X |  |  | X | X |
| 12 |  | Push atom. caustic & pull | X |  | X | X |  |  | X |
| 13 |  | Push atom. caustic & press. | X |  | X |  |  | X | X |
| 14 |  | Push atom. caustic & pull | X |  | X |  | X |  | X |
| 15 |  | Push atom. caustic & pull | X | X | X |  | X |  | X |
| 16 |  | Repeat steps 11-15x tm(s) |  |  |  |  |  |  |  |
| 17 | Rinse | Partial rinse to silo & pull | X |  | X | X |  | X | X |
| 18 |  | Push & pull to caustic tank | X |  | X | X |  |  | X |
| 19 |  | Push & pull to caustic tank | X |  | X |  | X |  | X |
| 20 |  | Push & pull to caustic tank | X | X | X |  | X |  | X |

TABLE 9B-continued

| | | | | | | | | |
|---|---|---|---|---|---|---|---|---|
| 21 | | Push & pull to empty lines | | | | | | |
| 22 | | Repeat steps 17-21x tm(s) | | | | | | |
| 23 | | Drain silo & lines | | | X | X | X | | X |
| 24 | Sanitizing | Partial sani sol'n preparat. | | | | | | | |
| 25 | | Partial sani sol'n to silo | X | | X | X | | X | |
| 26 | | Push + atom. sani & press. | X | | X | | | X | |
| 27 | | Push + atom. sani & pull | X | | X | X | | X | |
| 28 | | Push + atom. sani & press. | X | | X | | | X | |
| 29 | | Push + atom. sani & pull | X | | X | | X | X | |
| 30 | | Push + atom. sani & pull | X | X | X | | X | X | |
| 31 | | Push + atom. sani & pull | | | | | | X | |
| 32 | | Final drain (silo & lines) | | X | X | X | X | | X |
| 33 | | | | | | | | | |
| 34 | | | | | | | | | |
| 35 | | | | | | | | | |
| 36 | | | | | | | | | |
| 37 | | | | | | | | | |
| 38 | | | | | | | | | |
| 39 | | | | | | | | | |
| 40 | | | | | | | | | |
| 41 | | | | | | | | | |

What is claimed is:

1. A method for cleaning an interior surface of a processing equipment using a treatment liquid, the processing equipment including a pipe section defining pipe section first and second ends, the pipe section defining a pipe section volume delimited by the pipe section first and second ends, the pipe section being initially at an initial internal pressure, said method comprising:

introducing a coherent predetermined volume of the treatment liquid into the pipe section at a location substantially adjacent the pipe section first end, the predetermined volume of the treatment liquid filling only part of the pipe section, the predetermined volume being substantially smaller than the pipe section volume; and moving the predetermined volume of the treatment liquid through the pipe section by reducing an internal pressure within the pipe section at a location substantially adjacent the pipe section second end to a level substantially below the initial internal pressure, and simultaneously increasing an internal pressure within the pipe section at a location substantially adjacent the pipe section first end to a level substantially above the initial internal pressure;

wherein simultaneously reducing and increasing said internal pressure respectively substantially adjacent the pipe section second and first ends moves the predetermined volume of liquid in the pipe section.

2. A method as defined in claim 1, further comprising recovering the predetermined volume of the treatment liquid after having moved the predetermined volume of the treatment liquid through the pipe section.

3. A method as defined in claim 2, further comprising, after having recovered the predetermined volume of the treatment liquid;

reintroducing the predetermined volume of the treatment liquid into the pipe section at a location substantially adjacent the pipe section first end; and recirculating the predetermined volume of the treatment liquid through the pipe section by simultaneously:

reducing an internal pressure within the pipe section at a location substantially adjacent the pipe section second end to a level substantially below the initial internal pressure; and increasing an internal pressure within the pipe section at a location substantially adjacent the pipe section first end to a level substantially above the initial internal pressure.

4. A method as defined in claim 2, further comprising, after recovering the predetermined volume:

reintroducing the predetermined volume of the treatment liquid into the pipe section at a location substantially adjacent the pipe section second end; and recirculating the predetermined volume of the treatment liquid through the pipe section by simultaneously reducing an internal pressure within the pipe section at a location substantially adjacent the pipe section first end to a level substantially below the initial internal pressure; and increasing an internal pressure within the pipe section at a location substantially adjacent the pipe section second end to a level substantially above the Initial internal pressure.

5. A method as defined in claim 1, wherein increasing an internal pressure within the pipe section at a location substantially adjacent the pipe section first end to a level substantially above the initial internal pressure includes introducing a gas into the pipe section.

6. A method as defined in claim 5, further comprising performing a substantial separation between a gaseous phase and a liquid phase from the recovered predetermined volume of the treatment liquid.

7. A method as defined in claim 1, further comprising adjusting a property of the treatment liquid prior to introducing the predetermined volume of the treatment liquid into the pipe section.

8. A method as defined in claim 1, wherein cleaning the interior surface of the processing equipment is performed further using an other treatment liquid, said method further comprising:

introducing an other predetermined volume of the other treatment liquid into the pipe section at a location substantially adjacent the pipe section first end, the other predetermined volume being substantially smaller than the pipe section volume, the other predetermined volume of the treatment liquid filling only part of the pipe section; and moving the other predetermined volume of the other treatment liquid through the pipe section by simultaneously reducing an internal pressure within the pipe section at a location substantially adjacent the pipe section second end to a level substantially below the Initial internal pressure; and increasing an internal pressure within the pipe section at a location substantially adjacent the pipe section first end to a level substantially above the initial internal pressure.

9. A method as defined in claim 1, wherein the pipe section contains a process substance prior to introducing the predetermined volume of the treatment liquid, said method further comprising recovering at least in part the process substance.

10. A method as defined in claim 9, wherein recovering the process substance includes using water as the treatment liquid.

11. A method as defined in claim 10, wherein recovering the process substance includes recovering a water and process substance combination further to moving the predetermined volume of the treatment liquid through the pipe section.

12. A method as defined in claim 1, wherein the treatment liquid includes a liquid selected from the set consisting of: water, an acid solution, a caustic solution, a germicidal solution, an alkaline solution, a buffer solution, a water-based solution containing an organic solvent, an enzyme-containing solution, an oxidizing component, a distaining solution, a passivating solution and a biologically active mixture.

13. A method as defined in claim 1, wherein increasing a pressure at the location substantially adjacent the pipe section first end includes introducing a gas under pressure at the location substantially adjacent the pipe section first end.

14. A method as defined in claim 1, further comprising:
introducing steam into the pipe section; and
moving the steam within the pipe section.

15. A method as defined in claim 1, further comprising adjusting a property of the predetermined volume of the treatment liquid by moving the predetermined volume of the treatment liquid in a circuit excluding the pipe section prior to introducing the predetermined volume of the treatment liquid into the pipe section, wherein adjusting a property of the predetermined volume of the treatment liquid includes adjusting a property selected from the set consisting of a pH, a temperature and a solute concentration.

16. A method as defined in claim 1, wherein the reduction of the internal pressure within the pipe section at a location substantially adjacent the pipe section second end to a level substantially below the initial internal pressure is performed after the introduction of the predetermined volume of the treatment liquid into the pipe section.

17. A method as defined in claim 16, wherein the reduction of the internal pressure within the pipe section at a location substantially adjacent the pipe section second end to a level substantially below the initial internal pressure is also performed during at least part of the introduction of the predetermined volume of the treatment liquid into the pipe section.

18. A method as defined in claim 1, wherein the reduction of the internal pressure within the pipe section at a location substantially adjacent the pipe section second end to a level substantially below the initial internal pressure is also performed at least in part prior to the introduction of the predetermined volume of the treatment liquid into the pipe section.

19. A method as defined in claim 1, wherein the processing equipment includes a first pipe defining a first pipe first end and a first pipe second end, a vessel in fluid communication with the first pipe, and a second pipe in fluid communication with the vessel, the second pipe defining a second pipe first end and a second pipe second end, said method comprising:
introducing the predetermined volume of the treatment liquid into the first pipe at a location substantially adjacent the first pipe first end, the predetermined volume being substantially smaller than the first pipe volume;
moving the predetermined volume of the treatment liquid through the first pipe from the first pipe first end to the first pipe second end by simultaneously
reducing the internal pressure within the first pipe at a location substantially adjacent the first pipe second end to a level substantially below the initial internal pressure; and
increasing the internal pressure within the first pipe at a location substantially adjacent the first pipe first end to a level substantially over the initial internal pressure; and
moving the predetermined volume of the treatment liquid through the second pipe from the second pipe first end to the second pipe second end by simultaneously
reducing the internal pressure within the second pipe at a location substantially adjacent the second pipe second end to a level substantially below the initial internal pressure; and
increasing the internal pressure within the second pipe at a location substantially adjacent the second pipe first end to a level substantially over the initial internal pressure.

20. A method as defined in claim 19, further comprising introducing the predetermined volume of the treatment liquid into the vessel after moving the predetermined volume of the treatment liquid through the first pipe and prior to moving the predetermined volume of the treatment liquid through the second pipe.

21. A method as defined in claim 1, further comprising:
introducing another predetermined volume of the treatment liquid into the pipe section at a location substantially adjacent the pipe section second end; and
moving the other predetermined volume of the treatment liquid through the pipe section by simultaneously
reducing an internal pressure within the pipe section at a location substantially adjacent the pipe section first end to a level substantially below the initial internal pressure; and
increasing an internal pressure within the pipe section at a location substantially adjacent the pipe section second end to a level substantially above the initial internal pressure.

22. A method as defined in claim 1, wherein said predetermined volume of the treatment liquid is a liquid solution before being moved in the pipe section.

23. A method as defined in claim 1, wherein:
a difference in pressure between the initial internal pressure and a reduced internal pressure resulting from the reducing the internal pressure within the pipe section at the location substantially adjacent the pipe section second end defines a first pressure differential;
a difference in pressure between the initial internal pressure and an increased internal pressure resulting from the increasing the internal pressure within the pipe section at the location substantially adjacent the pipe section first end defines a second pressure differential; and
the difference between the second pressure differential and the first pressure differential being less than about 10%.

24. A method as defined in claim 23, wherein the second pressure differential is substantially equal to the first pressure differential.

* * * * *